(12) United States Patent
Schalk

(10) Patent No.: US 7,622,288 B2
(45) Date of Patent: Nov. 24, 2009

(54) SESQUITERPENE SYNTHASES FROM PATCHOULI

(75) Inventor: Michel Schalk, Collonges-Sous-Saleve (FR)

(73) Assignee: Firmenich SA, Geneva (CH)

( * ) Notice: Subject to any disclaimer, the term of this patent is extended or adjusted under 35 U.S.C. 154(b) by 67 days.

(21) Appl. No.: 11/440,105

(22) Filed: May 23, 2006

(65) Prior Publication Data

US 2006/0206957 A1    Sep. 14, 2006

Related U.S. Application Data

(63) Continuation of application No. PCT/IB2004/003836, filed on Nov. 19, 2004.

(60) Provisional application No. 60/525,512, filed on Nov. 26, 2003.

(30) Foreign Application Priority Data

Dec. 9, 2003    (WO) ................ PCT/IB03/06459

(51) Int. Cl.
*C12N 9/10*    (2006.01)
*C07H 21/04*    (2006.01)

(52) U.S. Cl. .............. 435/193; 435/183; 435/320.1; 435/252.3; 435/325; 435/410; 536/23.1; 536/23.2; 536/23.6

(58) Field of Classification Search .................. None
See application file for complete search history.

(56) References Cited

U.S. PATENT DOCUMENTS

| 6,559,297 B2 | 5/2003 | Chappell et al. ........... 536/23.1 |
| 2004/0161819 A1 | 8/2004 | Aharoni et al. ............ 435/69.1 |
| 2005/0019882 A1 | 1/2005 | Bouwmeester et al. ...... 435/155 |

FOREIGN PATENT DOCUMENTS

| WO | WO 99/18118 A1 | 4/1999 |
| WO | WO 99/38957 A1 | 8/1999 |
| WO | WO 00/55338 A1 | 9/2000 |
| WO | WO 02/064764 A2 | 8/2002 |
| WO | WO 03/025193 A1 | 3/2003 |

OTHER PUBLICATIONS

Chen (Dec. 5, 1998) GenBank accession Y18484.*
Davis et al. (Feb. 20, 1997) GenBank accession U88318.*
Guo et al. (Jun. 22, 2004) PNAS, vol. 101, No. 25, pp. 9205-9210.*
J. Bohlmann et al., "Plant terpenoid synthases: Molecular biology and phylogenetic analysis," Proc. Natl. Acad. Sci. USA 95:4126-4133 (1998).
S. L. Munck et al., "Purification And Characterization Of The Sesquiterpene Cyclase Patchoulol Synthase From *Pogostemon-cablin*", Archives Of Biochemistry And Biophysics, vol. 282, No. 1, , pp. 58-64 (1990).
C. L. Steel et al., XP002279809, "Sesquiterpene Synthases From Grand Fir (*Abies grandis*). Comparison Of Constitutive And Wound-Induced Activities, And cDNA Isolation, Characterization, And Bacterial Expression Of Delta-Selinene Synthase and Gamma-Humulene Synthase" Journal Of Biological Chemistry, vol. 273, No. 4, pp. 2078-2089 (1998).

* cited by examiner

*Primary Examiner*—Richard G Hutson
(74) *Attorney, Agent, or Firm*—Winston & Strawn LLP

(57) ABSTRACT

The invention relates to sesquiterpene synthases from Patchouli plants (*Pogostemon cablin*), and methods of their production and use. In one embodiment, the invention provides nucleic acids comprising a nucleotide sequence as described herein that encodes for at least one sesquiterpene synthase. In a further embodiment, the invention also provides for sesquiterpene synthases and methods of making and using these enzymes. For example, sesquiterpene synthases of the invention may be used to convert farnesyl-pyrophosphate to various sesquiterpenes including patchoulol, γ-curcumene and other germacrane-type sesquiterpenes.

13 Claims, 23 Drawing Sheets

Figure 3.

```
            10         20         30         40         50         60         70
            |          |          |          |          |          |          |
PatA-14  EPQYSDVRMAIAKLIQMAAAVDDTMDNYATIREAQLLTEALERLNVHEIDTLPDYMKIVYRFVMSWSEDF
PatB-15  ---------------IFDDTFDAYGAFKELQLFKDAIDRWSISCLDELPEYMQIMYKLVLDVFEEI
PatC-16  -------------ITMVSILDDTFDSYGTLQELDLLTKAIERWDIKEINGLPEYUKGFYRVLELHQQF 80         90        100        110        120        130        140
            |          |          |          |          |          |          |
PatA-14  ERDATIKEQMLATPYFKAEMKKLGRAYNQELKWVMERQLPSFEEYMKNSEITSGVYIMFTVUSPYL--NS
PatB-15  ESHMIKQGTSYRLDYAREAIKIVIGGYFDEAKWREEEYKPRMEEYMKVATKSAAYLTLIUVSFVGMKNDI
PatC-16  QEELEKEGSSYAVHYAIEAYKDLARSYDVEAKWFMKGYLPGFEEYLRISLITSTAGYLNVTLLLGM--DS 150        160        170        180        190        200        210
            |          |          |          |          |          |          |
PatA-14  ATQKNIDWLLSQPRLASSTAUVMRCCNDLGSNQRESKGGEVMTSLDCYMKQHGASKQETUSKFKLUIEDE
PatB-15  ATPQAFQWVLSEPQIITASLALARLSNDLVGIEFEKERKHIATAVELYEEEHKVSKEEAVLELRHETESA
PatC-16  VTKEDFEWFSKNPRIAVATQMITRVIDDIATYEVEKGRGQIATGIECYMKEMGVSKEEAMERFYEMGTNA 220        230        240        250        260        270
            |          |          |          |          |          |
PatA-14  WKNLNEE-WAATTCLPKVMVEIFRNMARIAGFCYKNNGDAYTSP-KIVQQCFDALFVNPLRI
PatB-15  WKEINEA-LLEPTTFATPILDRULNSARVLEVFYDKT-DRYTHVDLELQNIIAQLYLIPIP-
PatC-16  WKDVNEVGISWPSSSRDIFVQLRNFNRLIDVTYGKNEDGYSKPEKILKPHIIALFVDQIKL
```

Figure 4.

```
                        10         20         30         40         50         60         70
                 ....|....|....|....|....|....|....|....|....|....|....|....|....|....|
PatAF2           ----MAAFTANAVDMRPPVITIHPR----SKDIFSQFSLDDKLQKQYAQGIEALKEEARSMLMAA---KS
PatBF2           MELKNQSVATISSNASRPLAHYHPD--VWGDRFLLYKPNPSSEAGO-KPVIEELKQQVRSELKEASN-DY
PatCF2           ------MAVQISETVRPFANFSPNPSLWGDQFINHKSKTQQISRIYLEEIEGLKNEVKCMLTSTPEGKM 80         90        100        110        120        130        140
                 ....|....|....|....|....|....|....|....|....|....|....|....|....|....|
PatAF2           AKVMLIDTLERLGLGYHFEKEIEEKLEAIYKKEDGDDY-----DLETTALRFRLLRQHQRRVPCSVFD
PatBF2           MRQLKMVDAIQRLGIESLFEEDIDNALKNLS--ENFDDYCKDKH-DLYAIALSFRLLRQHGYRISCDVFD
PatCF2           ADTVNLIDTLERLGVSYHFEKEIEEKMKHLFNLIKADNYKDHEGCDLYTDALHFRLFRQHGYPISSGWFN 150        160        170        180        190        200        210
                 ....|....|....|....|....|....|....|....|....|....|....|....|....|....|
PatAF2           KFMNKEGKFEEEPLISDVEGLLSLYDAAYLQIHGEHULQEALWFTTHHLTRIEPQLDDHSPLKLKLNRAL
PatBF2           KLKDGEDGFKVP-PSDEALAVVELLEATHLRIHGEVMLDRAFVFARIHLESIEANLN--NPVAKQVHNAL
PatCF2           KWMDGNGKFKES-WKSDAKGLLSLYEACCLRTHGDTLLDEALVFATASLKSMAANLA--SPLRKQVEHAL 220        230        240        250        260        270        280
                 ....|....|....|....|....|....|....|....|....|....|....|....|....|....|
PatAF2           EFP-FYREIPIMYAHFYISVYERDDSRDEVLLKMAKLSYNFLQNLMKKELSQLSRWWNKLELIPNLPYIR
PatBF2           YGYSNRRGMQQVEARKYIPIYEQYASHHGLLKLATLNFNLQOTMHKRELSELSRWYRDLEVPTMLPEAR
PatCF2           EQH-LHFGIPRVEARHFITFYEREEHKNEMLLRFAKLDFNALQALHKEELSEWSKWWKDLDLISKLPY-R 290        300        310        320
                 ....|....|....|....|....|....|....|....|
PatAF2           DSVAGAYLWAVALYFEPQYSDVRMAIAKLIQIA-----------
PatBF2           QRLVETYFWDAGVVFEPENDVARMILVKVQCLISFL--------
PatCF2           DRVVESYFWAVGVYYQPKYSRARWMLTKTIAMTAILDDTYDSYG
```

Figure 5.

Figure 7.
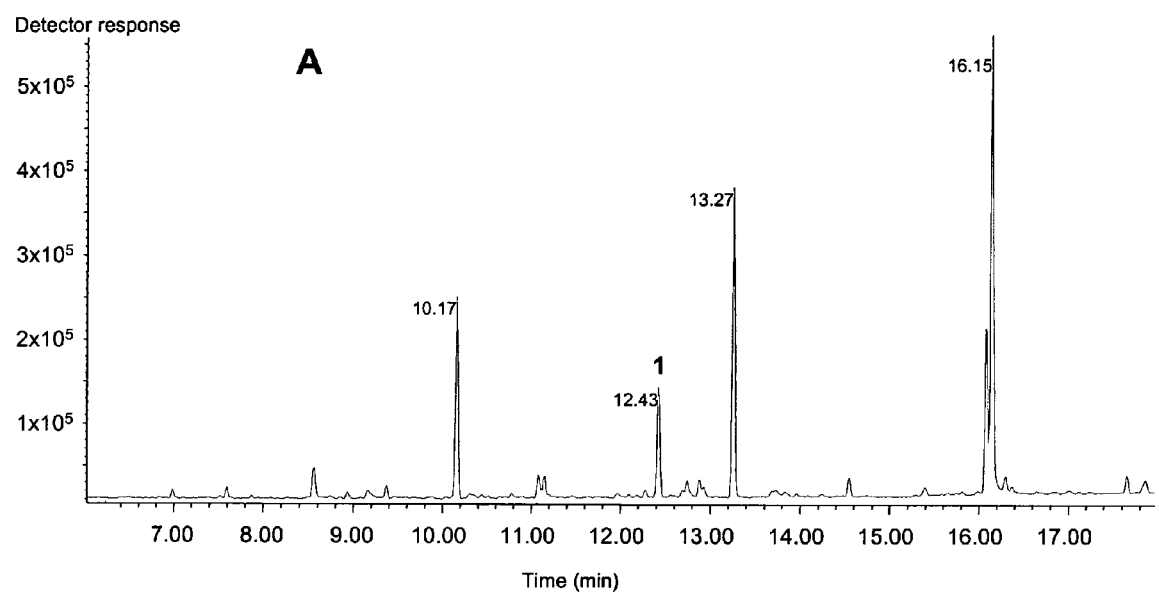
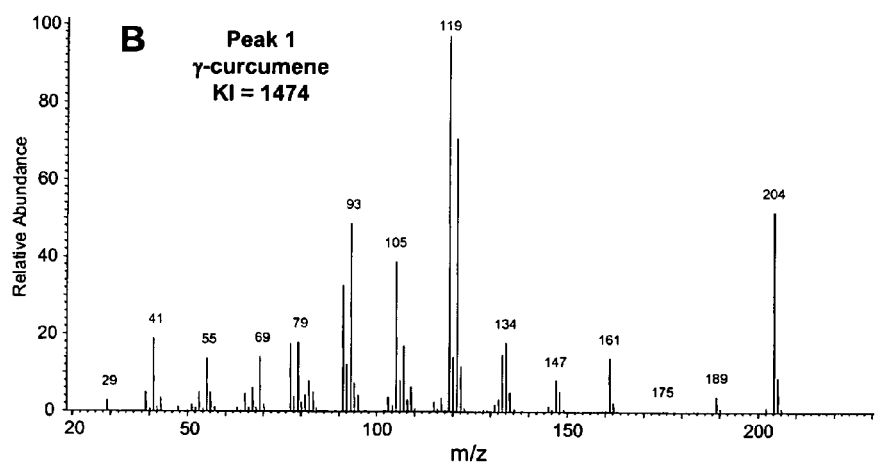

Figure 8.
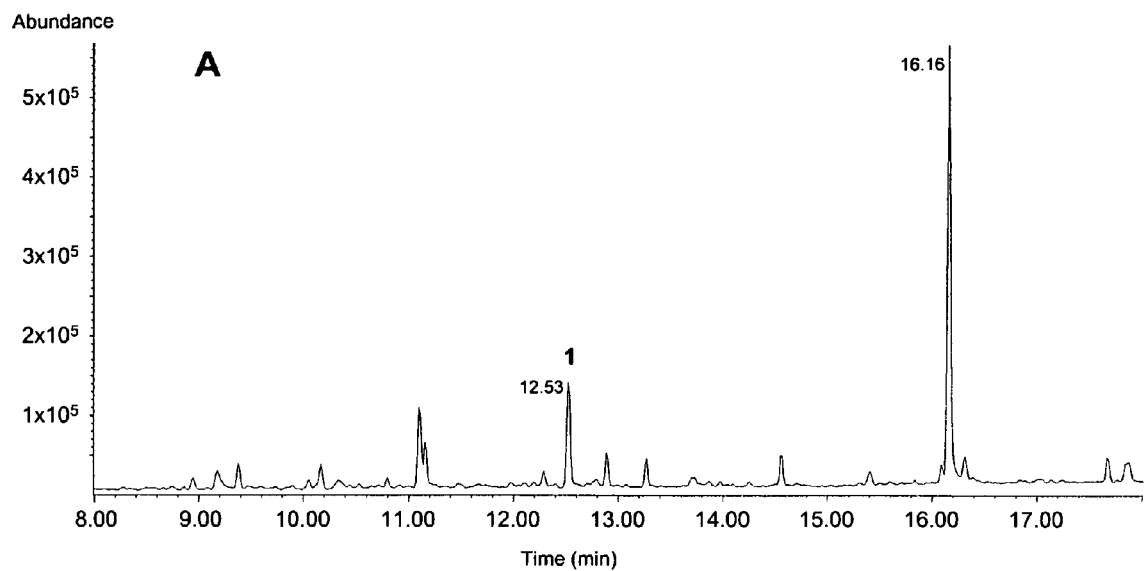
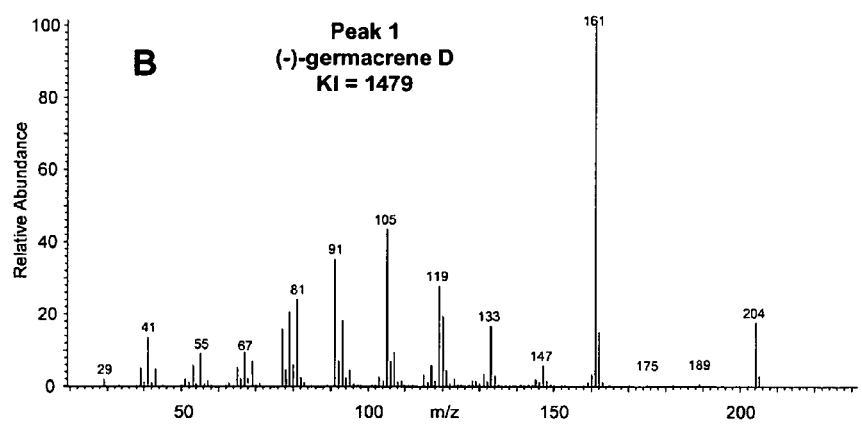

Figure 13

PatTpsA

```
1     ATG GCT GCT TTT ACT GCT AAT GCT GTT GAT ATG AGG CCT CCT GTC    45
1      M   A   A   F   T   A   N   A   V   D   M   R   P   P   V    15

46    ATC ACC ATT CAT CCC CGT TCC AAA GAT ATC TTC TCT CAG TTT TCC    90
16     I   T   I   H   P   R   S   K   D   I   F   S   Q   F   S    30

91    TTG GAC GAT AAG CTT CAG AAG CAG TAC GCA CAA GGA ATT GAA GCT    135
31     L   D   D   K   L   Q   K   Q   Y   A   Q   G   I   E   A    45

136   CTG AAG GAA GAA GCA AGA AGC ATG TTA ATG GCT GCA AAA TCA GCC    180
46     L   K   E   E   A   R   S   M   L   M   A   A   K   S   A    60

181   AAA GTC ATG ATA CTA ATA GAC ACA CTC GAG CGT CTG GGA TTA GGA    225
61     K   V   M   I   L   I   D   T   L   E   R   L   G   L   G    75

226   TAT CAT TTT GAG AAG GAG ATC GAA GAG AAA CTC GAA GCA ATA TAC    270
76     Y   H   F   E   K   E   I   E   E   K   L   E   A   I   Y    90

271   AAG AAG GAA GAT GGT GAC GAC TAT GAT TTG TTC ACT ACT GCG CTT    315
91     K   K   E   D   G   D   D   Y   D   L   F   T   T   A   L    105

316   AGA TTT CGT CTG CTC AGG CAA CAT CAG CGC CGT GTT CCC TGC AGT    360
106    R   F   R   L   L   R   Q   H   Q   R   R   V   P   C   S    120

361   GTT TTT GAT AAG TTT ATG AAC AAA GAG GGC AAG TTT GAG GAA GAA    405
121    V   F   D   K   F   M   N   K   E   G   K   F   E   E   E    135

406   CCC TTG ATT AGT GAT GTG GAG GGA CTA CTG AGT CTG TAT GAT GCA    450
136    P   L   I   S   D   V   E   G   L   L   S   L   Y   D   A    150

451   GCC TAC CTG CAG ATC CAT GGG GAA CAC ATC TTG CAA GAA GCC CTA    495
151    A   Y   L   Q   I   H   G   E   H   I   L   Q   E   A   L    165

496   ATT TTC ACA ACA CAT CAT TTA ACT CGT ATC GAG CCA CAA TTA GAC    540
166    I   F   T   T   H   H   L   T   R   I   E   P   Q   L   D    180

541   GAT CAC TCT CCC CTT AAA CTC AAA CTG AAT CGA GCT TTG GAG TTT    585
181    D   H   S   P   L   K   L   K   L   N   R   A   L   E   F    195

586   CCT TTT TAT CGA GAG ATC CCC ATC ATT TAT GCA CAC TTT TAC ATC    630
196    P   F   Y   R   E   I   P   I   I   Y   A   H   F   Y   I    210

631   TCC GTT TAC GAG AGG GAT GAC TCT AGA GAT GAA GTG CTT CTC AAA    675
211    S   V   Y   E   R   D   D   S   R   D   E   V   L   L   K    225

676   ATG GCA AAA TTG AGC TAC AAT TTC TTG CAA AAT TTG TAC AAG AAA    720
226    M   A   K   L   S   Y   N   F   L   Q   N   L   Y   K   K    240

721   GAG CTT TCT CAA CTC TCC AGG TGG TGG AAT AAA TTA GAA CTA ATA    765
241    E   L   S   Q   L   S   R   W   W   N   K   L   E   L   I    255

766   CCA AAC CTA CCA TAT ATA AGA GAC AGC GTG GCG GGT GCC TAT CTT    810
256    P   N   L   P   Y   I   R   D   S   V   A   G   A   Y   L    270

811   TGG GCT GTA GCA TTA TAT TTC GAA CCT CAA TAT TCT GAT GTC CGA    855
271    W   A   V   A   L   Y   F   E   P   Q   Y   S   D   V   R    285

856   ATG GCC ATT GCC AAA TTA ATA CAA ATT GCT GCT GCA GTA GAT GAT    900
286    M   A   I   A   K   L   I   Q   I   A   A   A   V   D   D    300
```

Figure 13
Cont.

```
901   ACA TAC GAT AAT TAT GCG ACC ATT CGA GAA GCT CAA CTT CTT ACT    945
301    T   Y   D   N   Y   A   T   I   R   E   A   Q   L   L   T    315

946   GAA GCT TTG GAG AGG TTG AAT GTG CAT GAA ATT GAT ACC CTT CCT    990
316    E   A   L   E   R   L   N   V   H   E   I   D   T   L   P    330

991   GAT TAT ATG AAA ATT GTT TAT CGT TTC GTT ATG AGT TGG TCA GAA   1035
331    D   Y   M   K   I   V   Y   R   F   V   M   S   W   S   E    345

1036  GAT TTC GAA CGA GAT GCA ACA ATT AAA GAA CAG ATG CTT GCA ACT   1080
346    D   F   E   R   D   A   T   I   K   E   Q   M   L   A   T    360

1081  CCC TAC TTC AAA GCG GAG ATG AAA AAA CTT GGA AGG GCT TAC AAT   1125
361    P   Y   F   K   A   E   M   K   K   L   G   R   A   Y   N    375

1126  CAA GAG CTG AAG TGG GTT ATG GAA AGG CAA TTG CCT TCA TTT GAA   1170
376    Q   E   L   K   W   V   M   E   R   Q   L   P   S   F   E    390

1171  GAA TAT ATG AAA AAT TCT GAG ATT ACG AGT GGT GTG TAT ATA ATG   1215
391    E   Y   M   K   N   S   E   I   T   S   G   V   Y   I   M    405

1216  TTC ACT GTC ATT TCA CCA TAC TTG AAT TCT GCT ACA CAA AAA AAC   1260
406    F   T   V   I   S   P   Y   L   N   S   A   T   Q   K   N    420

1261  ATT GAT TGG TTG CTG AGT CAA CCT CGT CTC GCT TCA TCC ACT GCC   1305
421    I   D   W   L   L   S   Q   P   R   L   A   S   S   T   A    435

1306  ATA GTT ATG AGA TGC TGC AAT GAC TTG GGC AGC AAT CAA CGC GAG   1350
436    I   V   M   R   C   C   N   D   L   G   S   N   Q   R   E    450

1351  AGC AAG GGT GGA GAA GTG ATG ACT TCC CTG GAT TGC TAC ATG AAA   1395
451    S   K   G   G   E   V   M   T   S   L   D   C   Y   M   K    465

1396  CAA CAT GGT GCA TCA AAG CAA GAA ACC ATA TCT AAA TTT AAA CTA   1440
466    Q   H   G   A   S   K   Q   E   T   I   S   K   F   K   L    480

1441  ATA ATT GAG GAT GAA TGG AAG AAT TTG AAC GAG GAA TGG GCA GCG   1485
481    I   I   E   D   E   W   K   N   L   N   E   E   W   A   A    495

1486  ACC ACT TGT TTG CCA AAA GTA ATG GTG GAG ATA TTT CGC AAC TAC   1530
496    T   T   C   L   P   K   V   M   V   E   I   F   R   N   Y    510

1531  GCA AGA ATT GCA GGT TTC TGT TAC AAA AAC AAT GGA GAT GCT TAT   1575
511    A   R   I   A   G   F   C   Y   K   N   N   G   D   A   Y    525

1576  ACG AGT CCC AAA ATA GTT CAG CAA TGT TTT GAT GCC CTT TTT GTT   1620
526    T   S   P   K   I   V   Q   Q   C   F   D   A   L   F   V    540

1621  AAC CCT CTA CGC ATT TGA      1638
541    N   P   L   R   I   *
```

Figure 14

PatTpsBF2

```
1     ATG GAA TTG AAA AAC CAA AGT GTT GCA ATA ATC TCC AGC AAT GCT    45
1      M   E   L   K   N   Q   S   V   A   I   I   S   S   N   A    15

46    TCT CGC CCA CTT GCG CAT TAT CAT CCA GAC GTA TGG GGA GAT CGT    90
16     S   R   P   L   A   H   Y   H   P   D   V   W   G   D   R    30

91    TTC CTT CTC TAC AAA CCA AAT CCC AGT TCT GAG GCT GGT CAG AAA   135
31     F   L   L   Y   K   P   N   P   S   S   E   A   G   Q   K    45

136   CCA GTT ATT GAA GAG CTG AAA CAG CAA GTG AGA AGC GAG CTG AAG   180
46     P   V   I   E   E   L   K   Q   Q   V   R   S   E   L   K    60

181   GAA GCA TCG AAC GAC TAC ATG CGA CAG CTG AAG ATG GTG GAC GCA   225
61     E   A   S   N   D   Y   M   R   Q   L   K   M   V   D   A    75

226   ATA CAA CGA CTT GGC ATC GAG AGT CTC TTT GAG GAA GAC ATT GAT   270
76     I   Q   R   L   G   I   E   S   L   F   E   E   D   I   D    90

271   AAT GCA TTG AAG AAT CTG TCT GAA AAT TTT GAT GAT TAC TGC AAA   315
91     N   A   L   K   N   L   S   E   N   F   D   D   Y   C   K   105

316   GAT AAG CAT GAT TTG TAT GCC ATT GCT CTT AGC TTT CGC CTT CTC   360
106    D   K   H   D   L   Y   A   I   A   L   S   F   R   L   L   120

361   AGA CAA CAT GGA TAC AGG ATT TCA TGT GAT GTA TTC GAC AAG TTG   405
121    R   Q   H   G   Y   R   I   S   C   D   V   F   D   K   L   135

406   AAG GAT GGC GAA GAT GGA TTC AAA GTT CCC CCT TCA GAT GAA GCG   450
136    K   D   G   E   D   G   F   K   V   P   P   S   D   E   A   150

451   CTT GCA GTT GTA GAG TTG TTA GAG GCC ACG CAT CTA AGA ATC CAT   495
151    L   A   V   V   E   L   L   E   A   T   H   L   R   I   H   165

496   GGA GAA GTT GTG CTT GAT CGT GCC TTT GTT TTC GCC AGG ATT CAC   540
166    G   E   V   V   L   D   R   A   F   V   F   A   R   I   H   180

541   CTT GAA TCG ATT GAA GCA AAT TTG AAT AAT CCA GTC GCG AAA CAA   585
181    L   E   S   I   E   A   N   L   N   N   P   V   A   K   Q   195

586   GTT CAT AAC GCG TTG TAT GGA TAC TCT AAT CGG AGA GGA ATG CAA   630
196    V   H   N   A   L   Y   G   Y   S   N   R   R   G   M   Q   210

631   CAA GTA GAA GCG AGG AAG TAC ATA CCC ATC TAC GAG CAA TAT GCT   675
211    Q   V   E   A   R   K   Y   I   P   I   Y   E   Q   Y   A   225

676   TCT CAT CAT CAA GGC TTG CTC AAA CTT GCT ACG CTG AAT TTT AAC   720
226    S   H   H   Q   G   L   L   K   L   A   T   L   N   F   N   240

721   CTG CAA CAA ACC ATG CAC AAA AGG GAG TTG AGT GAA CTT TCA AGG   765
241    L   Q   Q   T   M   H   K   R   E   L   S   E   L   S   R   255

766   TGG TAT AGA GAT TTA GAA GTT CCA ACA ATG TTA CCA TTT GCT AGA   810
256    W   Y   R   D   L   E   V   P   T   M   L   P   F   A   R   270

811   CAA CGA TTG GTG GAG ACA TAC TTC TGG GAC GCT GGA GTA GTT TTT   855
271    Q   R   L   V   E   T   Y   F   W   D   A   G   V   V   F   285

856   GAA CCA GAA AAT GAT GTT GCC AGG ATG ATT TTA GTC AAA GTG CAA   900
```

901   TGC CTA ATC TCT TTT CTT GAT GAT ACT TTT GAT GCA TAT GGA AGT   945
301   C   L   I   S   F   L   D   D   T   F   D   A   Y   G   S   315

946   TTT GAG GAA CTA CAA CTC TTC ACG GAT GCA ATT AAT ACA TGG GAT   990
316   F   E   E   L   Q   L   F   T   D   A   I   N   T   W   D   330

991   GTT TCA TGT TTA GAT CAA CTT CCA GAT TAT ATG AAG ATA ATT TAC   1035
331   V   S   C   L   D   Q   L   P   D   Y   M   K   I   I   Y   345

1036  AAA GCC CTT TTG GGA GTG TTT GAA GTA ATT GAG AAA CTA ATG ATC   1080
346   K   A   L   L   G   V   F   E   V   I   E   K   L   M   I   360

1081  AAA CAA GGA ACA TTG TAT CGT CTC AAC TAT GCA AAA GAA GCG ATG   1125
361   K   Q   G   T   L   Y   R   L   N   Y   A   K   E   A   M   375

1126  AAA ATA GTG GTG GGA GGT TAC TTT GTT GAG GCT AAA TGG AGG GAA   1170
376   K   I   V   V   G   G   Y   F   V   E   A   K   W   R   E   390

1171  GAA AAG AGC AAA CCC ACG ACG CAA GAG TAC ATG CAG GTA GCA ACA   1215
391   E   K   S   K   P   T   T   Q   E   Y   M   Q   V   A   T   405

1216  AAG AGT GCA GGA TAT ATG ACT CTT ATT ATA ACA TCA TTT CTT GGA   1260
406   K   S   A   G   Y   M   T   L   I   I   T   S   F   L   G   420

1261  ATG GAA GCA AAT ATT GCC ACC AAA GAA GCC TTC GAT TGG GTG CTT   1305
421   M   E   A   N   I   A   T   K   E   A   F   D   W   V   L   435

1306  TCT GAG CCT GAT GTT ATG AAA GCT GCA ATA ACT CTT GCC AGG CTC   1350
436   S   E   P   D   V   M   K   A   A   I   T   L   A   R   L   450

1351  ACC AAT GAT ATC GTC GGA ATT GAG CTC GAG AAA GAA AGA AAG CAT   1395
451   T   N   D   I   V   G   I   E   L   E   K   E   R   K   H   465

1396  ATA GCT ACA GCA GTG GAA GTG TAC GAG GAC GAG CAT AAA TTG TCC   1440
466   I   A   T   A   V   E   V   Y   E   D   E   H   K   L   S   480

1441  ATG CAA GAG GCC ATG GTT GAA ATC AAG AAT CAA ATC GAG TCG GGA   1485
481   M   Q   E   A   M   V   E   I   K   N   Q   I   E   S   G   495

1486  TGG AAG ACC ATA AAT GAG GCG TTT CTT AGA CCA ACT AAA TTT CCA   1530
496   W   K   T   I   N   E   A   F   L   R   P   T   K   F   P   510

1531  ACA CCT ATA CTT TAT CGT ATA CTC AAT TAC TGC AGA GTT CTT GAG   1575
511   T   P   I   L   Y   R   I   L   N   Y   C   R   V   L   E   525

1576  GTT ATT TAC GAC AAG AGC GAT CGC TAC ACA CAT GTG GAT CCT GCA   1620
526   V   I   Y   D   K   S   D   R   Y   T   H   V   D   P   A   540

1621  TTG CAA GAC ATC ATC AAG CAA CTA TAT ATT CAC CCT ATT CCA TAG   1665
541   L   Q   D   I   I   K   Q   L   Y   I   H   P   I   P   *
```

Figure 15

PatTpsCF2

```
1    ATG GCT GTA CAA ATC TCC GAA ACT GTT CGC CCT TTC GCC AAT TTT    45
1     M   A   V   Q   I   S   E   T   V   R   P   F   A   N   F    15

46   TCT CCC AAT CCC AGC TTG TGG GGT GAT CAA TTC ATC AAC CAC AAA    90
16    S   P   N   P   S   L   W   G   D   Q   F   I   N   H   K    30

91   TCT AAA ACT CAG CAA ATA TCG AGG ATA TAT TTG GAG GAA ATT GAA   135
31    S   K   T   Q   Q   I   S   R   I   Y   L   E   E   I   E    45

136  GGG TTG AAA AAT GAA GTA AAG TGT ATG CTA ACA AGT ACC CCA GAG   180
46    G   L   K   N   E   V   K   C   M   L   T   S   T   P   E    60

181  GGA AAG ATG GCG GAC ACC GTC AAC CTG ATC GAC ACA CTC GAG CGC   225
61    G   K   M   A   D   T   V   N   L   I   D   T   L   E   R    75

226  CTA GGG GTA TCG TAT CAT TTC GAA AAG GAA ATC GAA GAG AAG ATG   270
76    L   G   V   S   Y   H   F   E   K   E   I   E   E   K   M    90

271  AAA CAC TTA TTC AAT CTG ATC AAA GCG GAT AAC TAT AAA GAT CAT   315
91    K   H   L   F   N   L   I   K   A   D   N   Y   K   D   H   105

316  GAA GGC TGT GAT TTG TAT ACT GAT GCT CTT CAT TTT CGA TTA TTC   360
106   E   G   C   D   L   Y   T   D   A   L   H   F   R   L   F   120

361  AGG CAG CAT GGT TAC CCT ATA TCT TCT GGG ATT TTT AAC AAA TGG   405
121   R   Q   H   G   Y   P   I   S   S   G   I   F   N   K   W   135

406  ATG GAT GGG AAT GGA AAA TTC AAG GAG AGC ATT AAG AGT GAT GCA   450
136   M   D   G   N   G   K   F   K   E   S   I   K   S   D   A   150

451  AAG GGT TTG TTG AGC TTG TAT GAA GCA TGC TGT TTG AGA ACA CAT   495
151   K   G   L   L   S   L   Y   E   A   C   C   L   R   T   H   165

496  GGA GAC ACC CTA CTC GAC GAA GCC CTT GTT TTT GCT ACG GCC AGT   540
166   G   D   T   L   L   D   E   A   L   V   F   A   T   A   S   180

541  CTG AAA TCC ATG GCA GCA AAC CTT GCG TCA CCC CTA AGG AAA CAG   585
181   L   K   S   M   A   A   N   L   A   S   P   L   R   K   Q   195

586  GTT GAG CAT GCC CTC TTC CAG CAC TTG CAT TTT GGC ATT CCA AGA   630
196   V   E   H   A   L   F   Q   H   L   H   F   G   I   P   R   210

631  GTC GAA GCA CGA CAC TTC ATC ACC TTC TAC GAA GAG GAA GAG CAC   675
211   V   E   A   R   H   F   I   T   F   Y   E   E   E   E   H   225

676  AAG AAT GAG ATG CTG CTT AGG TTC GCC AAA TTG GAC TTT AAT GCA   720
226   K   N   E   M   L   L   R   F   A   K   L   D   F   N   A   240

721  TTG CAA GCA CTG CAC AAA GAG GAG CTG AGT GAA ATC AGC AAG TGG   765
241   L   Q   A   L   H   K   E   E   L   S   E   I   S   K   W   255

766  TGG AAA GAT TTG GAT CTC ATC TCG AAA CTT CCA TAT GCA AGA GAC   810
256   W   K   D   L   D   L   I   S   K   L   P   Y   A   R   D   270

811  AGG GTG GTA GAG TCT TAC TTT TGG GCA GTG GGA GTG TAC TAT CAA   855
271   R   V   V   E   S   Y   F   W   A   V   G   V   Y   Y   Q   285

856  CCC AAG TAC TCT CGT GCC CGT ATT ATG CTC ACT AAA ACC ATT GCC   900
```

**Figure 15
Cont.**

```
286    P   K   Y   S   R   A   R   I   M   L   T   K   T   I   A    300
901   ATG ACG GCT ATA TTG GAT GAC ACC TAT GAC TCT TAT GGT ACA CTT   945
301    M   T   A   I   L   D   D   T   Y   D   S   Y   G   T   L   315

946   GAA GAA CTT GAT GTT CTC ACA AAG GCA ATT GAG AGG TGG GAT ATC   990
316    E   E   L   D   V   L   T   K   A   I   E   R   W   D   I   330

991   AAA GAA ATT AAT GGA CTC CCA GAG TAC ATC AAA GGA TTC TAT AAA  1035
331    K   E   I   N   G   L   P   E   Y   I   K   G   F   Y   K   345

1036  CAG GTG CTG AAA CTC TAT CAG CAA TTA GAG GAA GAA TTA GCA AAG  1080
346    Q   V   L   K   L   Y   Q   Q   L   E   E   E   L   A   K   360

1081  GAA GGA AGA TCT TAT GCT GTA TAC TAT GCA ATA GAA GCT TGT AAG  1125
361    E   G   R   S   Y   A   V   Y   Y   A   I   E   A   C   K   375

1126  GAA TTG GCG AGG AGC TAC GCT GTG GAG GCG AAG TGG TTC AAG AAA  1170
376    E   L   A   R   S   Y   A   V   E   A   K   W   F   K   K   390

1171  GGG TAC TTG CCC GGA TTT GAG GAG TAC CTA ATC AAT TCT CTC GTC  1215
391    G   Y   L   P   G   F   E   E   Y   L   I   N   S   L   V   405

1216  ACC TCC ACG GCT GGC TAT CTC AAT ATA ATC TCG TTT TTT GGC GTG  1260
406    T   S   T   A   G   Y   L   N   I   I   S   F   F   G   V   420

1261  GAA TCT GTA ACC AAG GAA GAT TTT GAA TGG TTT AGC AAG AAG CCT  1305
421    E   S   V   T   K   E   D   F   E   W   F   S   K   K   P   435

1306  AGA ATC GCT GTA GCC ACT CAG ATA ATT ACA AGA GTT ATC GAT GAC  1350
436    R   I   A   V   A   T   Q   I   I   T   R   V   I   D   D   450

1351  ATT GCA ACT TAT GAG GTA GAG AAG GAG AAG GGT CAG AGT GCC ACA  1395
451    I   A   T   Y   E   V   E   K   E   K   G   Q   S   A   T   465

1396  GGA ATA GAT TGC TAC ATG AAG GAA CAT GGG GTG AGC AAA GAG AAG  1440
466    G   I   D   C   Y   M   K   E   H   G   V   S   K   E   K   480

1441  GCA ATG CAG AGA TTC TAT GAA ATG AGT ACC AAT GCA TGG AAG GAT  1485
481    A   M   Q   R   F   Y   E   M   S   T   N   A   W   K   D   495

1486  ATT AAT GAG GAA GGC CTC AGT TGG CCA TCT TCT TTT TCC AGG GAT  1530
496    I   N   E   E   G   L   S   W   P   S   S   F   S   R   D   510

1531  ATT TTC GTC CAA CTC CGA AAT TTT AGT CGC ATG GTT GAT GTT ACC  1575
511    I   F   V   Q   L   R   N   F   S   R   M   V   D   V   T   525

1576  TAT GGC AAA AAT GAA GAT GGA TAC TCC AAA CCC GAA AAG ATT CTC  1620
526    Y   G   K   N   E   D   G   Y   S   K   P   E   K   I   L   540

1621  AAG CCA CTT ATC ATT GCT CTG TTT GTT GAT CAG ATC AAG CTT TAA  1665
541    K   P   L   I   I   A   L   F   V   D   Q   I   K   L   *
```

Figure 16

```
PatTpsB15

1     ATG GAT TTG AAT GAA ATC ACC TCT TCA TCT CGT CCT CTC GCA AAT    45
1      M   D   L   N   E   I   T   S   S   S   R   P   L   A   N    15

46    TAT CAC CCA AAT GTG TGG GGA GAC CGT TTC CTT CTG CAT GAA CCA    90
16     Y   H   P   N   V   W   G   D   R   F   L   L   H   E   P    30

91    GAA TTC ACT TGC CAG GCT GGT GAG AAA CAA CTA GTT GAA GAG CTG   135
31     E   F   T   C   Q   A   G   E   K   Q   L   V   E   E   L    45

136   AAA GAG GAA GTG AGA AGG GAG CTG AAG GAA GCG TCG AAC GAC TAC   180
46     K   E   E   V   R   R   E   L   K   E   A   S   N   D   Y    60

181   CTT CGA CAG CTG AAG ATG GTG GAC GCA ATA CAA CGA CTA GGC ATC   225
61     L   R   Q   L   K   M   V   D   A   I   Q   R   L   G   I    75

226   GAG TAT CTC TTT GAG GAA GAG ATT GAT GAA GCT CTG AGA AAT CTG   270
76     E   Y   L   F   E   E   E   I   D   E   A   L   R   N   L    90

271   TTG GCA AAA TTC GAG AAT TAT TGC AAG GAT AAT CAT GAT ATG TAC   315
91     L   A   K   F   E   N   Y   C   K   D   N   H   D   M   Y   105

316   GCC ACT GCT CTT AGC TTT CGC CTT CTC AGA CAA CAC GGA TAC AAG   360
106    A   T   A   L   S   F   R   L   L   R   Q   H   G   Y   K   120

361   GTT TCA TGT GAA GTT TTT GAC AAG TTT AAG GAT GGG GAA GAT GGA   405
121    V   S   C   E   V   F   D   K   F   K   D   G   E   D   G   135

406   TTC AAG GTG GAA GAA GTG ATG GCA GTT CTC GAG TTG TTT GAG GCT   450
136    F   K   V   E   E   V   M   A   V   L   E   L   F   E   A   150

451   ACA CAT ATG AGA ATT CAT GGA GAA GAT GTG CTC GAT CAA GCC TTT   495
151    T   H   M   R   I   H   G   E   D   V   L   D   Q   A   F   165

496   GTT TTC ACA AGG AAT TAC CTT CAA TCA ATT CAC GCA ACC TTG AGT   540
166    V   F   T   R   N   Y   L   Q   S   I   H   A   T   L   S   180

541   AAT CCA ATT GCT AAA CAA GTT CAC AAC GCA TTG AAT GGA TAC TCT   585
181    N   P   I   A   K   Q   V   H   N   A   L   N   G   Y   S   195

586   TGT CGG AGA GGA ATG CCA CGA ATC GAA GCG AGG AAG TAT ATA CCC   630
196    C   R   R   G   M   P   R   I   E   A   R   K   Y   I   P   210

631   ATC TAC GAG GAA TAC GGT TGT CAC CAT AAA GCC TTG CTC AAA CTT   675
211    I   Y   E   E   Y   G   C   H   H   K   A   L   L   K   L   225

676   GCT AAG CTC GAT TTC AAT CTA CTT CAA TCT ATG CAC AAA AGG GAG   720
226    A   K   L   D   F   N   L   L   Q   S   M   H   K   R   E   240

721   TTG ACT CAA CTT TAT AGG TGG TGG AAA GAT TTG GAA ATG CCA ACA   765
241    L   T   Q   L   Y   R   W   W   K   D   L   E   M   P   T   255

766   AAG CTA CCG TAC ATA AGA GAT CGA TTG GTG GAG ACA TAC TTT TGG   810
256    K   L   P   Y   I   R   D   R   L   V   E   T   Y   F   W   270

811   GAC ATG GGG TTT TAT TTT GAA CCA CAA TAT GCT CTA GCT AGA AAT   855
271    D   M   G   F   Y   F   E   P   Q   Y   A   L   A   R   N   285

856   ATC TTA GTC AAA GTA CAA TGT TTG GTG TCT ATT TTC GAT GAC ACT   900
286    I   L   V   K   V   Q   C   L   V   S   I   F   D   D   T   300
```

Figure 16
Cont.

```
 901  TTT GAT GCA TAT GGT GCT TTT AAG GAA TTA CAA CTC TTC AAA GAT   945
 301   F   D   A   Y   G   A   F   K   E   L   Q   L   F   K   D   315

946  GCC ATT GAT AGA TGG AGT ATC TCA TGC TTA GAT GAA CTT CCA GAG   990
 316   A   I   D   R   W   S   I   S   C   L   D   E   L   P   E   330

991  TAT ATG CAG ATA ATC TAC AAA CTG GTT TTG GAC GTG TTT GAA GAA  1035
 331   Y   M   Q   I   I   Y   K   L   V   L   D   V   F   E   E   345

1036  ATT GAG AGT CAT ATG ATC AAA CAA GGA ACA TCG TAT CGT CTG GAC  1080
 346   I   E   S   H   M   I   K   Q   G   T   S   Y   R   L   D   360

1081  TAT GCA AGA GAA GCG ATA AAA ATT GTG ATT GGA GGT TAC TTT GAT  1125
 361   Y   A   R   E   A   I   K   I   V   I   G   G   Y   F   D   375

1126  GAG GCA AAA TGG AGG GAA GAA GAG TAC AAG CCA AGA ATG GAA GAG  1170
 376   E   A   K   W   R   E   E   E   Y   K   P   R   M   E   E   390

1171  TAC ATG AAA GTA GCT ACA AAG AGT GCA GTC TAC TTA ACT CTA ATC  1215
 391   Y   M   K   V   A   T   K   S   A   V   Y   L   T   L   I   405

1216  ATA GTA TCA TTT GTA GGG ATG AAA AAT GAC ATT GCC ACC CCA CAA  1260
 406   I   V   S   F   V   G   M   K   N   D   I   A   T   P   Q   420

1261  GCC TTC CAA TGG GTC CTT TCT GAA CCT CAA ATT ATT ACA GCT TCT  1305
 421   A   F   Q   W   V   L   S   E   P   Q   I   I   T   A   S   435

1306  TTA GCT CTT GCC AGG CTC TCC AAT GAT CTC GTG GGC ATT GAG TTT  1350
 436   L   A   L   A   R   L   S   N   D   L   V   G   I   E   F   450

1351  GAG AAA GAG AGA AAG CAT ATA GCG ACA GCA GTG GAG TTG TAC GAG  1395
 451   E   K   E   R   K   H   I   A   T   A   V   E   L   Y   E   465

1396  GAA GAG CAT AAA GTG TCA AAA GAA GAG GCT GTG TTG GAA TTG AGG  1440
 466   E   E   H   K   V   S   K   E   E   A   V   L   E   L   R   480

1441  CAT GAA ACA GAG TCG GCA TGG AAG GAA ATT AAT GAG GCG TTG TTA  1485
 481   H   E   T   E   S   A   W   K   E   I   N   E   A   L   L   495

1486  GAG CCA ACT ACA TTT GCG ACC CCA ATT CTT GAT CGT ATA CTT AAT  1530
 496   E   P   T   T   F   A   T   P   I   L   D   R   I   L   N   510

1531  TCC GCC CGA GTA CTT GAA GTT TTT TAC GAC AAG ACC GAC CGC TAC  1575
 511   S   A   R   V   L   E   V   F   Y   D   K   T   D   R   Y   525

1576  ACA CAT GTG GAT CTT GAA TTG CAG AAT ATC ATC GCC CAA CTA TAC  1620
 526   T   H   V   D   L   E   L   Q   N   I   I   A   Q   L   Y   540

1621  ATT CAC CCT ATT CCT TAA  1638
 541   I   H   P   I   P   *
```

Figure 17

PatTps177

```
1    ATG GAG TTG TAT GCC CAA AGT GTT GGA GTG GGT GCT GCT TCT CGT    45
1     M   E   L   Y   A   Q   S   V   G   V   G   A   A   S   R    15

46   CCT CTT GCG AAT TTT CAT CCA TGT GTG TGG GGA GAC AAA TTC ATT    90
16    P   L   A   N   F   H   P   C   V   W   G   D   K   F   I    30

91   GTC TAC AAC CCA CAA TCA TGC CAG GCT GGA GAG AGA GAA GAG GCT   135
31    V   Y   N   P   Q   S   C   Q   A   G   E   R   E   E   A    45

136  GAG GAG CTG AAA GTG GAG CTG AAA AGA GAG CTG AAG GAA GCA TCA   180
46    E   E   L   K   V   E   L   K   R   E   L   K   E   A   S    60

181  GAC AAC TAC ATG CGG CAA CTG AAA ATG GTG GAT GCA ATA CAA CGA   225
61    D   N   Y   M   R   Q   L   K   M   V   D   A   I   Q   R    75

226  TTA GGC ATT GAC TAT CTT TTT GTG GAA GAT GTT GAT GAA GCT TTG   270
76    L   G   I   D   Y   L   F   V   E   D   V   D   E   A   L    90

271  AAG AAT CTG TTT GAA ATG TTT GAT GCT TTC TGC AAG AAT AAT CAT   315
91    K   N   L   F   E   M   F   D   A   F   C   K   N   N   H   105

316  GAC ATG CAC GCC ACT GCT CTC AGC TTT CGC CTT CTC AGA CAA CAT   360
106   D   M   H   A   T   A   L   S   F   R   L   L   R   Q   H   120

361  GGA TAC AGA GTT TCA TGT GAA GTT TTT GAA AAG TTT AAG GAT GGC   405
121   G   Y   R   V   S   C   E   V   F   E   K   F   K   D   G   135

406  AAA GAT GGA TTT AAG GTT CCA AAT GAG GAT GGA GCG GTT GCA GTC   450
136   K   D   G   F   K   V   P   N   E   D   G   A   V   A   V   150

451  CTT GAA TTC TTC GAA GCC ACG CAT CTC AGA GTC CAT GGA GAA GAC   495
151   L   E   F   F   E   A   T   H   L   R   V   H   G   E   D   165

496  GTC CTT GAT AAT GCT TTT GAC TTC ACT AGG AAC TAC TTG GAA TCA   540
166   V   L   D   N   A   F   D   F   T   R   N   Y   L   E   S   180

541  GTC TAT GCA ACT TTG AAC GAT CCA ACC GCG AAA CAA GTC CAC AAC   585
181   V   Y   A   T   L   N   D   P   T   A   K   Q   V   H   N   195

586  GCA TTG AAT GAG TTC TCT TTT CGA AGA GGA TTG CCA CGC GTG GAA   630
196   A   L   N   E   F   S   F   R   R   G   L   P   R   V   E   210

631  GCA AGG AAG TAC ATA TCA ATC TAC GAG CAA TAC GCA TCT CAT CAC   675
211   A   R   K   Y   I   S   I   Y   E   Q   Y   A   S   H   H   225

676  AAA GGC TTG CTC AAA CTT GCT AAG CTG GAT TTC AAC TTG GTA CAA   720
226   K   G   L   L   K   L   A   K   L   D   F   N   L   V   Q   240

721  GCT TTG CAC AGA AGG GAG CTG AGT GAA GAT TCT AGG TGG TGG AAG   765
241   A   L   H   R   R   E   L   S   E   D   S   R   W   W   K   255

766  ACT TTA CAA GTG CCC ACA AAG CTA TCA TTC GTT AGA GAT CGA TTG   810
256   T   L   Q   V   P   T   K   L   S   F   V   R   D   R   L   270

811  GTG GAG TCC TAC TTC TGG GCT TCG GGA TCT TAT TTC GAA CCG AAT   855
271   V   E   S   Y   F   W   A   S   G   S   Y   F   E   P   N   285
```

**Figure 17
Cont.**

```
856    TAT TCG GTA GCT AGG ATG ATT TTA GCA AAA GGG CTG GCT GTA TTA    900
286     Y   S   V   A   R   M   I   L   A   K   G   L   A   V   L    300

901    TCT CTT ATG GAT GAT GTG TAT GAT GCA TAT GGT ACT TTT GAG GAA    945
301     S   L   M   D   D   V   Y   D   A   Y   G   T   F   E   E    315

946    TTA CAA ATG TTC ACA GAT GCA ATC GAA AGG TGG GAT GCT TCA TGT    990
316     L   Q   M   F   T   D   A   I   E   R   W   D   A   S   C    330

991    TTA GAT AAA CTT CCA GAT TAC ATG AAA ATA GTA TAC AAG GCC CTT    1035
331     L   D   K   L   P   D   Y   M   K   I   V   Y   K   A   L    345

1036   TTG GAT GTG TTT GAG GAA GTT GAC GAG GAG TTG ATC AAG CTA GGC    1080
346     L   D   V   F   E   E   V   D   E   E   L   I   K   L   G    360

1081   GCA CCA TAT CGA GCC TAC TAT GGA AAA GAA GCC ATG AAA TAC GCC    1125
361     A   P   Y   R   A   Y   Y   G   K   E   A   M   K   Y   A    375

1126   GCG AGA GCT TAC ATG GAA GAG GCC CAA TGG AGG GAG CAA AAG CAC    1170
376     A   R   A   Y   M   E   E   A   Q   W   R   E   Q   K   H    390

1171   AAA CCC ACA ACC AAG GAG TAT ATG AAG CTG GCA ACC AAG ACA TGT    1215
391     K   P   T   T   K   E   Y   M   K   L   A   T   K   T   C    405

1216   GGC TAC ATA ACT CTA ATA ATA TTA TCA TGT CTT GGA GTG GAA GAG    1260
406     G   Y   I   T   L   I   I   L   S   C   L   G   V   E   E    420

1261   GGC ATT GTG ACC AAA GAA GCC TTC GAT TGG GTG TTC TCC CGA CCT    1305
421     G   I   V   T   K   E   A   F   D   W   V   F   S   R   P    435

1306   CCT TTC ATC GAG GCT ACA TTA ATC ATT GCC AGG CTC GTC AAT GAT    1350
436     P   F   I   E   A   T   L   I   I   A   R   L   V   N   D    450

1351   ATT ACG GGA CAC GAG TTT GAG AAA AAA CGA GAG CAC GTT CGC ACT    1395
451     I   T   G   H   E   F   E   K   K   R   E   H   V   R   T    465

1396   GCA GTA GAA TGC TAC ATG GAA GAG CAC AAA GTG GGG AAG CAA GAG    1440
466     A   V   E   C   Y   M   E   E   H   K   V   G   K   Q   E    480

1441   GTG GTG TCT GAA TTC TAC AAC CAA ATG GAG TCA GCA TGG AAG ACA    1485
481     V   V   S   E   F   Y   N   Q   M   E   S   A   W   K   T    495

1486   GTG AAC GAG GGG TTC CTC AGA CCA GTT GAA TTT CCA ATC CCT CTA    1530
496     V   N   E   G   F   L   R   P   V   E   F   P   I   P   L    510

1531   CTT TAT CTT ATT CTC AAT TCA GTC CGA ACA CTT GAG GTT ATT TAC    1575
511     L   Y   L   I   L   N   S   V   R   T   L   E   V   I   Y    525

1576   AAA GAG GGC GAT TCG TAT ACA CAC GTG GGT CCT GCA ATG CAA AAC    1620
526     K   E   G   D   S   Y   T   H   V   G   P   A   M   Q   N    540

1621   ATC ATC AAG CAG TTG TAC CTT CAC CCT GTT CCA TAT TAA    1659
541     I   I   K   Q   L   Y   L   H   P   V   P   Y   *
```

Figure 18

PatTpsC16

```
1     ATT ACC ATG GTG TCT ATA TTG GAT GAC ACC TTT GAC TCT TAT GGT    45
1      I   T   M   V   S   I   L   D   D   T   F   D   S   Y   G    15

46    ACA CTT CAA GAA CTT GAT CTT CTC ACC AAG GCA ATT GAG AGG TGG    90
16     T   L   Q   E   L   D   L   L   T   K   A   I   E   R   W    30

91    GAT ATT AAG GAA ATT AAT GGA CTC CCA GAG TAC ATC AAG GGA TTC   135
31     D   I   K   E   I   N   G   L   P   E   Y   I   K   G   F    45

136   TAT AGA GTG TTG TTG GAA CTC CAT CAG CAA TTT CAG GAA GAA TTA   180
46     Y   R   V   L   L   E   L   H   Q   Q   F   Q   E   E   L    60

181   GAA AAG GAA GGA AGT TCT TAT GCA GTA CAT TAT GCA ATA GAA GCT   225
61     E   K   E   G   S   S   Y   A   V   H   Y   A   I   E   A    75

226   TAT AAG GAT TTG GCG AGG AGT TAC GAT GTG GAG GCA AAG TGG TTC   270
76     Y   K   D   L   A   R   S   Y   D   V   E   A   K   W   F    90

271   ATG AAA GGG TAC TTG CCC GGA TTT GAG GAG TAC CTA AGG ATT TCT   315
91     M   K   G   Y   L   P   G   F   E   E   Y   L   R   I   S   105

316   CTC ATC ACC TCC ACC GCC GGC TAT CTC AAT GTA ACC TTG CTC TTG   360
106    L   I   T   S   T   A   G   Y   L   N   V   T   L   L   L   120

361   GGC ATG GAC TCT GTA ACC AAG GAA GAT TTT GAA TGG TTC AGC AAG   405
121    G   M   D   S   V   T   K   E   D   F   E   W   F   S   K   135

406   AAC CCT AGA ATC GCT GTA GCC ACT CAG ATG ATT ACC CGT GTC ATC   450
136    N   P   R   I   A   V   A   T   Q   M   I   T   R   V   I   150

451   GAT GAC ATT GCC ACT TAT GAG GTA GAG AAA GGG AGG GGT CAG ATT   495
151    D   D   I   A   T   Y   E   V   E   K   G   R   G   Q   I   165

496   GCA ACA GGA ATA GAG TGC TAC ATG AAG GAA TAT GGG GTG AGC AAA   540
166    A   T   G   I   E   C   Y   M   K   E   Y   G   V   S   K   180

541   GAG GAG GCA ATG GAG AGA TTC TAT GAA ATG GGT ACA AAT GCA TGG   585
181    E   E   A   M   E   R   F   Y   E   M   G   T   N   A   W   195

586   AAG GAT GTT AAT GAG GTG GGT ATA AGT TGG CCA TCT TCT TCT TCC   630
196    K   D   V   N   E   V   G   I   S   W   P   S   S   S   S   210

631   AGG GAT ATT TTC GTC CAA CTC CGA AAT TTT AAC CGC CTA ATT GAT   675
211    R   D   I   F   V   Q   L   R   N   F   N   R   L   I   D   225

676   GTT ACC TAC GGT AAA AAT GAA GAT GGA TAC TCC AAA CCC GAA AAG   720
226    V   T   Y   G   K   N   E   D   G   Y   S   K   P   E   K   240

721   ATT CTC AAG CCA CAT ATC ATT GCT CTG TTT GTT GAT CAA ATC AAG   765
241    I   L   K   P   H   I   I   A   L   F   V   D   Q   I   K   255

766   CTT TAA
256    L   *
```

SESQUITERPENE SYNTHASES FROM PATCHOULI

CROSS-REFERENCE TO RELATED APPLICATIONS

This application is a continuation of International application PCT/IB2004/003836 filed Nov. 19, 2004, and claims the benefit of each of International application No. PCT/IB03/06459 filed Dec. 9, 2003 and U.S. provisional application No. 60/525,512 filed Nov. 26, 2003, the entire content of each of which is expressly incorporated herein by reference thereto.

TECHNICAL FIELD

The present invention relates to sesquiterpene synthases from Patchouli (*Pogostemon cablin*) plants, and methods of their production and use. In one embodiment, the invention provides nucleic acids comprising a nucleotide sequence as described herein that encodes for at least one sesquiterpene synthase. In a further embodiment, the invention also provides for sesquiterpene synthases and methods of making and using these enzymes. For example, sesquiterpene synthases of the invention may be used to convert farnesyl-pyrophosphate to various sesquiterpenes including patchoulol, γ-curcumene and other germacrane-type sesquiterpenes.

BACKGROUND OF THE INVENTION

Terpenoids or terpenes represent a family of natural products found in most organisms (bacteria, fungi, animal, plants). Terpenoids are made up of five carbon units called isoprene units. They can be classified by the number of isoprene units present in their structure: monoterpenes (C10), sesquiterpenes (C15), diterpenes (C20), triterpenes (C30), tetraterpenes (C40) and polyterpenes (Cn). The plant kingdom contains the highest diversity of monoterpenes and sesquiterpenes.

The monoterpenes and sesquiterpenes are the most structurally diverse isoprenoids. They are usually volatile compounds and are mostly found in plants were they play a role in defense against pathogens and herbivores attacks, in pollinator attraction and in plant-plant communication.

Some plants, known as aromatic plants or essential-oil-plants, accumulate large amounts of monoterpenes and sesquiterpenes in their leaves. In these plants, the terpenes are often synthesized and accumulated in specialized anatomical structures, glandular trichomes or secretory cavities, localized on the leaves and stems surface. Classical examples of such plants are members from the Lamiaceae family such as lavender, mint, sage, basil and patchouli.

Monoterpene and sesquiterpene accumulating plants have been of interest for thousands of years because of their flavor and fragrance properties and their cosmetic, medicinal and anti-microbial effects. The terpenes accumulated in the plants can be extracted by different means such as steam distillation that produces the so-called essential oil containing the concentrated terpenes. Such natural plant extracts are important components for the flavor and perfumery industry.

Many sesquiterpene compounds are used in perfumery (e.g. patchoulol, nootkatone, santalol, vetivone, sinensal) and many are extracted from plants. The price and availability of the plant natural extracts is dependent on the abundance, the oil yield and the geographical origin of the plants. Because of the complexity of their structure, production of individual terpene molecules by chemical synthesis is often limited by the cost of the process and may not always be chemically or financially feasible. The recent progress in understanding terpene biosynthesis in plants and the use of modern biotechnology techniques opens new opportunities for the production of terpene molecules. The use of biocatalysts for the production of terpenes requires a clear understanding of the biosynthesis of terpenes and the isolation of the genes encoding enzymes involved in specific biosynthetic steps.

The biosynthesis of terpenes in plants has been extensively studied. The common five-carbon precursor to all terpenes is isopentenyl pyrophosphate (IPP). Most of the enzymes catalyzing the steps leading to IPP have been cloned and characterized. Two distinct pathways for IPP biosynthesis coexist in the plants. The mevalonate pathway is found in the cytosol and endoplasmic reticulum and the non-mevalonate pathway (or deoxyxylulose (DXP) pathway) is found in the plastids. In the next step IPP is repetitively condensed by prenyl transferases to form the acyclic prenyl pyrophosphate terpene precursors for each class of terpenes, e.g. geranyl-pyrophosphate (GPP) for the monoterpenes, farnesyl-pyrophosphate (FPP) for the sesquiterpenes, geranylgeranyl-pyrophosphate (GGPP) for the diterpenes. These precursors serve as substrate for the terpene synthases or cyclases, which are specific for each class of terpene, e.g. monoterpene, sesquiterpene or diterpene synthases. Terpene synthases catalyze complex multiple step cyclizations to form the large diversity of carbon skeleton of the terpene compounds. The reaction starts with the ionization of the diphosphate group to form an allylic cation. The substrate undergoes then isomerizations and rearrangements that are controlled by the active site of the enzyme. The product can be acyclic, or cyclic with one or multiple rings. The reaction is terminated by deprotonation of the carbocation or by capture by a water molecule and the terpene hydrocarbon or alcohol is released. Some terpene synthases produce a single product, but most of them produce multiple products. These enzymes are responsible for the extremely large number of terpene skeletons. Finally, in the last stage of terpenoid biosynthesis, the terpene molecules may undergo several steps of secondary enzymatic transformations such as hydroxylations, isomerisations, oxido-reductions or acylations, leading to the tens of thousand of different terpene molecules.

This invention relates to the isolation of nucleic acids encoding for sesquiterpene synthases. The sesquiterpene synthases convert farnesyl pyrophosphate to the different sesquiterpene skeletons. Over 300 sesquiterpene hydrocarbons and 3000 sesquiterpenoids have been identified (Joulain, D., and König, W. A. The Atlas of Spectral Data of Sesquiterpene Hydrocarbons, EB Verlag, Hamburg, 1998; Connolly, J. D., Hill R. A. Dictionary of Terpenoids, Vol 1, Chapman and Hall (publisher), 1991), and many new structures are identified each year. There is virtually an infinity of sesquiterpene synthases present in the plant kingdom, all using the same substrate but having different product profiles.

Several sesquiterpene synthase encoding cDNA or genes have been cloned and characterized from different plant sources, e.g., 5-epi-aristolochene synthases form *Nicotiana tabacum* (Facchini, P. J. and Chappell, J. (1992) Proc. Natl. Acad. Sci. U.S.A. 89, 11088-11092.) and from *Capsicum annum* (Back, K., et al. (1998) Plant Cell Physiol. 39 (9), 899-904), a vetispiradiene synthase from *Hyoscyamus muticus* (Back, K. and Chappell, J. (1995) J. Biol. Chem. 270 (13), 7375-7381), a (E)-β-farnesene synthases from *Mentha piperita* and *Citrus junos* (Crock, J., et al. (1997) Proc. Natl. Acad. Sci. U.S.A. 94 (24), 12833-12838; Maruyama et al (2001) Biol. Pharm. Bull. 24(10), 1171-1175), a δ-selinene synthase and a γ-humulene synthase from *Abies grandis* (Steele, C. L., et al. (1998) J. Biol. Chem. 273 (4), 2078-

2089), δ-cadinene synthases from *Gossypium arboreum* (Chen, X. Y., et al. (1995) Arch. Biochem. Biophys. 324 (2), 255-266; Chen, X. Y., et al. (1996) J. Nat Prod. 59, 944-951.), a E-α-bisabolene synthase from *Abies grandis* (Bohlmann, J., et al. (1998) Proc. Natl. Acad. Sci. U.S.A. 95 (12), 6756-6761.), a germacrene C synthase from *Lycopersicon esculentum* (Colby, S. M., et al. (1998) Proc. Natl. Acad. Sci. U.S.A. 95 (5), 2216-2221.), an epi-cedrol synthase and an amorpha-4,11-diene synthase from *Artemisia annua* (Mercke, P., et al. (1999) Arch. Biochem. Biophys. 369 (2), 213-222; Mercke, P., et al. (2000) Arch. Biochem. Biophys. 381 (2), 173-180.), a germacrene D synthase from *Lycopersicon esculentum* (van der Hoeven, R. S., Monforte, A. J., Breeden D., Tanksley, S. D., and Steffens J. C. (2000) The Plan cell 12, 2283-2294) and germacrene A synthases from *Lactuca sativa*, from *Cichorium intybus* and from *Solidago canadensis* (Bennett, M. H., et al. (2002) Phytochem. 60, 255-261; Bouwmeester, H. J., et al. (2002) Plant Physiol. 129 (1), 134-144; Prosser I, et al. (2002) Phytochem. 60, 691-702).

One embodiment of the present invention relates to the isolation from patchouli plants of nucleic acid encoding for sesquiterpenes synthases. Patchouli oil is an important perfumery raw material obtained by steam distillation of the leaves from the plant *Pogostemon cablin* (patchouli), a Lamiaceae growing in tropical regions. The oil, which has a long-lasting pleasant odor with woody, earth and camphoraceous notes, is largely used in perfumery. In patchouli plants the biosynthesis and storage of the oil is associated with anatomically specialized structures: glandular structures found on the leaf surface and internal structures found all over the plant. The biosynthesis of the oil occurs in the early stage of the leaf development (Henderson, W., Hart, J. W., How, P, and Judge J. (1969) Phytochem. 9, 1219-1228). The oil is rich in sesquiterpenes. The sesquiterpene patchoulol (FIG. 1) is the major constituent (5 to 40%) and contributes considerably to the typical note.

The Biosynthesis of patchoulol in Patchouli (*Pogostemon cablin*) leaves has been studied and elucidated. Croteau and co-worker studied the mechanism of biosynthesis of patchoulol using patchouli leaf extracts and achieved the purification and characterization of the patchoulol synthase (Croteau et al (1987) Arch. Biochem. Biophys. 256(1), 56-68; Munck and Croteau (1990) Arch. Biochem. Biophys. 282(1), 55-64). A single sesquiterpene synthase is responsible for the biosynthesis of patchoulol from farnesyl pyrophosphate. The patchoulol synthase from patchouli is a multiple product enzyme synthesizing patchoulol as a main product and several secondary products including α-bulnesene, α-guaiene, α-patchoulene, β-patchoulene (FIG. 1) (Croteau et al (1987) Arch. Biochem. Biophys. 256(1), 56-68; Munck and Croteau (1990) Arch. Biochem. Biophys. 282(1), 55-64). The chemical synthesis of patchoulol and structurally related compounds involves a large number of steps and so far, there is no commercially interesting chemical process. Therefore, a biochemical route for the production of patchoulol would be of great interest. The engineering of a biochemical route for the production of Patchoulol requires the isolation of the genes encoding for patchoulol synthase.

One embodiment of the present invention provides nucleic acids isolated from patchouli leaves and encoding for sesquiterpene synthases. Another embodiment of the invention relates to the transformation of bacteria with the isolated nucleic acids of the invention, including the production of the resultant recombinant sesquiterpene synthases. For example, one embodiment of the invention relates to the use of a recombinant sesquiterpene synthase to produce a mixture of sesquiterpenes, with patchoulol being the major product. Other embodiments of the invention relate to the use of another recombinant sesquiterpene synthases to produce γ-curcumene as major product, and other recombinant sesquiterpene synthases to produce germacrane-type sesquiterpenes (FIG. 1). A further embodiment of the invention relates to the use of sesquiterpene synthases in vivo to produce at least one terpenoid, for example patchoulol.

SUMMARY OF THE INVENTION

In one embodiment, the invention relates to isolated nucleic acids that encode sesquiterpene synthases. As used herein, a sesquiterpene synthase may also be referred to by at least one compound produced by the enzyme upon contact with an acyclic pyrophosphate terpene precursor such as farnesyl-pyrophosphate. In one embodiment, it is the major product produced. For example, a sesquiterpene synthase capable of producing patchoulol as one of its products, for example, the major product, may be referred to as a patchoulol synthase. Using this convention, examples of nucleic acids of the invention include cDNAs encoding γ-curcumene synthase (PatTpsA) (SEQ ID NO:1); (−)-germacrene D synthase (PatTpsBF2) (SEQ ID NO:2); (+)-germacrene A synthase (PatTpsCF2) (SEQ ID NO:3); another (−)-germacrene D synthase (PatTpsB15) (SEQ ID NO:4); and a patchoulol synthase (PatTps177) (SEQ ID NO:5).

In one embodiment, the present invention provides an isolated nucleic acid encoding a patchoulol synthase.

In another embodiment, an isolated nucleic acid encoding a γ-curcumene synthase is provided.

In one embodiment, the invention provides an isolated nucleic acid selected from: (a) a nucleic acid comprising the nucleotide sequence substantially as set out in SEQ ID NO:1, SEQ ID NO:2, SEQ ID NO:3, SEQ ID NO:4, or SEQ ID NO:5; (b) a nucleic acid encoding the polypeptide substantially set out in SEQ ID NO:6, SEQ ID NO:7, SEQ ID NO:8, SEQ ID NO:9, or SEQ ID NO:10; and (c) a nucleic acid that hybridizes to the nucleic acid of (a) or (b) under low stringency conditions, wherein the polypetide encoded by said nucleic acid has sesquiterpene synthase activity. In one embodiment, the defined conditions are moderate stringency conditions and in a further embodiment the defined conditions are high stringency conditions. Other embodiments include: a polypeptide encoded by a nucleic acid of the invention, or obtained from the method for preparing a nucleic acid encoding an improved sesquiterpene synthase; a host cell comprising a nucleic acid of the invention; a non-human organism modified to harbor a nucleic acid of the invention; and methods of producing a polypeptide comprising culturing host cells of the invention.

In an embodiment, the invention provides an isolated patchoulol synthase. In another embodiment, the present invention provides an isolated γ-curcumene synthase.

In a further embodiment, the invention provides a vector comprising at least one nucleic acid according to the invention.

In yet another embodiment, the present invention provides a method for preparing a nucleic acid encoding an improved sesquiterpene synthase.

Other embodiments include, methods of making a recombinant host cell comprising introducing a vector of the invention into a host cell.

In one embodiment, the invention provides a method of making at least one sesquiterpene synthase comprising culturing a host modified to contain at least one nucleic acid sequence under conditions conducive to the production of said at least one sesquiterpene synthase wherein said at least one nucleic acid is the nucleic acid according to the invention.

In another embodiment the invention provides a method of making at least one terpenoid comprising A) contacting at least one acyclic pyrophosphate terpene precursor with at least one polypeptide encoded by a nucleic acid according to the invention, and B) optionally, isolating at least one terpenoid produced in A). In one embodiment, the method is performed in vivo. For example, at least one synthase is produced in vivo in, for example, a microrganism or a plant comprising at least one acyclic pyrophosphate terpene precursor. Preferably, the at least one terpenoid is chosen from sesquiterpenes. Preferably, the at least one acyclic pyrophosphate terpene precursor is farnesyl-pyrophosphate. The sesquiterpenes produced by the methods of the invention include, but are not limited to, patchoulol, γ-curcumene and other germacrane-type sesquiterpenes (FIG. 1). In an embodiment, the at least one terpenoid is a sesquiterpene chosen from γ-curcumene and/or patchoulol.

It is to be understood that both the foregoing general description and the following detailed description are exemplary and explanatory only and are not restrictive of the invention as claimed. Reference will now be made in detail to exemplary embodiments of the present invention.

BRIEF DESCRIPTION OF THE FIGURES

FIG. 3: Alignment of the amino acid sequences deduced from the 3'RACE products (SEQ ID NOS 31-33, respectively in order of appearance). White letters on black background and black letters on gray background represent respectively identical and similar residues in two out of the three sequences.

FIG. 4: Alignment of the amino acid sequences deduced from the 5'RACE products (SEQ ID NOS 34-36, respectively in order of appearance). White letters on black background and black letters on gray background represent respectively identical and similar residues in two out of the three sequences.

FIG. 5: Alignment of the amino acid sequences deduced from the cDNAs isolated in this work (SEQ ID NOS: 6-10 and 12, respectively in order of appearance). White letters on black background and black letters on gray background represent respectively identical and similar residues in four out of the six sequences.

FIG. 7: Coupled gas chromatographic-mass spectrophotometric (GC-MS) analysis of sesquiterpenes produced by PatTpsA (SEQ ID NO:6). A. Total ion chromatogram. The peak of farnesol (retention time 16.15) is due to hydrolysis of FPP by the *E. coli* alkaline phosphatase present in the crude protein extract. All peaks except peak 1 are contaminants from the incubation medium or from the solvent use for the extraction. B. Mass spectrum and calculated retention index for peak 1.

FIG. 8: Coupled gas chromatographic-mass spectrophotometric (GC-MS) analysis of sesquiterpenes produced by Pat-TpsBF2 (SEQ ID NO:7). A. Total ion chromatogram. The peak of farnesol (retention time 16.16) is due to hydrolysis of FPP by the *E. coli* alkaline phosphatase present in the crude protein extract. All peaks except peak 1 are contaminant from the incubation medium or from the solvent use for the extraction. B. Mass spectrum and calculated retention index for peak 1.

FIG. 13: DNA (SEQ ID NO:1) and aminoacid (SEQ ID NO:6) sequences of PatTpsA, a γ-curcumene synthase.

FIG. 14: DNA (SEQ ID NO:2) and aminoacid (SEQ ID NO:7) sequences of PatTpsBF2, a (−)-germacrene D synthase.

FIG. 15: DNA (SEQ ID NO:3) and aminoacid (SEQ ID NO:8) sequences of PatTpsCF2, a (+)-germacrene A synthase.

FIG. 16: DNA (SEQ ID NO:4) and aminoacid (SEQ ID NO:9) sequences of PatTpsB15, another (−)-germacrene D synthase.

FIG. 17: DNA (SEQ ID NO:5) and aminoacid (SEQ ID NO:10) sequences of PatTps177, a patchoulol synthase.

FIG. 18: Partial DNA (SEQ ID NO:11) and aminoacid (SEQ ID NO:12) sequences of PatTpsC16, a sesquiterpene synthase.

Figure 1:
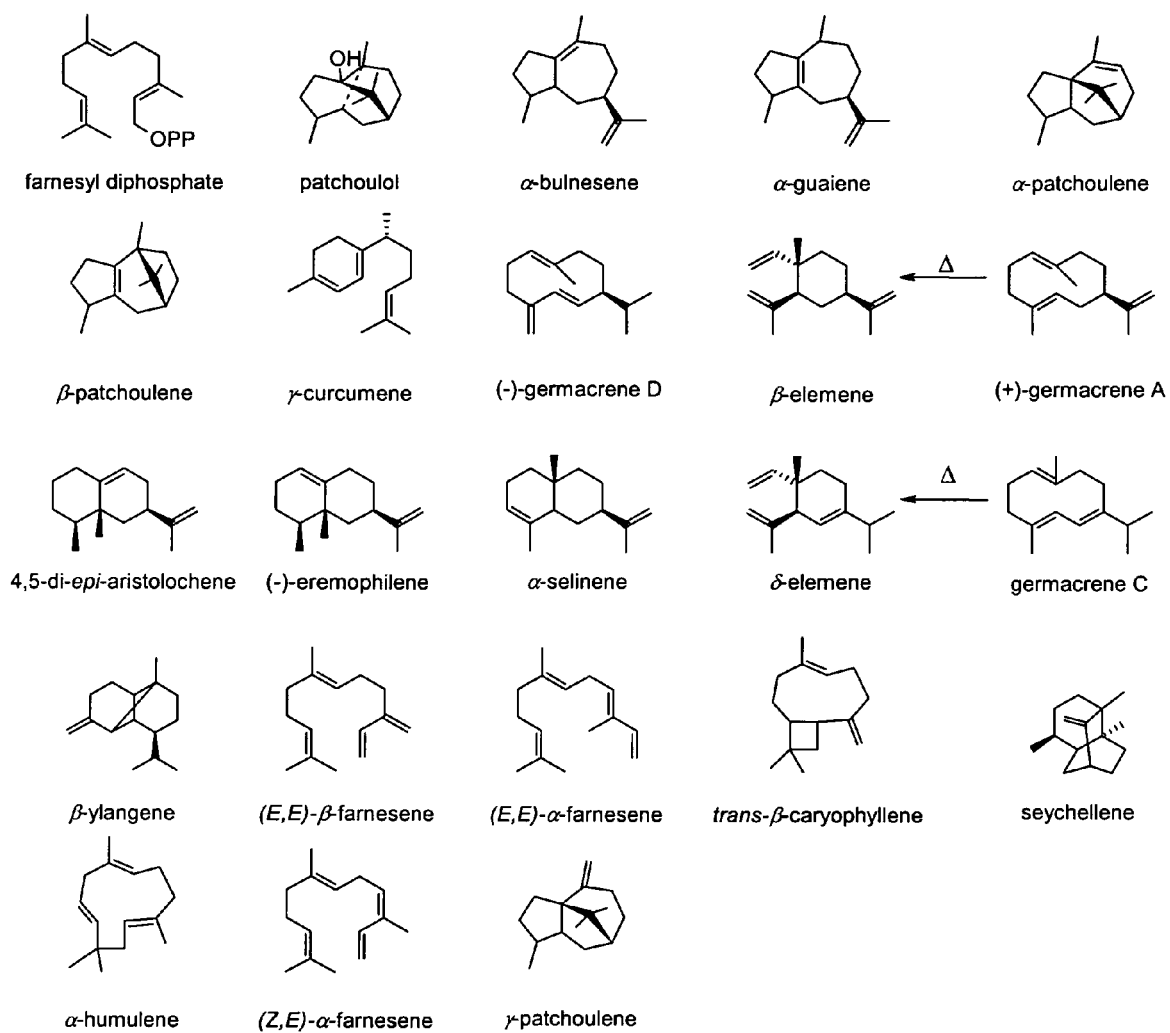
FIG. 1: Structure of sesquiterpene molecules cited in the text.

ABBREVIATIONS USED bp base pair.
DNA deoxyribonucleic acid.
cDNA complementary DNA.

DTT dithiothreitol.
EDTA ethylenediaminotetraacetic acid.
FPP Farnesyl-pyrophosphate.
IPP isopentenyl pyrophosphate
IPTG isopropyl-D-thiogalacto-pyranoside.
PCR polymerase chain reaction.
RT-PCR reverse transcription—polymerase chain reaction.
3'-/5'-RACE 3' and 5' rapid amplification of cDNA ends.
RNA ribonucleic acid.
mRNA messenger ribonucleic acid.
SDS-PAGE SDS-polyacrylamide gel electrophoresis.

DETAILED DESCRIPTION OF THE PREFERRED EMBODIMENTS

A terpene is an unsaturated hydrocarbon based on an isoprene unit ($C_5H_8$) which may be acyclic or cyclic. Terpene derivatives, include but are not limited to camphor, menthol, terpineol, borneol, geraniol, nootkatone, cedrol, and patchoulol. Terpenes or Terpenoids, as used herein includes terpenes and terpene derivatives, including compounds that have undergone one or more steps of functionalization such as hydroxylations, isomerizations, oxido-reductions or acylations. As used herein, a sesquiterpene is a terpene based on a $C_{15}$ structure and includes sesquiterpenes and sesquiterpene derivatives, including compounds that have undergone one or more steps of functionalization such as hydroxylations, isomerizations, oxido-reductions or acylations.

As used herein, a derivative is any compound obtained from a known or hypothetical compound and containing essential elements of the parent substance.

As used herein, sesquiterpene synthase is any enzyme that catalyzes the synthesis of a sesquiterpene.

The phrase "identical," "substantially identical." or "substantially as set out," means that a relevant sequence is at least 70%, 75%, 80%, 85%, 90%, 92%, 95%, 96%, 97%, 98%, or 99% identical to a given sequence. By way of example, such sequences may be allelic variants, sequences derived from various species, or they may be derived from the given sequence by truncation, deletion, amino acid substitution or addition. For polypeptides, the length of comparison sequences will generally be at least 20, 30, 50, 100 or more amino acids. For nucleic acids, the length of comparison sequences will generally be at least 50, 100, 150, 300, or more nucleotides. Percent identity between two sequences is determined by standard alignment algorithms such as, for example, Basic Local Alignment Tool (BLAST) described in Altschul et al. (1990) J. Mol. Biol., 215:403-410, the algorithm of Needleman et al. (1970) J. Mol. Biol., 48:444-453, or the algorithm of Meyers et al. (1988) Comput. Appl. Biosci., 4:11-17.

The invention thus provides, in one embodiment, an isolated nucleic acid selected from: (a) a nucleic acid comprising the nucleotide sequence substantially as set out in SEQ ID NO:1, SEQ ID NO:2, SEQ ID NO:3, SEQ ID NO:4, or SEQ ID NO:5; (b) a nucleic acid encoding the polypeptide substantially set out in SEQ ID NO:6, SEQ ID NO:7, SEQ ID NO:8, SEQ ID NO:9, or SEQ ID NO:10; and (c) a nucleic acid that hybridizes to the nucleic acid of (a) or (b) under low stringency conditions, wherein the polypetide encoded by said nucleic acid has sesquiterpene synthase activity. In one embodiment, the defined conditions are moderate stringency conditions and in a further embodiment the defined conditions are high stringency conditions.

As used herein, one determines whether a polypeptide encoded by a nucleic acid of the invention has sesquiterpene synthase activity by the enzyme characterization assay described in the examples herein.

As used herein, the term hybridization or hybridizes under certain conditions is intended to describe conditions for hybridization and washes under which nucleotide sequences that are significantly identical or homologous to each other remain bound to each other. The conditions may be such that sequences, which are at least about 70%, such as at least about 80%, and such as at least about 85-90% identical, remain bound to each other. Definitions of low stringency, moderate, and high stringency hybridization conditions are provided herein.

Appropriate hybridization conditions can be selected by those skilled in the art with minimal experimentation as exemplified in Ausubel et al. (1995), Current Protocols in Molecular Biology, John Wiley & Sons, sections 2, 4, and 6. Additionally, stringency conditions are described in Sambrook et al. (1989) Molecular Cloning: A Laboratory Manual, 2nd ed., Cold Spring Harbor Press, chapters 7, 9, and 11. As used herein, defined conditions of low stringency are as follows. Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×106 32P-labeled probe is used. Filters are incubated in hybridization mixture for 18-20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography.

As used herein, defined conditions of moderate stringency are as follows. Filters containing DNA are pretreated for 7 h at 50° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×106 32P-labeled probe is used. Filters are incubated in hybridization mixture for 30 h at 50° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography.

As used herein, defined conditions of high stringency are as follows. Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in the prehybridization mixture containing 100 µg/ml denatured salmon sperm DNA and 5-20×10$^6$ cpm of 32P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 minutes. Other conditions of low, moderate, and high stringency well known in the art (e.g., as employed for cross-species hybridizations) may be used if the above conditions are inappropriate.

In an embodiment of the nucleic acid of the invention, the nucleic acid is chosen from (a) a nucleic acid comprising the nucleotide sequence substantially as set out in SEQ ID NO:5;

(b) a nucleic acid encoding the polypeptide substantially set out in SEQ ID NO:10; and (c) a nucleic acid that hybridizes to the nucleic acid of (a) or (b) under low stringency conditions, wherein the polypeptide encoded by said nucleic acid has sesquiterpene synthase activity.

In another embodiment of the nucleic acid of the invention, the nucleic acid is chosen from (a) a nucleic acid comprising the nucleotide sequence substantially as set out in SEQ ID NO:1; (b) a nucleic acid encoding the polypeptide substantially set out in SEQ ID NO:6; and (c) a nucleic acid that hybridizes to the nucleic acid of (a) or (b) under low stringency conditions, wherein the polypeptide encoded by said nucleic acid has sesquiterpene synthase activity.

In an embodiment, the nucleic acids are at least 70%, at least 85%, at least 90% or at least 95% indentical to nucleotides SEQ ID NO: 5 and/or 1. Preferbaly, the nucleic acid of step (c) hybridizes under moderate, more preferably under high stringency conditions to the nucleic acids of (a) or (b) above.

Preferably, a nucleic acid and/or polypeptide of the invention is isolated from Patchouli (*Pogostemon cablin*). In an embodiment, the nucleic acid is isolated from patchouli leaves.

Preferably, the nucleic acid according to the invention comprises SEQ ID NO:5. Preferably, the nucleic acid comprises SEQ ID NO:10.

In a particular embodiment, the invention relates to certain isolated nucleotide sequences including those that are substantially free from contaminating endogenous material. The terms "nucleic acid" or "nucleic acid molecule" refer to a deoxyribonucleotide or ribonucleotide polymer in either single-or double-stranded form, and unless otherwise limited, would encompass known analogs of natural nucleotides that can function in a similar manner as naturally occurring nucleotides. A "nucleotide sequence" also refers to a polynucleotide molecule or oligonucleotide molecule in the form of a separate fragment or as a component of a larger nucleic acid. The nucleotide sequence or molecule may also be referred to as a "nucleotide probe." Some of the nucleic acid molecules of the invention are derived from DNA or RNA isolated at least once in substantially pure form and in a quantity or concentration enabling identification, manipulation, and recovery of its component nucleotide sequence by standard biochemical methods. Examples of such methods, including methods for PCR protocols that may be used herein, are disclosed in Sambrook et al., Molecular Cloning: A Laboratory Manual, 2nd ed., Cold Spring Harbor Laboratory, Cold Spring Harbor, N.Y. (1989), Current Protocols in Molecular Biology edited by F. A. Ausubel et al., John Wiley and Sons, Inc. (1987), and Innis, M. et al., eds., PCR Protocols: A Guide to Methods and Applications, Academic Press (1990).

As described herein, the nucleic acid molecules of the invention include DNA in both single-stranded and double-stranded form, as well as the RNA complement thereof. DNA includes, for example, cDNA, genomic DNA, chemically synthesized DNA, DNA amplified by PCR, and combinations thereof. Genomic DNA, including translated, non-translated and control regions, may be isolated by conventional techniques, e.g., using any one of the cDNAs of the invention, or suitable fragments thereof, as a probe, to identify a piece of genomic DNA which can then be cloned using methods commonly known in the art. In general, nucleic acid molecules within the scope of the invention include sequences that hybridize to sequences of the invention under hybridization and wash conditions described above and of 5°, 10°, 15°, 20°, 25°, or 30° below the melting temperature of the DNA duplex of sequences of the invention, including any range of conditions subsumed within these ranges.

In another embodiment, the nucleic acids of the invention comprises a sequence substantially as set out in SEQ ID NO:1, SEQ ID NO:2, SEQ ID NO:3, SEQ ID NO:4, or SEQ ID NO:5. In one embodiment, the nucleic acids are at least 70%, at least, 85%, at least 90%, or at least 95% identical to nucleotides SEQ ID NO:1, SEQ ID NO:2, SEQ ID NO:3, SEQ ID NO:4, or SEQ ID NO:5. In one embodiment, the nucleic acid comprises the nucleotide sequence SEQ ID NO:1, SEQ ID NO:2, SEQ ID NO:3, SEQ ID NO:4, or SEQ ID NO:5. In a further embodiment, the nucleic acid encodes a protein that has sesquiterpene synthase activity, as demonstrated, for example, in the enzyme assay described in the examples. Nucleic acids comprising regions conserved among different species, are also provided.

In yet another embodiment, the nucleic acid comprises a contiguous stretch of at least 50, 100, 250, 500, or 750 contiguous nucleotides of SEQ ID NO:1, SEQ ID NO:2, SEQ ID NO:3, SEQ ID NO:4, or SEQ ID NO:5. Such contiguous fragments of these nucleotides may also contain at least one mutation so long as the mutant sequence retains the functionality of the original sequence and the capacity to hybridize to these nucleotides under low or high stringency conditions, such as for example, moderate or high stringency conditions. Such a fragment can be derived, for example, from nucleotide (nt) 200 to nt 1600, from nt 800 to nt 1600, from nt 1000 to nt 1600, from nt 200 to nt 1000, from nt 200 to nt 800, from nt 400 to nt 1600, or from nt 400 to nt 1000 of SEQ ID NO:1, SEQ ID NO:2, SEQ ID NO:3, SEQ ID NO:4, or SEQ ID NO:5.

As described above, polypeptides encoded by the nucleic acids of the invention are encompassed by the invention. The isolated nucleic acids of the invention may be selected from a nucleic acid encoding the polypeptide substantially set out in SEQ ID NO:6, SEQ ID NO:7, SEQ ID NO:8, SEQ ID NO:9, or SEQ ID NO:10. In one embodiment, the polypeptides are at least 70%, at least 85%, at least 90%, or at least 95% identical to SEQ ID NO:6, SEQ ID NO:7, SEQ ID NO:8, SEQ ID NO:9, or SEQ ID NO:10.

In one embodiment, a polypeptide of the invention comprises an amino acid sequence as set out in SEQ ID NO:6, SEQ ID NO:7, SEQ ID NO:8, SEQ ID NO:9, or SEQ ID NO:10. In another embodiment, the polypeptide comprises an amino acid sequence substantially as set out in SEQ ID NO:6, SEQ ID NO:7, SEQ ID NO:8, SEQ ID NO:9, or SEQ ID NO:10. In yet another embodiment, the polypeptide comprises an amino acid sequence that is at least 80%, at least 85% identical, at least 90% or at least 95% identical to of SEQ ID NO:6, SEQ ID NO:7, SEQ ID NO:8, SEQ ID NO:9, or SEQ ID NO:10. In one embodiment, the polypeptide has sesquiterpene synthase activity, as demonstrated, for example, in the enzyme assay described below.

Preferably, the polypeptide is the polypeptide as substantially set out in SEQ ID NO: 6 and/or 10. More preferably, the polypeptide comprises an amino acid sequence that is at least 75%, at least 80%, at least 85%, at least 90%, at least 95%, at least 97%, or which corresponds totally to the amino acid sequence of SEQ ID NO: 6 and/or 10.

Due to the degeneracy of the genetic code wherein more than one codon can encode the same amino acid, multiple DNA sequences can code for the same polypeptide. Such variant DNA sequences can result from genetic drift or artificial manipulation (e.g., occurring during PCR amplification or as the product of deliberate mutagenesis of a native sequence). The present invention thus encompasses any nucleic acid capable of encoding a protein derived from the SEQ ID NO:1, SEQ ID NO:2, SEQ ID NO:3, SEQ ID NO:4, or SEQ ID NO:5 or variants thereof.

Deliberate mutagenesis of a native sequence can be carried out using numerous techniques well known in the art. For example, oligonucleotide-directed site-specific mutagenesis procedures can be employed, particularly where it is desired to mutate a gene such that predetermined restriction nucleotides or codons are altered by substitution, deletion or insertion. Exemplary methods of making such alterations are disclosed by Walder et al. (Gene 42:133, 1986); Bauer et al. (Gene 37:73, 1985); Craik (BioTechniques, Jan. 12-19, 1985); Smith et al. (Genetic Engineering: Principles and Methods, Plenum Press, 1981); Kunkel (Proc. Natl. Acad. Sci. USA 82:488, 1985); Kunkel et al. (Methods in Enzymol. 154:367, 1987); and U.S. Pat. Nos. 4,518,584 and 4,737,462.

In one embodiment, the invention provides for isolated polypeptides. As used herein, the term "Polypeptides" refers to a genus of polypeptide or peptide fragments that encompass the amino acid sequences identified herein, as well as smaller fragments. Alternatively, a polypeptide may be defined in terms of its antigenic relatedness to any peptide encoded by the nucleic acid sequences of the invention. Thus, in one embodiment, a polypeptide within the scope of the invention is defined as an amino acid sequence comprising a linear or 3-dimensional epitope shared with any peptide encoded by the nucleic acid sequences of the invention. Alternatively, a polypeptide within the scope of the invention is recognized by an antibody that specifically recognizes any peptide encoded by the nucleic acid sequences of the invention. Antibodies are defined to be specifically binding if they bind polypeptides of the invention with a $K_a$ of greater than or equal to about $10^7$ $M^{-1}$, such as greater than or equal to $10^8$ $M^{-1}$.

A Polypeptide "variant" as referred to herein means a polypeptide substantially homologous to a native polypeptide, but which has an amino acid sequence different from that encoded by any of the nucleic acid sequences of the invention because of one or more deletions, insertions or substitutions.

Variants can comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. See Zubay, Biochemistry, Addison-Wesley Pub. Co., (1983). The effects of such substitutions can be calculated using substitution score matrices such a PAM-120, PAM-200, and PAM-250 as discussed in Altschul, (J. Mol. Biol. 219:555-65, 1991). Other such conservative substitutions, for example, substitutions of entire regions having similar hydrophobicity characteristics, are well known.

Naturally-occurring peptide variants are also encompassed by the invention. Examples of such variants are proteins that result from alternate mRNA splicing events or from proteolytic cleavage of the polypeptides described herein. Variations attributable to proteolysis include, for example, differences in the N- or C-termini upon expression in different types of host cells, due to proteolytic removal of one or more terminal amino acids from the polypeptides encoded by the sequences of the invention.

Variants of the sesquiterpenes synthases of the invention may be used to attain desired enhanced or reduced enzymatic activity, modified regiochemistry or stereochemistry, or altered substrate utilization or product distribution. Furthermore, variants may be prepared to have at least one modified property, for example an increased affinity for the substrate, an improved specificity for the production of one or more desired compounds, a different product distribution, a different enzymatic activity, an increase of the velocity of the enzyme reaction, a higher activity or stability in a specific environment (pH, temperature, solvent, etc), or an improved expression level in a desired expression system. A variant or site direct mutant may be made by any method known in the art. As stated above, the invention provides recombinant and non-recombinant, isolated and purified polypeptides, such as from patchouli plants. Variants and derivatives of native polypeptides can be obtained by isolating naturally-occurring variants, or the nucleotide sequence of variants, of other or same plant lines or species, or by artificially programming mutations of nucleotide sequences coding for native patchouli polypeptides. Alterations of the native amino acid sequence can be accomplished by any of a number of conventional methods.

Accordingly, the present invention provides a method for preparing a variant functional sesquiterpene synthase, the method comprising the steps of (a) selecting any of nucleic acids from the group consisting of SEQ ID NO: , 2, 3, 4 or 5, (b) altering the nucleic acid sequence to obtain a polulation of mutant nucleic acids, and, (c) transforming host cells with the mutant nucleic acid to express polypeptides, and, (d) screening the polypeptides for a functional polypeptide having at least one modified property. The modified property may be any desired property, for example the properties mentioned above. The alteration of the selected nucleic acid may be performed by random mutagenesis, site-specific mutagenesis or DNA shuffling, for example. The alteration may be at least one point mutation, deletion or insertion. For example, polypeptides having an amino acid sequence encoded by a nucleic acid obtained from shuffling techniques, involving at least any of SEQ ID NO 1-5, are also encompassed by the present invention. The steps of the method according to this embodiment of the invention, such as screening the polypeptides for a functional polypeptide, are known to the skilled person who will routinely adapt known protocols to the specific modified property that is desired.

For example mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered gene wherein predetermined codons can be altered by substitution, deletion or insertion. The present invention also encompasses nucleic acids obtained from altering a nucleic acid of the present invention, for example in order to obtain a variant polypeptide.

In one embodiment, the invention contemplates: vectors comprising the nucleic acids of the invention. For example, a vector comprising at least one nucleic acid chosen from (a) a nucleic acid comprising the nucleotide sequence substantially as set out in SEQ ID NO:1, SEQ ID NO:2, SEQ ID NO:3, SEQ ID NO:4, or SEQ ID NO:5; (b) a nucleic acid encoding the polypeptide substantially set out in SEQ ID NO:6, SEQ ID NO:7, SEQ ID NO:8, SEQ ID NO:9, or SEQ ID NO:10; and (c) a nucleic acid that hybridizes to the nucleic acid of (a) or (b) under low stringency conditions, wherein the polypetide encoded by said nucleic acid has sesquiterpene synthase activity.

A vector as used herein includes any recombinant vector including but not limited to viral vectors, bacteriophages and plasmids.

Recombinant expression vectors containing a nucleic acid sequence of the invention can be prepared using well known methods. In one embodiment, the expression vectors include a cDNA sequence encoding the polypeptide operably linked to suitable transcriptional or translational regulatory nucleotide sequences, such as those derived from a mammalian, microbial, viral, plant, or insect gene. Examples of regulatory sequences include transcriptional promoters, operators, or enhancers, mRNA ribosomal binding sites, and appropriate sequences which control transcription and translation initiation and termination. Nucleotide sequences are "operably linked" when the regulatory sequence functionally relates to the cDNA sequence of the invention. Thus, a promoter nucleotide sequence is operably linked to a cDNA sequence if the promoter nucleotide sequence controls the transcription of the cDNA sequence. The ability to replicate in the desired host cells, usually conferred by an origin of replication, and a selection gene by which transformants are identified can additionally be incorporated into the expression vector.

In addition, sequences encoding appropriate signal peptides that are not naturally associated with the polypeptides of the invention can be incorporated into expression vectors. For example, a DNA sequence for a signal peptide (secretory leader) can be fused in-frame to a nucleotide sequence of the invention so that the polypeptides of the invention is initially translated as a fusion protein comprising the signal peptide. A signal peptide that is functional in the intended host cells enhances extracellular secretion of the expressed polypeptide. The signal peptide can be cleaved from the polypeptide upon secretion from the cell. Alternatively, the signal peptide may be suitable to direct the polypeptide to an intracellular location, for example into specific a cell compartment or organell.

Fusions of additional peptide sequences at the amino and carboxyl terminal ends of the polypeptides of the invention can be used to enhance expression of the polypeptides, aid in the purification of the protein or improve the enzymatic activity of the polypeptide in a desired environment or expression system, for example.

In one embodiment, the invention includes a host cell comprising a nucleic acid of the invention. Another embodiment of the invention is a method of making a recombinant host cell comprising introducing the vectors of the invention, into a host cell. In a further embodiment, a method of producing a polypeptide comprising culturing the host cells of the invention under conditions to produce the polypeptide is contemplated. In one embodiment the polypeptide is recovered. The methods of invention include methods of making at least one sesquiterpene synthase of the invention comprising culturing a host cell comprising a nucleic acid of the invention, and recovering the sesquiterpene synthase accumulated.

Suitable host cells for expression of polypeptides of the invention include prokaryotes, yeast or higher eukaryotic cells. For example, the suitable host cell is a plant cell. Appropriate cloning and expression vectors for use with bacterial, fungal, yeast, and mammalian cellular hosts are described, for example, in Pouwels et al., Cloning Vectors: A Laboratory Manual, Elsevier, N.Y., (1985). Cell-free translation systems could also be employed to produce the disclosed polypeptides using RNAs derived from DNA constructs disclosed herein.

Prokaryotes include gram negative or gram positive organisms, for example, *E. coli* or *Bacilli*. Suitable prokaryotic host cells for transformation include, for example, *E. coli, Bacillus subtilis, Salmonella typhimurium*, and various other species within the genera *Pseudomonas, Streptomyces*, and *Staphylococcus*. In a prokaryotic host cell, such as *E. coli*, the polypeptides can include a N-terminal methionine residue to facilitate expression of the recombinant polypeptide in the prokaryotic host cell. The N-terminal methionine can be cleaved from the expressed recombinant polypeptide.

Examples of useful expression vectors for prokaryotic host cells include those derived from commercially available plasmids such as the cloning vector pET plasmids (Novagen, Madison, Wis., USA) or yet pBR322 (ATCC 37017). pBR322 contains genes for ampicillin and tetracycline resistance and thus provides simple means for identifying transformed cells. To construct an expression vector using pBR322, an appropriate promoter and a DNA sequence encoding one or more of the polypeptides of the invention are inserted into the pBR322 vector. Other commercially available vectors include, for example, pKK223-3 (Pharmacia Fine Chemicals, Uppsala, Sweden) and pGEM-1 (Promega Biotec, Madison, Wis., USA). Other commercially available vectors include those that are specifically designed for the expression of proteins; these would include pMAL-p2 and pMAL-c2 vectors that are used for the expression of proteins fused to maltose binding protein (New England Biolabs, Beverly, Mass., USA).

Promoter sequences commonly used for recombinant prokaryotic host cell expression vectors include bacteriophage T7 promoter (Studier F. W. and Moffatt B. A., J. Mol. Biol. 189:113, 1986), β-lactamase (penicillinase), lactose promoter system (Chang et al., Nature 275:615, 1978; and Goeddel et al., Nature 281:544, 1979), tryptophan (trp) promoter system (Goeddel et al., Nucl. Acids Res. 8:4057, 1980; and EP-A-36776), and tac promoter (Maniatis, Molecular Cloning: A Laboratory Manual, Cold Spring Harbor Laboratory, p. 412, 1982). A particularly useful prokaryotic host cell expression system employs a phage λ PL promoter and a cI857ts thermolabile repressor sequence. Plasmid vectors available from the American Type Culture Collection ("ATCC"), which incorporate derivatives of the PL promoter, include plasmid pHUB2 (resident in *E. coli* strain JMB9 (ATCC 37092)) and pPLc28 (resident in *E. coli* RR1 (ATCC 53082)).

Polypeptides of the invention can also be expressed in yeast host cells, preferably from the *Saccharomyces* genus (e.g., *S. cerevisiae*). Other genera of yeast, such as *Pichia* or *Kluyveromyces* (e.g. *K. lactis*), can also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionine, 3-phosphoglycerate kinase (Hitzeman et al., J. Biol. Chem. 255:2073, 1980), or other glycolytic enzymes (Hess et al., J. Adv. Enzyme Reg. 7:149, 1968; and Holland et al., Biochem. 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Hitzeman, EPA-73, 657 or in Fleer et. al., Gene, 107:285-195 (1991); and van den Berg et. al., Biotechnology, 8:135-139 (1990). Another alternative is the glucose-repressible ADH2 promoter described by Russell et al. (J. Biol. Chem. 258:2674, 1982) and Beier et al. (Nature 300:724, 1982). Shuttle vectors replicable in both yeast and *E. coli* can be constructed by inserting DNA sequences from pBR322 for selection and replication in *E. coli* (Ampr gene and origin of replication) into the above-described yeast vectors.

One embodiment of the invention is a non-human organism modified to harbor a nucleic acid of the invention. The non-human organism and/or host cell may be modified by any methods known in the art for gene transfer including, for example, the use of deliver devices such as lipids and viral vectors, naked DNA, electroporation, chemical methods and particle-mediated gene transfer. In one embodiment, the non-human organism is a plant, insect or microorganism.

For example, in one embodiment the invention provides a method of making at least one sesquiterpene synthase comprising culturing a host modified to contain at least one nucleic acid under conditions conducive to the production of said at least one sesquiterpene synthase wherein said at least one nucleic acid is chosen from (a) a nucleic acid comprising the nucleotide sequence substantially as set out in SEQ ID NO:1, SEQ ID NO:2, SEQ ID NO:3, SEQ ID NO:4, or SEQ ID NO:5; (b) a nucleic acid encoding the polypeptide substantially set out in SEQ ID NO:1, SEQ ID NO:2, SEQ ID NO:3, SEQ ID NO:4, or SEQ ID NO:5; and (c) a nucleic acid that hybridizes to the nucleic acid of (a) or (b) under low stringency conditions, wherein the polypetide encoded by said nucleic acid has sesquiterpene synthase activity.

In a further embodiment, the host is a plant such as tobacco or patchouli, animal or microorganism also including but not limited to bacterial cells, yeast cells, plant cells, and animal cells. As used herein, plant cells and animals cells include the use of plants and animals as a host. For example, in some embodiments of the invention, expression is in a genetically modified non-human organism.

For example, mammalian or insect host cell culture systems are employed to express recombinant polypeptides of the invention. Such host cell culture systems, as well as methods for introducing DNA into mammalian or incesct cells are known to the skilled person.

Similarly, transcriptional and translational control sequences for mammalian host cell expression vectors have been reported extensively. They can be excised from viral genomes, for example.

There are several methods known in the art for the creation of transgenic plants. These include, but are not limited to: electroporation of plant protoplasts, liposome-mediated transformation, *agrobacterium*-mediated transformation, polyethylene-glycol-mediated transformation, microinjection of plant cells, and transformation using viruses. In one embodiment, direct gene transfer by particle bombardment is utilized. In another embodiment, *agrobacterium*-mediated transformation is utilized.

Direct gene transfer by particle bombardment provides an example for transforming plant tissue. In this technique a particle, or microprojectile, coated with DNA is shot through the physical barriers of the cell. Particle bombardment can be used to introduce DNA into any target tissue that is penetrable by DNA coated particles, but for stable transformation, it is imperative that regenerable cells be used. Typically, the particles are made of gold or tungsten. The particles are coated with DNA using either CaCl2 or ethanol precipitation methods which are commonly known in the art.

DNA coated particles are shot out of a particle gun. A suitable particle gun can be purchased from Bio-Rad Laboratories (Hercules, Calif.). Particle penetration is controlled by varying parameters such as the intensity of the explosive burst, the size of the particles, or the distance particles must travel to reach the target tissue.

The DNA used for coating the particles may comprise an expression cassette suitable for driving the expression of the gene of interest that will comprise a promoter operably linked to the gene of interest.

Methods for performing direct gene transfer by particle bombardment are disclosed in U.S. Pat. No. 5,990,387 to Tomes et al. In one embodiment, the cDNAs of the invention may be expressed in such a way as to produce either sense or antisense RNA. Antisense RNA is RNA that has a sequence which is the reverse complement of the mRNA (sense RNA) encoded by a gene. A vector that will drive the expression of antisense RNA is one in which the cDNA is placed in "reverse orientation" with respect to the promoter such that the non-coding strand (rather than the coding strand) is transcribed. The expression of antisense RNA can be used to down-modulate the expression of the protein encoded by the mRNA to which the antisense RNA is complementary. Vectors producing antisense RNA's could be used to make transgenic plants, as described above.

In one embodiment, transfected DNA is integrated into a chromosome of a non-human organism such that a stable recombinant systems results. Any chromosomal integration method known in the art may be used in the practice of the invention, including but not limited to, recombinase-mediated cassette exchange (RMCE), viral site specific chromosomal insertion, adenovirus, and pronuclear injection.

A further embodiment of the invention includes methods of making terpenoids and sesquiterpene compounds using the nucleotides and polypeptides of the invention. Examples include methods of making at least one terpenoid comprising contacting at least one acyclic pyrophosphate terpene precursor with at least one polypeptide encoded by the nucleic acid according to the invention. Preferably, the nucleic acid is chosen from (a) a nucleic acid comprising the nucleotide sequence substantially as set out in SEQ ID NO:1, SEQ ID NO:2, SEQ ID NO:3, SEQ ID NO:4, or SEQ ID NO:5; (b) a nucleic acid encoding the polypeptide substantially set out in SEQ ID NO:6, SEQ ID NO:7, SEQ ID NO:8, SEQ ID NO:9, or SEQ ID NO:10; and (c) a nucleic acid that hybridizes to the nucleic acid of (a) or (b) under low stringency conditions, wherein the polypetide encoded by said nucleic acid has sesquiterpene synthase activity, and isolating at least one terpenoid produced. Another example is a method of making at least one terpenoid comprising contacting at least one acyclic pyrophosphate terpene precursor with at least one polypeptide substantially set out in SEQ ID NO:6, SEQ ID NO:7, SEQ ID NO:8, SEQ ID NO:9, or SEQ ID NO:10 and isolating at least one terpenoid produced.

As used herein an acyclic pyrophosphate terpene precursor is any acyclic pryrophosphate compound that is a precursor to the production of at least one terpene including but not limited to geranyl-pyrophosphate (GPP), farnesyl-pyrophosphate (FPP) and geranylgeranyl-pyrophosphate (GGPP).

In one embodiment, the at least one terpenoid is chosen from sesquiterpenes. In one embodiment, the at least one acyclic pyrophosphate terpene precursor is farnesyl-pyrophosphate. In a further embodiment, the at least one sesquiterpenes is chosen from patchoulol, γ-curcumene and other germacrane-type sesquiterpenes shown in instant FIGS. 1-12. The terpenoids of the invention may be isolated by any method used in the art including but not limited to chromatography, extraction and distillation.

In one embodiment, the distribution of products or the actual products formed may be altered by varying the pH at which the synthase contacts the acyclic pyrophosphate terpene precursor, such as, for example, farnesyl-pyrophosphate. In one embodiment, the pH is 7. In a further embodiment the pH is less than 7, such as, for example, 6, 5, 4, and 3.

Also within the practice of the invention is an organism (e.g., micro-organism or plant) that is used to construct a platform for high level production of a substrate of sesquiterpene synthases (e.g., FPP) and the introduction of a nucleic acid of the invention into the organism. For example, at least one nucleic acid of the invention that encodes a sesquiterpene synthase is incorporated into a non-human organism that produces FPP thereby effecting conversion of FPP to a sesquiterpene, and the subsequent metabolic production of the sesquiterpene. In one embodiment, this results in a platform for the high level production of sesquiterpenes.

In one embodiment, the nucleic acids of the invention are used to create other nucleic acids coding for sesquiterpene synthases. For example, the invention provides for a method of identifying a sesquiterpene synthases comprising constructing a DNA library using the nucleic acids of the invention, screening the library for nucleic acids which encode for at least one sesquiterpene synthase. The DNA library using the nucleic acids of the invention may be constructed by any process known in the art where DNA sequences are created using the nucleic acids of the invention as a starting point, including but not limited to DNA suffling. In such a method, the library may be screened for sesquiterpene synthases using a functional assay to find a target nucleic acid that encodes a sesquiterpene synthase. The activity of a sesquiterpene synthase may be analyzed using, for example, the methods described herein. In one embodiment, high through put screening is utilized to analyze the activity of the encoded polypeptides.

As used herein a "nucleotide probe" is defined as an oligonucleotide or polynucleotide capable of binding to a target nucleic acid of complementary sequence through one or more types of chemical bonds, through complementary base pairing, or through hydrogen bond formation. As described above, the oligonucleotide probe may include natural (ie. A, G, C, or T) or modified bases (7-deazaguanosine, inosine, etc.). In addition, bases in a nucleotide probe may be joined by a linkage other than a phosphodiester bond, so long as it does not prevent hybridization. Thus, oligonucleotide probes may have constituent bases joined by peptide bonds rather than phosphodiester linkages.

A "target nucleic acid" herein refers to a nucleic acid to which the nucleotide probe or molecule can specifically hybridize. The probe is designed to determine the presence or absence of the target nucleic acid, and the amount of target nucleic acid. The target nucleic acid has a sequence that is complementary to the nucleic acid sequence of the corresponding probe directed to the target. As recognized by one of skill in the art, the probe may also contain additional nucleic acids or other moieties, such as labels, which may not specifically hybridize to the target. The term target nucleic acid may refer to the specific nucleotide sequence of a larger nucleic acid to which the probe is directed or to the overall sequence (e.g., gene or mRNA). One skilled in the art will recognize the full utility under various conditions.

Other than in the operating example, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. The following examples are intended to illustrate the invention without limiting the scope as a result. The percentages are given on a weight basis.

Unless defined otherwise, all technical and scientific terms used herein have the same meaning as commonly understood by one of ordinary skill in the art to which this invention belongs. Although any methods and materials similar or equivalent to those described herein can also be used in the practice of the present invention, exemplary methods and materials are described for illustrative purposes. All publications mentioned in this application are incorporated by reference to disclose and describe the methods and/or materials in connection with which the publications are cited.

Additionally, the publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

It must be noted that as used herein and in the appended claims, the singular forms "a", "and", and "the" include plural referents unless the context clearly dictates otherwise. Thus, for example, reference to "a terpene" includes a plurality of such terpenes and reference to "a vector" includes reference to one or more vectors and equivalents thereof known to those skilled in the art.

Methods, techniques, and/or protocols (collectively "methods") that can be used in the practice of the invention are not limited to the particular examples of these procedures cited throughout the specification but embrace any procedure known in the art for the same purpose. For example, with respect to methods for the expression of DNA sequences in host cells, the present invention is not limited to the protocols cited herein, but includes any method available in the art to the skilled artisan to express DNA sequences in host cells.

EXAMPLES

The following examples are intended to illustrate the invention without limiting the scope as a result.

Material

*Pogostemon Cablin* (patchouli) plants used in the present examples were obtained from a local producer, Le Jardin des Senteurs (Neuchâtel, Switzerland), and were grown and propagated by cuttings in a green house in the Centre d'Horticulture de Lullier (Jussy, Switzerland). Other available sources of patchouli plants can be used in the following examples. GC-MS analysis of leaves from the plants showed a high patchoulol content in all size leaves. Total RNA and mRNA were extracted from a blend of different size leaves freshly collected from the patchouli plants.

Example 1

Isolation of Total RNA and mRNA

Leaves were collected from the patchouli plants, immediately frozen in liquid nitrogen and grounded using a mortar and pestle. Total RNA was extracted using the Concert™ Plant RNA Reagent from Invitrogen following the manufacturer's instructions. Typically, an average of 200 µg total RNA was obtained from 1 g of grounded tissue. The concentration of RNA was estimated from the OD at 260 nm. The integrity of the RNA was evaluated on an agarose gel by verifying the integrity of the ribosomic RNA bands. The mRNA was purified from the total RNA by oligodT-cellulose affinity chromatography using the FastTrack® 2.0 mRNA isolation Kit (Invitrogen) following the manufacturer's instructions.

Example 2

Reverse Transcription (RT)-PCR

RT-PCR was performed using the Qiagen OneStep RT-PCR Kit and an Eppendorf Mastercycler Gradient thermal cycler. Typical reaction mixtures contain 10 µl 5× Qiagen OneStep RT-PCR buffer, 400 µM each dNTP, 400 nM each primer, 2 µl Qiagen OneStep RT-PCR Enzyme Mix, 1 µl RNasin® Ribonuclease Inhibitor (Promega Co.) and 1 µg total RNA in a final volume of 50 µl. The thermal cycler conditions were: 30 min at 50° C. (reverse transcription); 15 min at 95° C. (DNA polymerase activation); 40 cycles of 45 sec at 94° C., 10 sec at 42° C. and 45 sec at 72° C.; and finally 10 min at 72° C.

The sizes of the PCR products were evaluated on a 1% agarose gel. The bands corresponding to the expected size were excised from the gel, purified using the QIAquick® Gel Extraction Kit (Qiagen) and cloned in the pCR®2.1-TOPO vector using the TOPO TA cloning Kit (Invitrogen). Inserted DNA fragments were then subject to DNA sequencing and the sequence compared against the GenBank non-redundant protein database (NCBI) using the BLASTX algorithm (Altschul, S. F., Gish, W., Miller, W., Myers, E. W., and Lipman, D. J. (1990) Basic local alignment search tool. *J. Mol. Biol.* 215, 403-410).

Example 3

3'- and 5'-RACE

For 3' and 5' Rapid Amplification of cDNA Ends (RACE), adaptor ligated double stranded cDNA was prepared from the patchouli leaf mRNA using the Marathon™ cDNA Amplification Kit (Clontech) following the manufacturer's protocol. The 3'- or 5'-ends of the specific cDNAs were amplified with Advantage® 2 Polymerase Mix using a combination of gene- and adaptor-specific oligonucleotides. Typical RACE reaction mixtures contain, in a final volume of 50 µl, 5 µL 10×PCR Reaction Buffer (Clontech), 200 nM each dNTP, 1 µl Advantage® 2 Polymerase Mix, 200 µM adaptor-specific primer (Clontech), 200 µM gene-specific primer and 5 µl of 50 to 250 fold diluted cDNA. Amplification was performed on an Eppendorf Mastercycler Gradient thermal cycler. The thermal Cycling conditions were as follows: 1 min at 94° C., 5 cycles of 30 sec at 94° C. and 2 to 4 min at 72° C., 5 cycles of 30 sec at 94° C. and 2 to 4 min at 70° C., 20 cycles of 20 sec at 94° C. and 2 to 4 min at 68° C. A second round of amplification using a nested adaptor-specific primer (Clontench) and a nested gene-specific primer was routinely performed. The amplification products were evaluated, sub-cloned, and the sequence analyzed as described above.

The sizes of the PCR products were evaluated on a 1% agarose gel. The bands corresponding to the expected size were excised from the gel, purified using the QIAquick® Gel Extraction Kit (Qiagen) and cloned in the pCR®2.1-TOPO vector using the TOPO TA cloning Kit (Invitrogen). Inserted DNA fragments were then subject to DNA sequencing. The sequence were first compared against the GenBank non-redundant protein database (NCBI) using the BLASTX algorithm (Altschul, S. F., Gish, W., Miller, W., Myers, E. W., and Lipman, D. J. (1990) Basic local alignment search tool. *J. Mol. Biol.* 215, 403-410) and then compared against the initial DNA sequence to ensure that significant DNA sequence overlap was obtained.

Example 4

Construction of Expression Plasmids

For functional expression of the sesquiterpene synthases, the cDNA were sub-cloned in the pET11a (Novagen), the pET101 (Invitrogen) or the pET102 (Invitrogen) expression plasmids. In these plasmids the cDNA is placed downstream of the T7 promoter controlling the expression of the recombinant protein in *E. coli* cells. After transformation of *E coli* cells, the expression of the protein may be induced by isopropyl-beta-D-thiogalactopyranoside (IPTG).

The ligations of inserts in pET11a required the use of the NdeI and BamHI restriction endonucleases. Inserts were amplified by PCR using as primers oligonucleotides designed to introduce the appropriate restriction enzyme recognition sites (NdeI and BamHI) immediately before the start codon and after the stop codon. The amplified cDNAs were purified, digested with the appropriate restriction enzymes and ligated into pET11a plasmid digested with the same enzymes. Constructs were verified by digestion and DNA sequencing.

For the ligation of PatTpsA into pET 11a, the cDNA was amplified by PCR using the primers PatTpsA Nde and PatTpsA Bam (Table 1) to introduce an NdeI restriction site immediately before the start codon and a BamHI restriction site immediately after the stop codon.

The pET101 and pET102 plasmids used with the pET Directional TOPO® Expression Kit (Invitrogen) allow the directional cloning of PCR products without need of introducing restriction sites (useful when the cDNA contains, in the coding region, the restriction sites required for the sub-cloning). For the ligation of cDNAs in these two plasmids, inserts were amplified by PCR using as primers, oligonucleotides designed to amplify the cDNAs including the start and stop codons. Ligations were performed according to the manufacturer protocol. Constructs were verified by DNA sequencing.

For ligation of PatTpsA in pET102, the cDNA was amplified using the primers PatTpsA topo and PatTpsA Stop (Table 1). For the ligation of PatTpsBF2 into pET101 and pET102, the cDNA was amplified by PCR using the primers PatTpsBF2.1 topo and PatTpsBF2.1 stop (Table 1). For amplification of PatTpsCF2 for ligation in pET101, the primers PatTpsCF2 topo and PatTpsCF2 stop were used (Table 1). For amplification of PaTpsB15 and PatTps177 for ligation in pET101, the primer pairs PatTpsB15 topo-PatTpsB15 stop and PatTps177 topo-PatTps177 stop were respectively used.

All amplifications of cDNA for expression were performed using the Pfu DNA polymerase (Promega), in a final volume of 50 µl containing 5 µl of Pfu DNA polymerase 10× buffer, 200 µM each dNTP, 0.4 µM each forward and reverse primer, 2.9 units Pfu DNA polymerase and 5 µl of 100-fold diluted cDNA (prepared as described herein using the Marathon™ cDNA Amplification Kit (Clontech)). The thermal cycling conditions were as follows: 2 min at 95° C.; 25 cycles of 30 sec at 95° C., 30 sec at 52° C. and 4 min at 72° C.; and 10 min at 72° C. The PCR products were purified on an agarose gel and eluted using the QIAquick® Gel Extraction Kit (Qiagen).

Example 5

Sesquiterpene Synthases Expression

In a standard protein expression experiment, the expression plasmids containing the sesquiterpene synthase cDNAs as well as the empty plasmid (for negative control) were transformed into the BL21 (DE3) or the BL21 Star™ (DE3) *E. coli* cells (Novagen). Single colonies of transformed *E. coli* were used to inoculate 5 ml LB medium. After 5 to 6 hours of incubation at 37° C., the cultures were transferred to a 20° C. incubator and left 1 hour for equilibration. Expression of the protein was then induced by addition of 0.5 mM IPTG and the culture incubated over-night at 20° C. The next day, the cells were collected by centrifugation, resuspended in 0.5 ml Extraction Buffer (50 mM MOPSO pH 7, 5 mM DTT, 10% glycerol) and sonicated 3 times 30 s. The cell debris were sedimented by centrifugation 30 min at 18,000 g and the supernatant containing the soluble proteins was recovered. The expression of the sesquiterpene synthases was evaluated by separation of the protein extract on a SDS-PAGE, staining with coomassie blue and comparison to protein extract obtained from cells transformed with the empty plasmid.

Example 6

Enzyme Assay

The enzymatic assays were performed in Teflon sealed glass tubes using 50 to 100 μl of protein extract in a final volume of 1 mL Extraction Buffer supplemented with 15 mM $MgCl_2$ and 100 to 250 μM FPP (Sigma). The medium was overlaid with 1 ml pentane and the tubes incubated over-night at 30° C. The pentane phase, containing the sesquiterpenes, was recovered and the medium extract with a second volume of pentane. The combined pentane fractions were concentrated under nitrogen and analyzed by Gas Chromatography on a on a Hewlett-Packard 6890 Series GC system using a 0.25 mm inner diameter by 30 m SPB-1 (Supelco) capillary column. The carrier gas was He at constant flow of 1.6 ml/min. Injection was done in splitless mode with the injector set at 200° C. and the oven programmed from 100° C. (0 min hold) at 7.5° C./min to 200° C. (0 min hold) followed by 20° C./min to 280° C. (2 min hold). Detection was made with a flame ionization detector. Compound identification was based on retention time identity with authentic standards when available. For confirmation of the products identities, samples were analyzed by combined capillary GC-MS using a Hewlett-Packard 6890 GC-quadrupole mass selective detector system, equipped with a 0.25 mm inner diameter by 30 m SPB-1 (Supelco) capillary column. The oven was programmed from 80° C. (0 min hold) to 280° C. at 7° C. at a constant flow of 1.5 ml/min He. The spectra were recorded at 70 eV with an electron multiplier voltage of 2200V. Retention time of the enzyme products were compared to the retention time of authentic standard, or the Kovats retention index was calculated and compared to published data (Joulain, D., and König, W. A. The Atlas of Spectral Data of Sesquiterpene Hydrocarbons, EB Verlag, Hamburg, 1998).

Example 7

Isolating Sesquiterpene Synthase cDNA using RT-PCR

Figure 2:
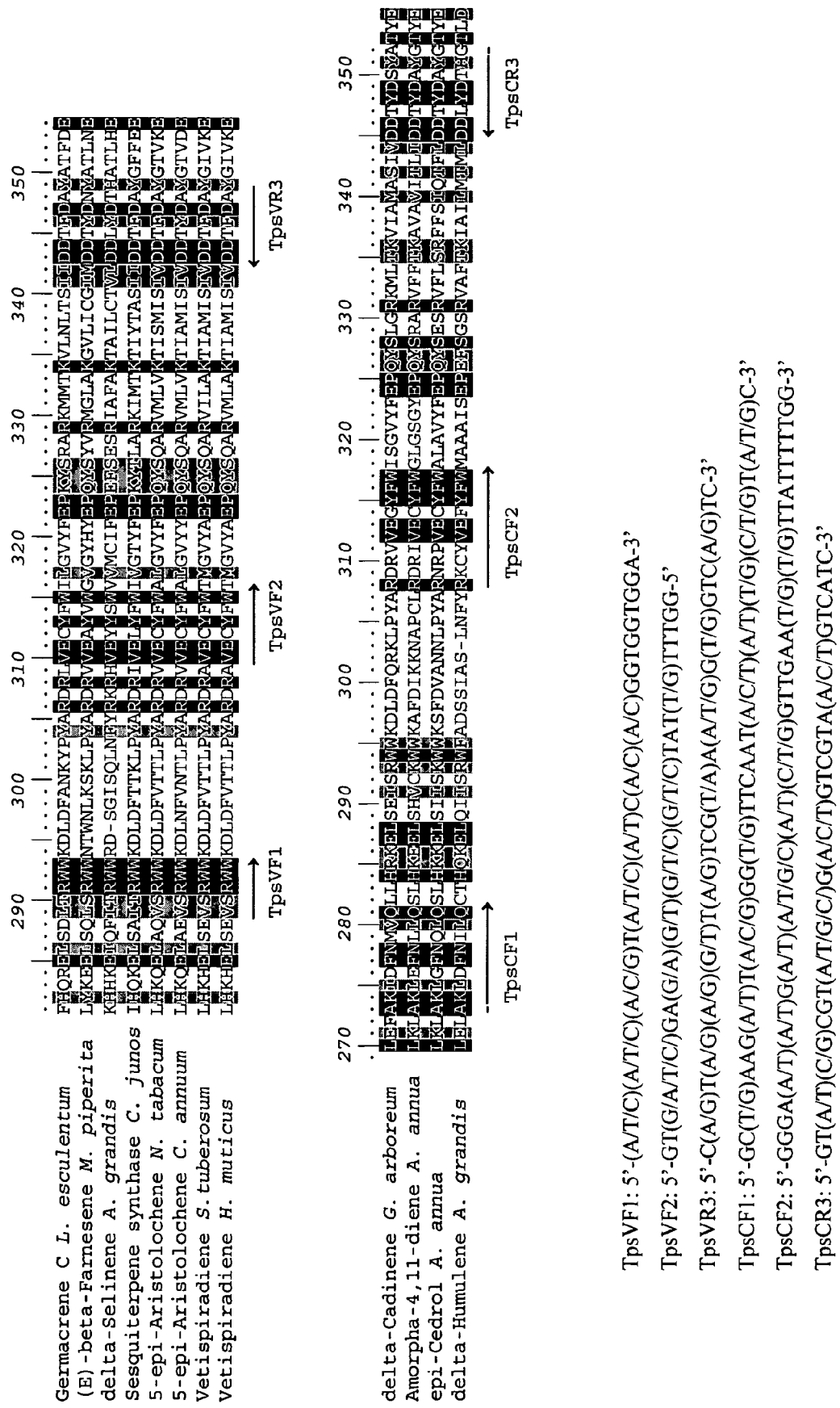
FIG. 2: Central part of the alignments of the amino acid sequences of two groups of sesquitepene synthases (SEQ ID NOS 13-24, respectively in order of appearance) used to design the sesquiterpene synthase-specific degenerated primers (SEQ ID NOS 25-30, respectively in order of appearance). The arrows below each alignment show the regions of the alignment used to design each primer and their orientation.

The deduced amino-acid sequences of plant sesquiterpene synthases were aligned to identify conserved regions and design plant sesquiterpene synthase-specific oligonucleotides. In order to obtain better sequence homology, the sequences were separated into two groups (FIG. 2). The first group contained the sequences of the Germacrene C synthase from *Lycopersicon esculentum* cv. VFNT cherry (Colby, S. M., et al. (1998) Proc. Natl. Acad. Sci. U.S.A. 95 (5), 2216-2221.), the (E)-β-farnesene synthase from *Mentha x piperita* (Crock, J., et al. (1997) Proc. Natl. Acad. Sci. U.S.A. 94 (24), 12833-12838), the δ-selinene synthase from *Abies grandis* (Steele, C. L., et al. (1998) J. Biol. Chem. 273 (4), 2078-2089), a sesquiterpene synthase from Citrus junos (GenBank accession no. AF288465) the 5-epi-aristolochene synthases from *Nicotiana tabacum* (Facchini, P. J. and Chappell, J. (1992) Proc. Natl. Acad. Sci. U.S.A. 89, 11088-11092) and from *Capsicum annuum* (Back, K., et al. (1998) Plant Cell Physiol. 39 (9), 899-904), the vetispiradiene synthases from *Solanum tuberosum* and from *Hyoscyamus muticus* (Back, K. and Chappell, J. (1995) J. Biol. Chem. 270 (13), 7375-7381). The second group contained sequences of the (+)-δ-cadinene synthases from *Gossypium arboreum* (Chen, X. Y., et al. (1995) Arch. Biochem. Biophys. 324 (2), 255-266), the amorpha-4,11-diene synthase (Mercke, P., et al. (2000) Arch. Biochem. Biophys. 381 (2), 173-180) and the epi-cedrol synthase (Mercke, P., et al. (1999) Arch. Biochem. Biophys. 369 (2), 213-222) from *Artemisia* annua and the γ-humulene synthase from *Abies grandis* (Steele, C. L., et al. (1998) J. Biol. Chem. 273 (4), 2078-2089). The highest sequence homology was found in the central part of the sequences. Three regions containing sufficiently conserved amino-acids were selected and degenerated oligonucleotides specific for these regions were designed (i.e. four forward (TpsVF1, TpsVF2, TpsCF1, TpCF2) and two reverse primers (TpsVR3, TpsCR3) were deduced) (FIG. 2).

The total RNA from patchouli leaves was used to perform RT-PCR (reverse transcription-polymerase chain reaction) using several combinations of these oligonucleotides. Amplification using the primer combination TpsCF1 and TpsCR3 gave an amplicon (named Pat5) with the expected size (180 bp). This fragment was purified and reamplified with the same primers. The 180 bp amplicon (Pat5-10) was purified, sub-cloned in the pCR®2.1-TOPO plasmid (Invitrogen), and five clones were sequenced. Among them, one clone, Pat5-104, had sesquiterpene synthases sequence similarities and was named PatTpsA.

In a similar way, the Pat5 fragment was reamplified with the primers TpsCF2 and TpsCR3. This provided three clones (120 bp insert), Pat8-1-1, Pat8-1-6 and Pat8-1-7 having sequence similarities with sesquiterpene synthases. Pat8-1-6 and Pat8-1-7 had the same DNA sequenced as the previously obtained clone Pat5-10-4 (PatTpsA). Pat8-1-1 had a different DNA sequence and was named PatTpsC.

In an other experiment, using the primers TpsVF2 and TpsCR3, a DNA fragment of 120 bp (Pat8-10-2) was obtained, which showed sequence similarities with sesquiterpene synthases and significant differences with the two previously obtained clones. This clone was named PatTpsB.

Example 8

Isolating Sesquiterpene Synthases cDNA using 5'/3'-RACE

To isolate the full-length sequences of the sesquiterpene synthases, a 5'/3'-RACE (Rapid Amplification of cDNA Ends) approach was first used. Forward primer specific for the three identified sesquiterpene synthases sequences were designed (Table 1) and 3'RACE was performed. Fragments with the expected size were obtained for all three clones. Sequence analysis identified the 3' half cDNA from three different clones that were named PatA-14, PatB-15 and PatC-16 (FIG. 3).

In order to obtain the other half (5' end) of this clones, reverse primers were designed based on these three sequences (two primers for each clone; Table 1). 5'RACE was performed and the 5'end half-length of three different sesquiterpene synthases were obtained: PatAF2, PatBF2 and PatCF2 (FIG. 4). Sequence comparison of the 3'RACE products and the 5'RACE products, showed that there was a sequence overlap (54 bp) with 100% identity between PatA-14 and PatAF2, thus confirming that the full-length sequence of PatTpsA had been obtained (FIG. 5). However, for the four other RACE products there was no overlap, meaning that the two 3'RACE products and the two 5'RACE products were from different clones.

At this stage, we had one full-length cDNA (PatTpsA), two 3'end half cDNAs and two 5'end half cDNA. In order to obtain the full-length cDNA of these last clones we designed specific primers. First, forward primers specific for PatBF2 and PatCF2 were designed (Table 1) and 3'RACE was performed. The sequences of the 3'RACE products obtained were analyzed and showed sesquiterpene synthase similarities. Comparison with PatBF2 and PatCF2 revealed sufficient sequence overlap to conclude that the full-length sequence of the cDNA for the two sesquiterpene synthases named PatTpsBF2 and PatTpsCF2 had been obtained (FIG. 5). In the same way, new reverse primers specific for PatB-15 and PatC-16 were designed (Table 1). The regions in the sequences with the most differences with the previously obtained clones were chosen in order to favor the amplification of PatB-15 and PatC-16 cDNAs. The 5'RACE worked for PatB-15 and thus the full-length cDNA sequence of PatTpsB-15 was obtained (FIG. 5). For PatC-16, the 5'RACE did not produce the expected DNA fragment and this clone remains uncompleted.

In order to isolate new cDNAs encoding for sesquiterpene synthases, oligonucleotides were designed based on the DNA sequence of the four sesquiterpene synthase encoding cDNAs already isolated from patchouli leaves. The DNA sequence from PatTpsA, PatTpsBF2, PatTpsCF2 and PatTpsB15 were aligned and conserved regions were searched. Four regions were selected (FIG. 6) and two forward and two reverse degenerated oligonucleotide were designed (Table 1). This four "patchouli sesquiterpene synthases-specific" primers were used in PCR using as template cDNA prepared from patchouli leaf mRNA (Marathon Kit, Clontech). Analysis of the DNA sequence from different clones obtained by this approach showed that, as could be expected, most of them were fragments of the cDNA already isolated. But two clones, FID177 and FID178 (which were identical), were from a new sesquiterpene synthase. 3'RACE using the specific primers Pat177-5R1 and Pat177-5R2 (Table 1) and 5'RACE using the specific primers Pat177-3R1 and Pat177-3R2 (Table 1) gave the full-length sequence of this cDNA, which was named PatTps177.

Figure 6:
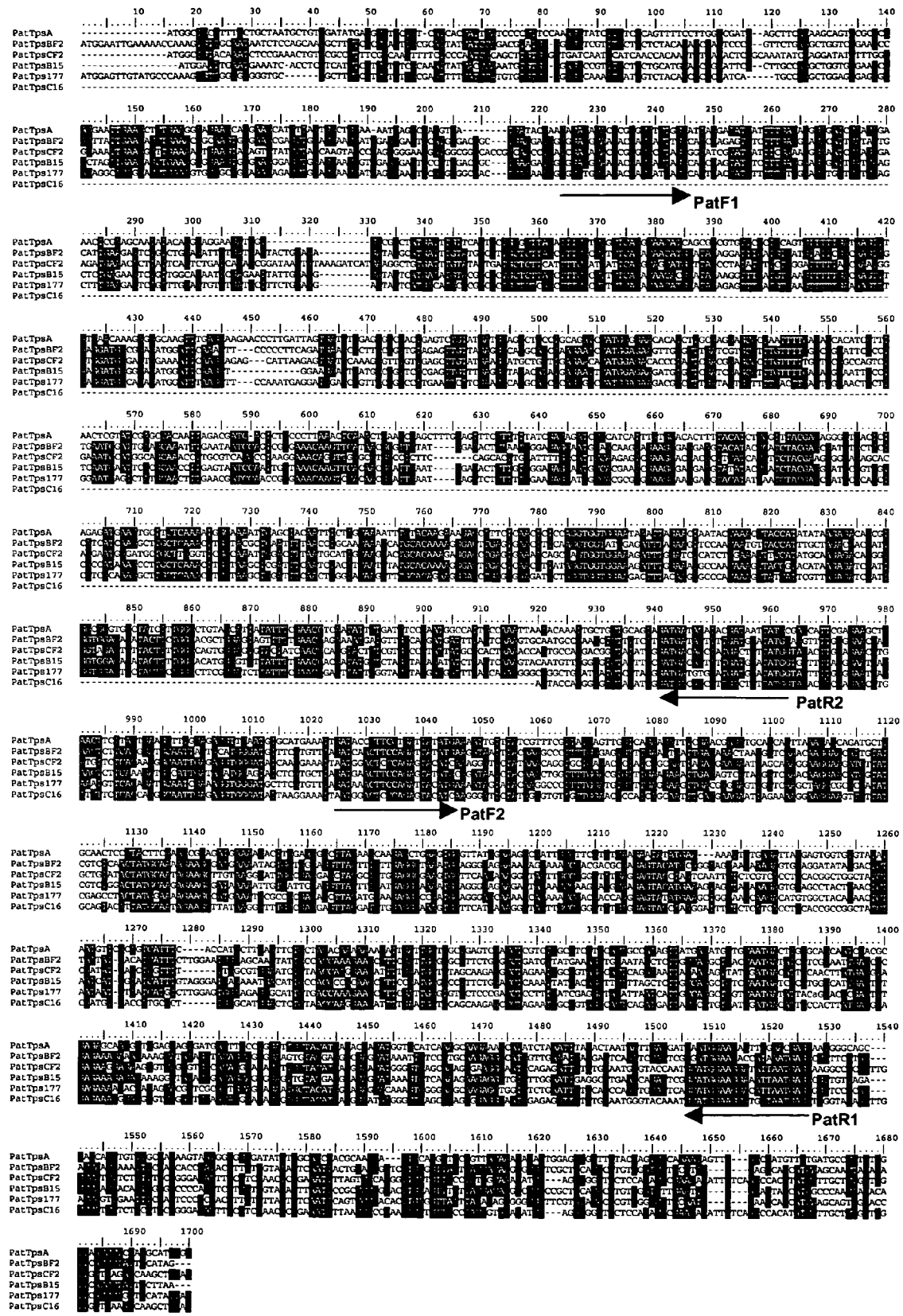
FIG. 6: Alignment of the nucleotide sequences of open reading frames of the cDNAs isolated in this work (SEQ ID NOS: 1-5 and 11, respectively in order of appearance). White letters on black background represent conserved nucleotides in four out of the six sequences. The regions used to design the degenerated primers are marked with arrows bellow the alignment and the names of the primers are indicated.

An alignment of the amino acid sequence deduced from the five full-length and the one partial sesquiterpene synthase cDNA is shown in FIG. 5. The alignment of the nucleotidic sequences of these cDNAs is shown in FIG. 6, and the DNA and aminoacid sequences from the sesquiterpene synthases obtained in these experiments in shown in FIGS. 13 to 18.

Table 1: Name, sequence and description of oligonucleotides used in this work. SEQ ID NOS 37-76 are shown respectively in order of appearance in Table 1. (V=A+C+G, D=A+T+G, B=T+C+G, H=A+T+C, W=A+T, S=C+G, K=T+G, M=A+C, Y=C+T, R=A+G).

TABLE 1

| Name | Sequence (5' to 3') | Description |
| --- | --- | --- |
| PatTpsAF1 | CCTACCATATATAAGAGACAGCGTGGCGG (SEQ ID NO:37) | forward primer specific for PatTpsA |
| PatTpsAF2 | TGCCTATCTTTGGGCTGTAGCATTATATTTCG (SEQ ID NO:38) | nested forward primer specific for PatTpsA |
| PatTpsBF1 | CATGGGGTTTTATTTTGAACCACAATATGC (SEQ ID NO:39) | forward primer specific for PatTpsB |
| PatTpsBF2 | GAAATATCTTAGTCAAAGTACAATGTTTGGTGTC (SEQ ID NO:40) | nested forward primer specific for PatTpsB |
| PatTpsCF1 | GAGTGTTCCATGAACCCAAGTACTCTCG (SEQ ID NO:41) | forward primer specific for PatTpsC |
| PatTpsCF2 | CTCGTGCCCGTATTATGTTTACTAAAACC (SEQ ID NO:42) | nested forward primer specific for PatTpsC |
| PatTpsAR1 | GTAAGAAGTTGAGCTTCTCGAATGGTCGC (SEQ ID NO:43) | reverse primer specific for PatTpsA-14 |
| PatTpsAR2 | GGTCGCATAATTATCGTATGTATCATCTACTCGAG (SEQ ID NO:44) | nested reverse primer specific for PatTpsA-14 |
| PatTpsBR1 | TCTAAGCATGAGATACTCCATCTATCAATGGC (SEQ ID NO:45) | reverse primer specific for PatTpsB-15 |
| PatTpsBR2 | CCTTAAAGCACCATATGCATCAAAAGTGTCATC (SEQ ID NO:46) | nested reverse primer specific for PatTpsB-15 |
| PatTpsCR1 | CTGGGAGTCCATTAATTTCCTTAATATCCCACC (SEQ ID NO:47) | reverse primer specific for PatTpsC-16 |

TABLE 1-continued

| Name | Sequence (5' to 3') | Description |
| --- | --- | --- |
| PatTpsCR2 | GCCTTGGTGAGAAGATCAAGTTCTTGAAGTG (SEQ ID NO:48) | nested reverse primer specific for PatTpsC-16 |
| PatBF2 3'R1 | AATGTTACCATTTGCTAGACAACGATTGGTG (SEQ ID NO:49) | forward primer specific for PatBF2 |
| PatBF2 3'R2 | GGAGACATACTTCTGGGACGCTGGAGTAG (SEQ ID NO:50) | nested forward primer specific for PatBF2 |
| PatCF2 3'R1 | GAGTCTTACTTTTGGGCAGTGGGAGTGTACTATC (SEQ ID NO:51) | forward primer specific for PatCF2 |
| PatCF2 3'R2 | CCCAAGTACTCTCGTGCCCGTATTATGC (SEQ ID NO:52) | nested forward primer specific for PatCF2 |
| PatTpsB15 5R1 | CCATTGGAAGGCTTGTGGGGTGGC (SEQ ID NO:53) | reverse primer specific for PatTpsB-15 |
| PatTpsB15 5R2 | CTCTCAATTTCTTCAAACACGTCCAAAACCAG (SEQ ID NO:54) | nested reverse primer specific for PatTpsB-15 |
| PatTpsC16 5R1 | GCGGTGGAGGTGATGAGAGAAATCC (SEQ ID NO:55) | reverse primer specific for PatTpsC-16 |
| PatTpsC16 5R2 | GAAATTGCTGATGGAGTTCCAACAACACTC (SEQ ID NO:56) | nested reverse primer specific for PatTpsC-16 |
| PatF1 | TVGACRCAMTMSARCGHCTDGG (SEQ ID NO:57) | forward degenerated primer deduced from the patchouli terpene synthase. |
| PatF2 | RATVVMCTYCCWGAKTAYATS (SEQ ID NO:58) | |
| PatR1 | CCTCRTTHAHDKYCTTCCATBC (SEQ ID NO:59) | reverse degenerated primer deduced from the patchouli terpene synthase |
| PatR2 | SCATAWKHRTCRWADGTRTCATC (SEQ ID NO:60) | |
| Pat177-5R1 | GGGCCTCTTCCATGTAAGCTCTCGCGGCG (SEQ ID NO:61) | reverse primer specific for Pat177 |
| Pat177-5R2 | GGCTTCTTTTCCATAGTAGGCTCGATATGGTGCG (SEQ ID NO:62) | nested reverse primer specific for Pat177 |
| Pat177-3R1 | GCCAGGCTCGTCAATGATATTACGGGACAC (SEQ ID NO:63) | primer specific for Pat177 |
| Pat177-3R2 | CACGAGTTTGAGAAAAAACGAGAGCACGTTCGC (SEQ ID NO:64) | nested primer specific for Pat177 |
| PatTpsA Nde | GGCATATCCATATGGCTGCTTTTACTGCTAATGCT GTTG (SEQ ID NO:65) | forward primer for expression of PatTpsA in pET11a |
| PatTpsA Bam | CGCGGATCCTCAAATGCGTAGAGGGTTAACAAA AAGGG (SEQ ID NO:66) | reverse primer for expression of PatTpsA in pET11a |
| PatTpsA topo | CACCATGGCTGCTTTTACTGCTAATGC (SEQ ID NO:67) | forward primer for expression of PatTpsA in pET102 |
| PatTpsA stop | TCAAATGCGTAGAGGGTTAACAAAAAGGGC (SEQ ID NO:68) | reverse primer for expression of PatTpsA in pET102 |
| PatTpsBF2.1 topo | CACCATGGAATTGAAAAACCAAAGTGTTGC (SEQ ID NO:69) | forward primer for expression of PatTpsBF2 in pET101 |
| PatTpsBF2.1 stop | CTATGGAATAGGGTGAATATATAGTTGCTTGATG (SEQ ID NO:70) | reverse primer for expression of PatTpsBF2 in pET101 |

TABLE 1-continued

| Name | Sequence (5' to 3') | Description |
|---|---|---|
| PatTpsCF2 topo | CACCATGGCTGTACAAATCTCCGAAACTG (SEQ ID NO:71) | forward primer for expression of PatTpsCF2 in pET101 |
| PatTpsCF2 stop | TTAAAGCTTGATCTGATCAACAAACAGAGC (SEQ ID NO:72) | reverse primer for expression of PatTpsCF2 in pET101 |
| PatTpsB15 topo | CACCATGGATTTGAATGAAATCACC (SEQ ID NO:73) | forward primer for expression of PatTpsB15 in pET101 |
| PatTpsB15 stop | TTAAGGAATAGGGTGAATGTATAGTTGG (SEQ ID NO:74) | reverse primer for expression of PatTpsB15 in pET101 |
| PatTps177 topo | CACCATGGAGTTGTATGCCCAAAGTG (SEQ ID NO:75) | forward primer for expression of PatTps177 in pET101 |
| PatTps177 stop | TTAATATGGAACAGGGTGAAGGTAC (SEQ ID NO:76) | reverse primer for expression of PatTps177 in pET101 |

Example 9

Heterologous Expression and Characterization of Enzymatic Activity

For the biochemical characterization of the sesquiterpene synthases for which the full-length cDNA was isolated, the cDNA was ligated into appropriate expression plasmids. This plasmid were used to transform *E coli* cells and after expression of the recombinant proteins, the *E coli* proteins were extracted and used to evaluate the biochemical conversion of FPP to sesquiterpene compounds (see Examples 5 and 6).

PatTpsA: The PatTpsA cDNA was ligated in the pET1 a expression plasmid (Examples 5 and 6). Heterologous expression in the commercially available *E. coli* strain BL21 (DE3) yielded only small amounts of functional soluble recombinant proteins and large amounts of insoluble proteins (sesquiterpene synthases are soluble proteins and the insoluble proteins reflect inactive proteins that precipitate as inclusion bodies). Several attempts were made to improve the fraction of soluble sesquiterpene synthase protein by slowing down the protein synthesis to facilitate the correct folding (low temperature of culture, low concentration of inducer). No significant improvement was observed.

PatTpsA was also ligated in the pET102 plasmid that allowed the expression of the sesquiterpene synthase as a fusion protein with a thioredoxin protein. Thioredoxin promotes the formation of disulfides bounds during protein folding. This type of fusion as been shown to improve the correct folding and solubilization of expressed proteins. The expression of PatTpsA using this system did not improve the expression of functional proteins.

Consequently, for PatTpsA the enzymatic activity found in the recombinant *E. coli* protein extract was low, but the biosynthesis of small amounts of sesquiterpenes was detected. GC-MS analysis and calculation of the retention index (KI) allowed the identification of γ-curcumene as the major sesquiterpene produced (FIG. 7). Production of several minor sesquiterpenes can not be excluded, but because of the low activity they could not be identified.

This constitutes the first report of cloning of a cDNA encoding for a γ-curcumene synthase. γ-curcumene was not detected in patchouli oil. It could be possible that this compound is present in very low concentration or that it is converted to other compounds.

PatTpsBF2: The PatTpsBF2 cDNA was ligated in pET101 plasmid (Example 4). After transformation of BL21 Star™ (DE3) *E. coli* cells (Invitrogen) and induction of the expression, only small amounts of soluble recombinant protein were detected. As for PatTpsA, expression using the pET102 plasmid (expression as fusion to the thioredoxin protein) did not improve the expression of functional proteins. Sesquiterpene synthase activity could be detected with crude protein extract from *E. coli* expressing the PatTpsBF2 protein (FIG. 8). Only one sesquiterpene product, (−)-germacrene D, could be identified (confirmed by the mass spectrum and the retention index). Germacrene D was never detected in patchouli oil and could be present as trace constituent or could be converted to another compound in the plants. A germacrene D synthase cDNA has previously been isolated from tomato (van der Hoeven, R. S., Monforte, A. J., Breeden D., Tanksley, S. D., and Steffens J. C. (2000) The Plan cell 12, 2283-2294) but, when including all minor products, the overall product profile appears to be different.

Figure 9:
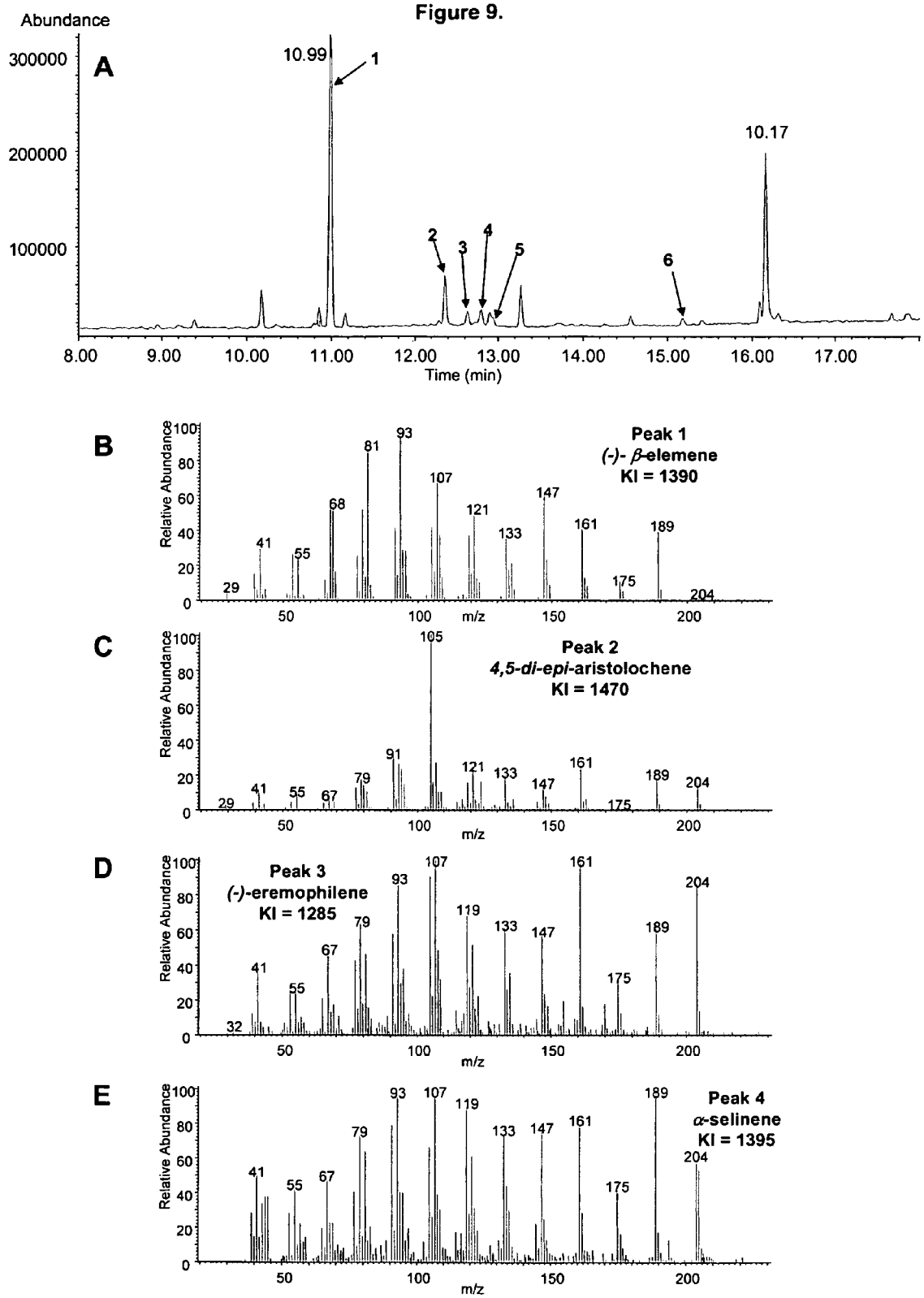
FIG. 9: Coupled gas chromatographic-mass spectrophotometric (GC-MS) analysis of sesquiterpenes produced by Pat-TpsCF2 (SEQ ID NO:8). A. Total ion chromatogram. The peak of farnesol (retention time 16.16) is due to hydrolysis of FPP by the *E. coli* alkaline phosphatase present in the crude protein extract. Peaks marked with number are sesquiterpenes. B, C, D, E. Mass spectra and calculated retention indexes of the peaks were the sesquiterpene was identified. Peak 5 is a sesquiterpene hydrocarbon and peak 6 is a sesquiterpene alcohol. For structure of the molecules, see FIG. 1.

PatTpsCF2: The PatTpsCF2 cDNA was ligated in the pET101 plasmid and the BL21 Star™ (DE3) *E coli* cells were transformed with this construct. Relatively large amounts of recombinant protein were obtained and the sesquiterpene synthase activity was easily detected. After incubation with farnesyl pyrophosphate, several sesquiterpenes could be separated by GC-MS (FIG. 9). The major peak could be identified as (−)-β-element. This compound is formed by thermal rearrangement (Cope rearrangement) of (+)-germacrene A in the hot injector of the GC. Thus PatTpsCF2 is a sesquiterpene synthase producing as main compound (+)-germacrene A. Other minor sesquiterpenes were also detected and some of them, i.e. 4,5-di-epi-aristolochene, (−)-eremophilene and α-selinene, were tentatively identified (FIG. 9). (−)-β-element was detected as minor constituent in some patchouli oil analysis meaning that (+)-germacrene A is present in the oil. Germacrene A is a sesquiterpene relatively ubiquitous in plant species. cDNAs encoding for germacrene synthases have been isolated from several plant species including Lettuce, Chicory and Goldenrod (Bennett, M. H., et al. (2002) Phytochem. 60, 255-261; Bouwmeester, H. J., et al. (2002) Plant Physiol. 129 (1), 134-144; Prosser I, et al. (2002) Phytochem. 60, 691-702).

Figure 10:
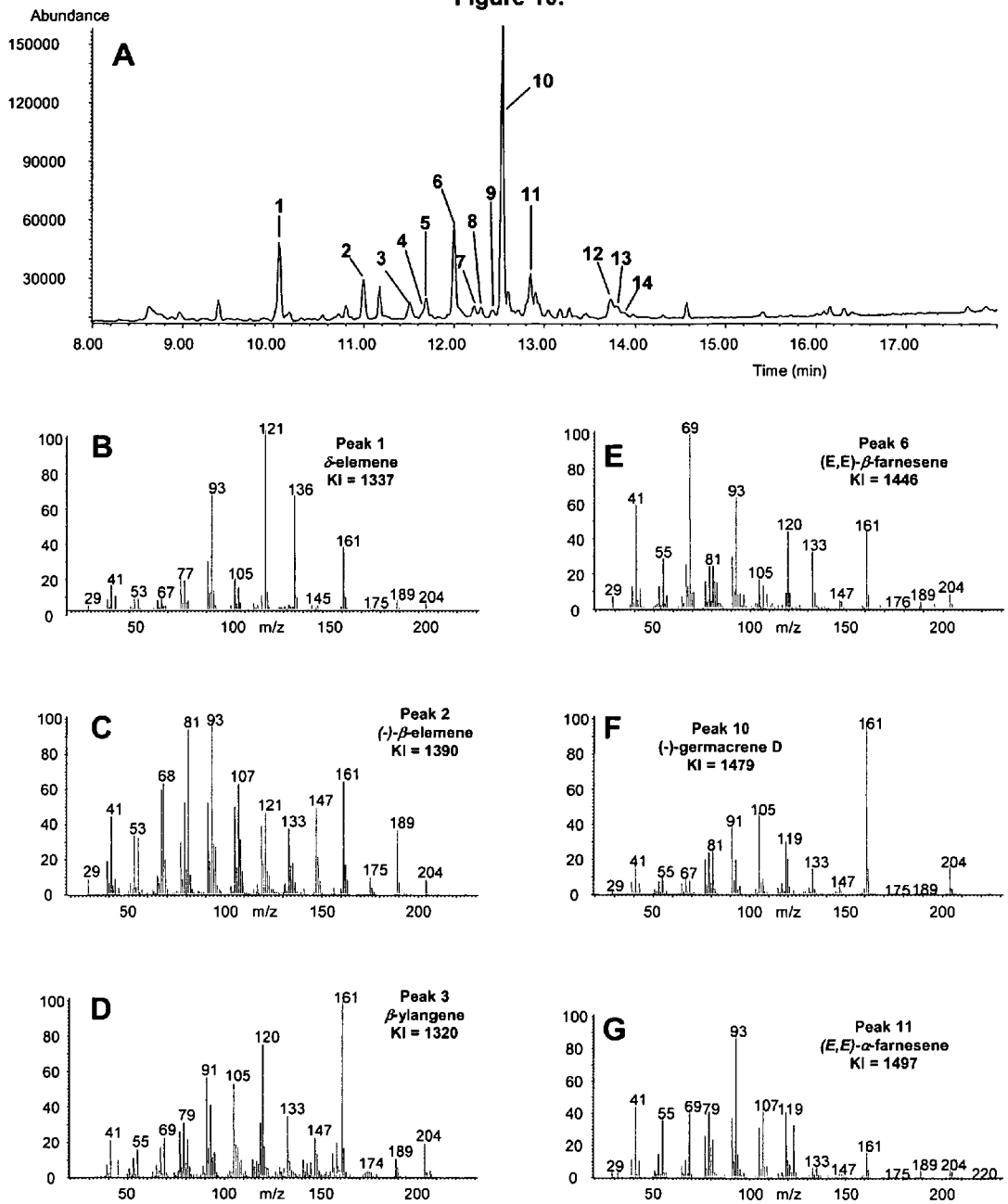
FIG. 10: Coupled gas chromatographic-mass spectrophotometric (GC-MS) analysis of sesquiterpenes produced by PatTpsB-15 (SEQ ID NO:9). A. Total ion chromatogram. Peaks marked with number are sesquiterpenes. B, C, D, E, F, G. Mass spectra and calculated retention indexes of the peaks were the sesquiterpene was identified. Peak 4, 5, 7, 8, 9 and 12 are sesquiterpene hydrocarbons. Peaks 13 and 14 are sesquiterpene alcohols. For structure of the molecules, see FIG. 1.

PatTpsB15: The PatTpsB15 cDNA was ligated in the pET101 plasmid and the BL21 Star™ (DE3) *E coli* cells were transformed. Enzyme assays with crude *E. coli* proteins extracted after induction of the expression of the recombinant sesquiterpene synthase, showed relatively good metabolization of FFP. Several sesquiterpenes were detected by GC-MS (FIG. 10). The main product was identified (by mass spectrum and retention index) as (−)-germacrene D. δ-element, (−)-β-element (the thermal rearrangement products of germacrene C and (+)-germacrene A respectively), β-ylangene, (E,E)-β-farnesene and (E,E)-α-farnesene could also be identified among the minor products formed by the recombinant PatTpsB15. At least eight other sesquiterpenes were produced but their structure could not be unambiguously determined. The PatTpsB15 sesquiterpene synthases has an activity similar to the activity of PatTpsBF2 with the main product formed being (−)-germacrene D. But when including all products formed, the catalytic activity of these two enzymes appears to be significantly different.

Figure 11:
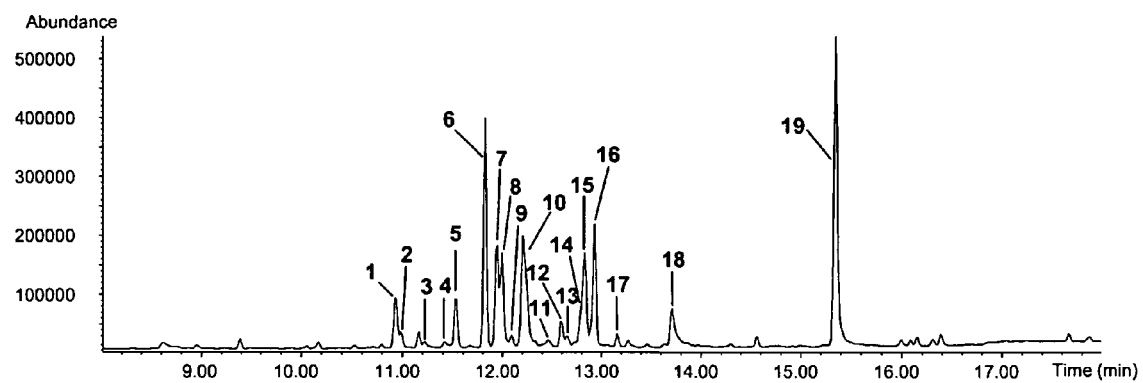
FIG. 11: Coupled gas chromatographic-mass spectrophotometric (GC-MS) analysis of the sesquiterpenes produced by PatTps177 (SEQ ID NO:10). The total ion chromatogram is represented. Peaks marked with number are sesquiterpenes. All sesquiterpenes in the marked peaks, except peaks 3, 4, 11, 13 and 17, could be identified.
Figure 12:
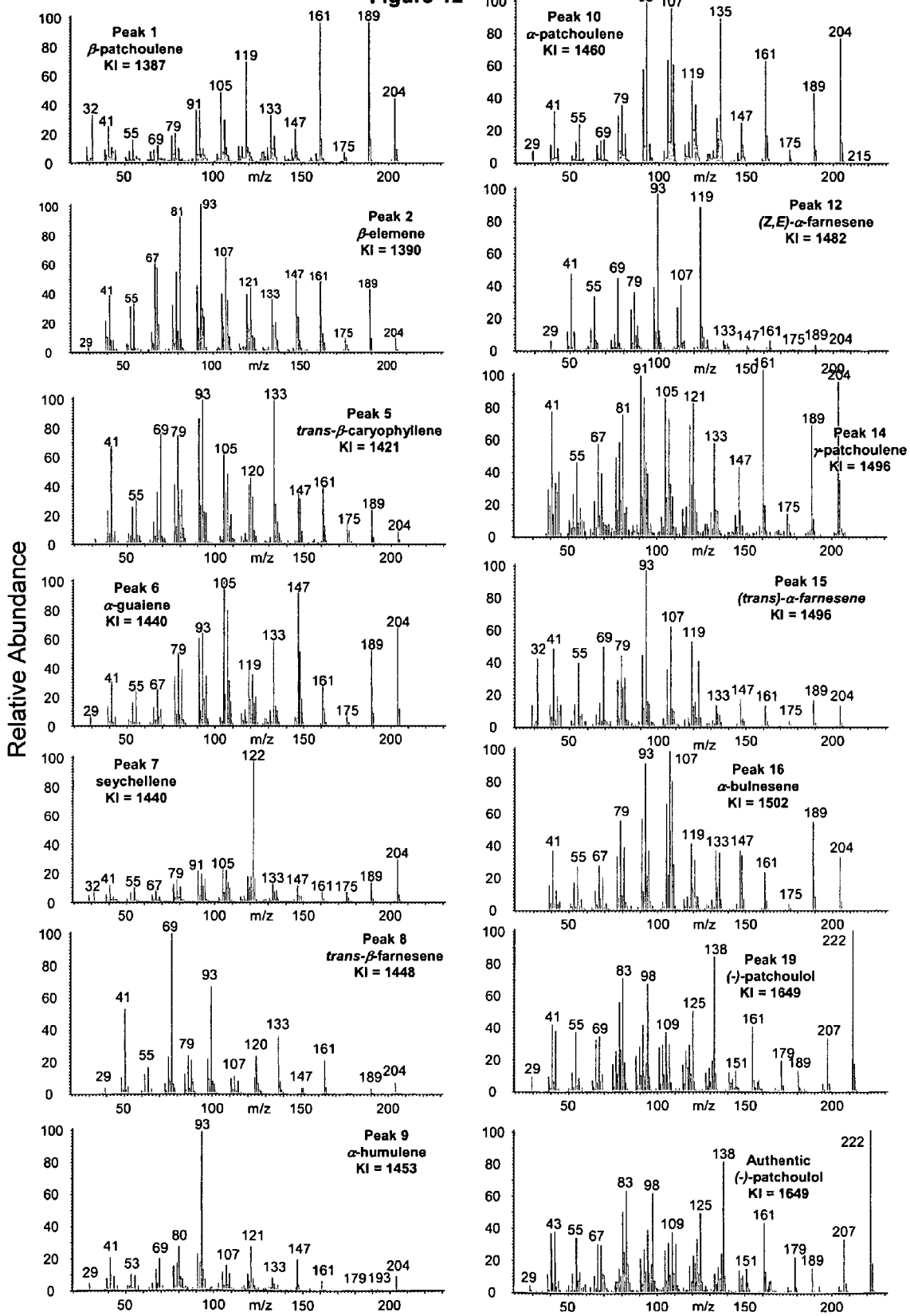
FIG. 12: Mass spectra of selected peaks from the coupled gas chromatographic-mass spectrophotometric (GC-MS) analysis of the sesquiterpenes produced by PatTps177 (SEQ ID NO:10). The mass spectrum, the name of the compound and the calculated retention index are shown for each peak where the sesquiterpene was identified. The mass-spectrum of the authentic standard of (−)-patchoulol (purified from patchouli oil) is also presented. For structure of the molecules, see FIG. 1.

PatTps177: The PatTps177 cDNA was ligated in the pET101 plasmid, BL21 Star™ (DE3) *E coli* cells were transformed and expression of the recombinant sesquiterpene synthase was induced. Enzymatic assay using the crude protein extract and FPP as substrate showed that PatTps177 was the patchoulol synthase. The enzyme produced as main product (−)-patchoulol and at least 18 other sesquiterpenes (FIGS. 11 and 12). Most of the sesquiterpenes produced by the enzymes could be identified by GC-MS and the amounts estimated by GC (flame ionization detection): (−)-patchoulol (39.1%), β-patchoulene (2.1%), (+)-germacrene A (detected as the thermal rearrangement product β-element) (1.6%), trans-β-caryophyllene (4.5%), alpha-guaiene (14%), seychellene (4%), trans-β-farnesene (3%), alpha-humulene (1.1%), α-patchoulene (8.9%), (Z,E)-α-farnesene (1.35%), γ-patchoulene (2.5%), (trans)-alpha-farnesene (3%) and α-bulnesene (8.6%). All the sesquiterpene produced by the recombinant patchoulol synthase are found in patchouli oil analysis, in approximately the same proportions, except for the farnesane sesquiterpenes. The product profile of the recombinant patchoulol synthase shows that one single sesquiterpene synthase is responsible for the production of the major and most characteristic sesquiterpenes found in patchouli plants.

Example 10

In vivo Biosynthesis of Patchoulol

Bacteria use the DXP pathway to produce isoprenoids essential for functions such as tRNA prenylation, and biosynthesis of quinones and dolichols. Thus, in the *E. coli*, cells, FPP is present as and intermediate and at least part of the pool should be usable by sesquiterpene synthases expressed in these cells.

Experiments were performed using *E. coli*, to test the ability of the patchoulol synthase to synthesise, in vivo, sesquiterpenes from the endogenous FPP pool. Typical experiments for evaluation of in vivo sesquiterpene production are performed as follows. The expression plasmid containing the sesquiterpene synthase cDNA are transformed in BL21 (DE3) *E. coli*, cells. Single colonies of transformed cells are used to inoculate 5 mL LB medium supplemented with the appropriate antibiotics. After 5 to 6 hours of incubation at 37° C., the culture were use to inoculate 100 ml TB medium supplemented with the appropriate antibiotics and the culture was incubated for 2 hours at 20° C. in a 250 mL shake flask. After 2 hours incubation, expression of the protein was induced by the addition of 1 mM IPTG. The cultures were left 24 hours and were then directly extracted twice with one volume of pentane. The two solvent fractions were recovered, combined and concentrated to 0.5 mL prior to GC-MS analysis. In the in vivo-sesquiterpene production assay, *E. coli*, cells expressing the patchoulol synthase (as described in exemple 9) produced patchoulol. Patchoulol could be clearly detected by GC analysis of the culture extract, and no patchoulol was detected with cells transformed with the empty plasmid. The identity of the product could be confirmed by GC-MS, but the amount of sesquiterpene produced was relatively low and estimation of the quantities was not possible.

This experiment have demonstrated that the patchoulol synthase is able to utilise endogenous FPP and produce patchoulol in vivo. The cDNA coding for the patchoulol synthase can thus be used to engineer organism for in vivo production of patchoulol.

SEQUENCE LISTING

```
<160> NUMBER OF SEQ ID NOS: 10

<210> SEQ ID NO 1
<211> LENGTH: 1638
<212> TYPE: DNA
<213> ORGANISM: Pogostemon cablin

<400> SEQUENCE: 1
atggctgctt ttactgctaa tgctgttgat atgaggcctc ctgtcatcac cattcatccc      60
cgttccaaag atatcttctc tcagtttcc ttggacgata agcttcagaa gcagtacgca     120
caaggaattg aagctctgaa ggaagaagca agaagcatgt taatggctgc aaaatcagcc     180
aaagtcatga tactaataga cacactcgag cgtctgggat taggatatca ttttgagaag     240
gagatcgaag agaaactcga agcaatatac aagaaggaag atggtgacga ctatgatttg     300
```

-continued

```
ttcactactg cgcttagatt tcgtctgctc aggcaacatc agcgccgtgt tccctgcagt    360
gtttttgata agtttatgaa caaagagggc aagtttgagg aagaacccct tgattagtgat   420
gtggagggac tactgagtct gtatgatgca gcctacctgc agatccatgg ggaacacatc    480
ttgcaagaag ccctaatttt cacaacacat catttaactc gtatcgagcc acaattagac    540
gatcactctc cccttaaact caaactgaat cgagctttgg agtttccttt ttatcgagag    600
atccccatca tttatgcaca cttttacatc tccgtttacg agagggatga ctctagagat    660
gaagtgcttc tcaaaatggc aaaattgagc tacaatttct tgcaaaattt gtacaagaaa    720
gagctttctc aactctccag gtggtggaat aaattagaac taataccaaa cctaccatat    780
ataagagaca gcgtggcggg tgcctatctt tgggctgtag cattatattt cgaacctcaa    840
tattctgatg tccgaatggc cattgccaaa ttaatacaaa ttgctgctgc agtagatgat    900
acatacgata attatgcgac cattcgagaa gctcaacttc ttactgaagc tttggagagg    960
ttgaatgtgc atgaaattga tacccttcct gattatatga aaattgttta tcgtttcgtt   1020
atgagttggt cagaagattt cgaacgagat gcaacaatta agaacagat gcttgcaact   1080
ccctacttca aagcggagat gaaaaaactt ggaagggctt acaatcaaga gctgaagtgg   1140
gttatggaaa ggcaattgcc ttcatttgaa gaatatatga aaaattctga gattacgagt   1200
ggtgtgtata taatgttcac tgtcatttca ccatacttga attctgctac acaaaaaaac   1260
attgattggt tgctgagtca acctcgtctc gcttcatcca ctgccatagt tatgagatgc   1320
tgcaatgact gggcagcaa tcaacgcgag agcaagggtg gagaagtgat gacttccctg   1380
gattgctaca tgaaacaaca tggtgcatca aagcaagaaa ccatatctaa atttaaacta   1440
ataattgagg atgaatggaa gaatttgaac gaggaatggg cagcgaccac ttgtttgcca   1500
aaagtaatgg tggagatatt tcgcaactac gcaagaattg caggtttctg ttacaaaaac   1560
aatggagatg cttatacgag tcccaaaata gttcagcaat gttttgatgc cctttttgtt   1620
aaccctctac gcatttga                                                  1638
```

<210> SEQ ID NO 2
<211> LENGTH: 1665
<212> TYPE: DNA
<213> ORGANISM: Pogostemon cablin

<400> SEQUENCE: 2

```
atggaattga aaaccaaag tgttgcaata atctccagca atgcttctcg cccacttgcg     60
cattatcatc cagacgtatg gggagatcgt ttccttctct acaaaccaaa tcccagttct   120
gaggctggtc agaaaccagt tattgaagag ctgaaacagc aagtgagaag cgagctgaag   180
gaagcatcga acgactacat gcgacagctg aagatggtgg acgcaataca acgacttggc   240
atcgagagtc tctttgagga agacattgat aatgcattga gaatctgtc tgaaaatttt   300
gatgattact gcaaagataa gcatgatttg tatgccattg ctcttagctt tcgccttctc   360
agacaacatg gatacaggat tcatgtgat gtattcgaca gttgaagga tggcgaagat     420
ggattcaaag ttcccccttc agatgaagcg cttgcagttg tagagttgtt agaggccacg   480
catctaagaa tccatggaga agttgtgctt gatcgtgcct tgttttcgc caggattcac    540
cttgaatcga ttgaagcaaa tttgaataat ccagtcgcga acaagttca taacgcgttg    600
tatggatact ctaatcggag aggaatgcaa caagtagaag cgaggaagta catacccatc   660
tacgagcaat atgcttctca tcatcaaggc ttgctcaaac ttgctacgct gaattttaac   720
ctgcaacaaa ccatgcacaa aagggagttg agtgaacttt caaggtggta tagagattta   780
```

-continued

```
gaagttccaa caatgttacc atttgctaga caacgattgg tggagacata cttctgggac    840
gctggagtag tttttgaacc agaaaatgat gttgccagga tgattttagt caaagtgcaa    900
tgcctaatct ctttcttga tgatactttt gatgcatatg gaagttttga ggaactacaa    960
ctcttcacgg atgcaattaa tacatgggat gtttcatgtt tagatcaact tccagattat   1020
atgaagataa tttacaaagc ccttttggga gtgtttgaag taattgagaa actaatgatc   1080
aaacaaggaa cattgtatcg tctcaactat gcaaaagaag cgatgaaaat agtggtggga   1140
ggttactttg ttgaggctaa atggagggaa gaaaagagca acccacgac gcaagagtac    1200 atgcaggtag caacaaagag tgcaggatat atgactctta ttataacatc atttcttgga   1260
atggaagcaa atattgccac caaagaagcc ttcgattggg tgctttctga gcctgatgtt   1320
atgaaagctg caataactct tgccaggctc accaatgata tcgtcggaat tgagctcgag   1380
aaagaaagaa agcatatagc tacagcagtg gaagtgtacg aggacgagca taaattgtcc   1440
atgcaagagg ccatggttga aatcaagaat caaatcgagt cgggatggaa gaccataaat   1500
gaggcgtttc ttagaccaac taaatttcca acacctatac tttatcgtat actcaattac   1560
tgcagagttc ttgaggttat ttacgacaag agcgatcgct acacacatgt ggatcctgca   1620
ttgcaagaca tcatcaagca actatatatt caccctattc catag                    1665
```

<210> SEQ ID NO 3
<211> LENGTH: 1665
<212> TYPE: DNA
<213> ORGANISM: Pogostemon cablin

<400> SEQUENCE: 3

```
atggctgtac aaatctccga aactgttcgc cctttcgcca attttctcc caatcccagc      60 ttgtggggtg atcaattcat caaccacaaa tctaaaactc agcaaatatc gaggatatat    120
ttggaggaaa ttgaagggtt gaaaatgaa gtaaagtgta tgctaacaag taccccagag    180
ggaaagatgg cggacaccgt caacctgatc gacacactcg agcgcctagg ggtatcgtat    240
catttcgaaa aggaaatcga agagaagatg aaacacttat tcaatctgat caaagcggat    300
aactataaag atcatgaagg ctgtgatttg tatactgatg ctcttcattt tcgattattc    360
aggcagcatg gttaccctat atcttctggg attttaaca aatggatgga tgggaatgga    420
aaattcaagg agagcattaa gagtgatgca aagggtttgt tgagcttgta tgaagcatgc    480
tgtttgagaa cacatggaga caccctactc gacgaagccc ttgttttgc tacggccagt    540 ctgaaatcca tggcagcaaa ccttgcgtca cccctaagga aacaggttga gcatgccctc    600
ttccagcact tgcattttgg cattccaaga gtcgaagcac gacacttcat caccttctac    660
gaagaggaag agcacaagaa tgagatgctg cttaggttcg ccaaattgga ctttaatgca    720
ttgcaagcac tgcacaaaga ggagctgagt gaaatcagca agtggtggaa agatttggat    780
ctcatctcga aacttccata tgcaagagac agggtggtag agtcttactt tgggcagtg    840 ggagtgtact atcaacccaa gtactctcgt gcccgtatta tgctcactaa aaccattgcc    900
atgacggcta tattgatga cacctatgac tcttatggta cacttgaaga acttgatgtt    960
ctcacaaagg caattgagag gtgggatatc aaagaaatta tggactccc agagtacatc   1020 aaaggattct ataaacaggt gctgaaactc tatcagcaat tagaggaaga attagcaaag   1080
gaaggaagat cttatgctgt atactatgca atagaagctt gtaaggaatt ggcgaggagc   1140
tacgctgtgg aggcgaagtg gttcaagaaa gggtacttgc ccggatttga ggagtaccta   1200
atcaattctc tcgtcaccctc cacggctggc tatctcaata taatctcgtt ttttggcgtg   1260
```

-continued

```
gaatctgtaa ccaaggaaga ttttgaatgg tttagcaaga agcctagaat cgctgtagcc    1320
actcagataa ttacaagagt tatcgatgac attgcaactt atgaggtaga gaaggagaag    1380
ggtcagagtg ccacaggaat agattgctac atgaaggaac atggggtgag caaagagaag    1440
gcaatgcaga gattctatga atgagtacc aatgcatgga aggatattaa tgaggaaggc     1500
ctcagttggc catcttcttt ttccagggat attttcgtcc aactccgaaa ttttagtcgc    1560
atggttgatg ttacctatgg caaaaatgaa gatggatact ccaaacccga aaagattctc    1620
aagccactta tcattgctct gtttgttgat cagatcaagc tttaa                    1665
```

<210> SEQ ID NO 4
<211> LENGTH: 1638
<212> TYPE: DNA
<213> ORGANISM: Pogostemon cablin

<400> SEQUENCE: 4

```
atggatttga atgaaatcac ctcttcatct cgtcctctcg caaattatca cccaaatgtg     60
tggggagacc gtttccttct gcatgaacca gaattcactt gccaggctgg tgagaaacaa    120
ctagttgaag agctgaaaga ggaagtgaga agggagctga aggaagcgtc gaacgactac    180
cttcgacagc tgaagatggt ggacgcaata aacgactag gcatcgagta tctctttgag     240
gaagagatta tgaagctct gagaaatctg ttggcaaaat tcgagaatta ttgcaaggat     300
aatcatgata tgtacgccac tgctcttagc tttcgccttc tcagacaaca cggatacaag    360
gtttcatgtg aagtttttga caagtttaag gatggggaag atggattcaa ggtggaagaa    420
gtgatggcag ttctcgagtt gtttgaggct acacatatga gaattcatgg agaagatgtg    480
ctcgatcaag cctttgtttt cacaaggaat taccttcaat caattcacgc aaccttgagt    540
aatccaattg ctaaacaagt tcacaacgca ttgaatggat actcttgtcg agaggaatg     600 ccacgaatcg aagcgaggaa gtatatacc atctacgagg aatacggttg tcaccataaa    660
gccttgctca aacttgctaa gctcgatttc aatctacttc aatctatgca caaaagggag   720
ttgactcaac tttataggtg gtggaaagat ttggaaatgc caacaaagct accgtacata    780
agagatcgat tggtggagac atactttggg gacatggggt tttattttga accacaatat    840
gctctagcta gaaatatctt agtcaaagta caatgtttgg tgtctatttt cgatgacact    900
tttgatgcat atggtgcttt taaggaatta caactcttca agatgccat tgatagatgg    960 agtatctcat gcttagatga acttccagag tatatgcaga taatctacaa actggttttg   1020
gacgtgtttg aagaaattga gagtcatatg atcaaacaag gaacatcgta tcgtctggac   1080
tatgcaagaa aagcgataaa aattgtgatt ggaggttact ttgatgaggc aaaatggagg   1140
gaagaagagt acaagccaag aatggaagag tacatgaaag tagctacaaa gagtgcagcc   1200
tacttaactc taatcatagt atcatttgta gggatgaaaa atgacattgc cacccccacaa 1260 gccttccaat gggtcctttc tgaacctcaa attattacag cttctttagc tcttgccagg   1320
ctctccaatg atctcgtggg cattgagttt gagaaagaga gaagtatat agcgacagca    1380 gtggagttgt acgaggaaga gcataaagtg tcaaaagaag aggctgtgtt ggaattgagg   1440
catgaaacag agtcggcatg gaaggaaatt aatgaggcgt tgttagagcc aactacattt   1500
gcgaccccaa ttcttgatcg tatacttaat tccgcccgag tacttgaagt ttttttacgac 1560 aagaccgacc gctacacaca tgtggatctt gaattgcaga atatcatcgc ccaactatac   1620
attcacccta ttccttaa                                                  1638
```

<210> SEQ ID NO 5
<211> LENGTH: 1659
<212> TYPE: DNA
<213> ORGANISM: Pogostemon cablin

<400> SEQUENCE: 5

```
atggagttgt atgcccaaag tgttggagtg ggtgctgctt ctcgtcctct tgcgaatttt      60
catccatgtg tgtggggaga caaattcatt gtctacaacc acaatcatg ccaggctgga     120
gagagagaag aggctgagga gctgaaagtg gagctgaaaa gagagctgaa ggaagcatca     180
gacaactaca tgcggcaact gaaaatggtg gatgcaatac aacgattagg cattgactat     240
cttttttgtgg aagatgttga tgaagctttg aagaatctgt ttgaaatgtt tgatgctttc     300
tgcaagaata tcatgacat gcacgccact gctctcagct tcgccttct cagacaacat     360
ggatacagag tttcatgtga agttttgaa agtttaagg atggcaaaga tggatttaag      420
gttccaaatg aggatggagc ggttgcagtc cttgaattct cgaagccac gcatctcaga      480
gtccatggag aagacgtcct tgataatgct tttgacttca ctaggaacta cttggaatca     540
gtctatgcaa ctttgaacga tccaaccgcg aaacaagtcc acaacgcatt gaatgagttc     600
tcttttcgaa gaggattgcc acgcgtggaa gcaaggaagt acatatcaat ctacgagcaa     660
tacgcatctc atcacaaagg cttgctcaaa cttgctaagc tggatttcaa cttggtacaa     720
gctttgcaca gaagggagct gagtgaagat tctaggtggt ggaagacttt acaagtgccc     780
acaaagctat cattcgttag agatcgattg gtggagtcct acttctgggc ttcgggatct     840
tatttcgaac cgaattattc ggtagctagg atgattttag caaaagggct ggctgtatta     900
tctcttatgg atgatgtgta tgatgcatat ggtacttttg aggaattaca aatgttcaca     960
gatgcaatcg aaaggtggga tgcttcatgt ttagataaac ttccagatta catgaaaata    1020
gtatacaagg ccctttttgga tgtgtttgag gaagttgacg aggagttgat caagctaggc    1080
gcaccatatc gagcctacta tggaaaagaa gccatgaaat acgccgcgag agcttacatg    1140
gaagaggccc aatggaggga gcaaaagcac aaacccacaa ccaaggagta tatgaagctg    1200
gcaaccaaga catgtggcta cataactcta ataatattat catgtcttgg agtggaagag    1260
ggcattgtga ccaaagaagc cttcgattgg gtgttctccc gacctccttt catcgaggct    1320
acattaatca ttgccaggct cgtcaatgat attacaggac acgagtttga gaaaaaacga    1380
gagcacgttc gcactgcagt agaatgctac atggaagagc acaaagtggg gaagcaagag    1440
gtggtgtctg aattctacaa ccaaatggag tcagcatgga aggacattaa tgagggttc     1500
ctcagaccag ttgaatttcc aatccctcta ctttatctta ttctcaattc agtccgaaca    1560
cttgaggtta tttacaaaga gggcgattcg tatacacacg tgggtcctgc aatgcaaaac    1620
atcatcaagc agttgtacct tcaccctgtt ccatattaa                           1659
```

<210> SEQ ID NO 6
<211> LENGTH: 545
<212> TYPE: PRT
<213> ORGANISM: Pogostemon cablin

<400> SEQUENCE: 6

```
Met Ala Ala Phe Thr Ala Asn Ala Val Asp Met Arg Pro Pro Val Ile
1               5                   10                  15

Thr Ile His Pro Arg Ser Lys Asp Ile Phe Ser Gln Phe Ser Leu Asp
            20                  25                  30

Asp Lys Leu Gln Lys Gln Tyr Ala Gln Gly Ile Glu Ala Leu Lys Glu
        35                  40                  45
```

```
Glu Ala Arg Ser Met Leu Met Ala Ala Lys Ser Ala Lys Val Met Ile
 50                  55                  60

Leu Ile Asp Thr Leu Glu Arg Leu Gly Leu Gly Tyr His Phe Glu Lys
 65                  70                  75                  80

Glu Ile Glu Glu Lys Leu Glu Ala Ile Tyr Lys Lys Glu Asp Gly Asp
                 85                  90                  95

Asp Tyr Asp Leu Phe Thr Thr Ala Leu Arg Phe Arg Leu Leu Arg Gln
             100                 105                 110

His Gln Arg Arg Val Pro Cys Ser Val Phe Asp Lys Phe Met Asn Lys
         115                 120                 125

Glu Gly Lys Phe Glu Glu Pro Leu Ile Ser Asp Val Glu Gly Leu
 130                 135                 140

Leu Ser Leu Tyr Asp Ala Ala Tyr Leu Gln Ile His Gly Glu His Ile
145                 150                 155                 160

Leu Gln Glu Ala Leu Ile Phe Thr Thr His His Leu Thr Arg Ile Glu
                 165                 170                 175

Pro Gln Leu Asp Asp His Ser Pro Leu Lys Leu Lys Leu Asn Arg Ala
             180                 185                 190

Leu Glu Phe Pro Phe Tyr Arg Glu Ile Pro Ile Tyr Ala His Phe
                 195                 200                 205

Tyr Ile Ser Val Tyr Glu Arg Asp Asp Ser Arg Asp Glu Val Leu Leu
210                 215                 220

Lys Met Ala Lys Leu Ser Tyr Asn Phe Leu Gln Asn Leu Tyr Lys Lys
225                 230                 235                 240

Glu Leu Ser Gln Leu Ser Arg Trp Trp Asn Lys Leu Glu Leu Ile Pro
                 245                 250                 255

Asn Leu Pro Tyr Ile Arg Asp Ser Val Ala Gly Ala Tyr Leu Trp Ala
             260                 265                 270

Val Ala Leu Tyr Phe Glu Pro Gln Tyr Ser Asp Val Arg Met Ala Ile
         275                 280                 285

Ala Lys Leu Ile Gln Ile Ala Ala Val Asp Asp Thr Tyr Asp Asn
 290                 295                 300

Tyr Ala Thr Ile Arg Glu Ala Gln Leu Leu Thr Glu Ala Leu Glu Arg
305                 310                 315                 320

Leu Asn Val His Glu Ile Asp Thr Leu Pro Asp Tyr Met Lys Ile Val
             325                 330                 335

Tyr Arg Phe Val Met Ser Trp Ser Glu Asp Phe Glu Arg Asp Ala Thr
             340                 345                 350

Ile Lys Glu Gln Met Leu Ala Thr Pro Tyr Phe Lys Ala Glu Met Lys
         355                 360                 365

Lys Leu Gly Arg Ala Tyr Asn Gln Glu Leu Lys Trp Val Met Glu Arg
 370                 375                 380

Gln Leu Pro Ser Phe Glu Glu Tyr Met Lys Asn Ser Glu Ile Thr Ser
385                 390                 395                 400

Gly Val Tyr Ile Met Phe Thr Val Ile Ser Pro Tyr Leu Asn Ser Ala
             405                 410                 415

Thr Gln Lys Asn Ile Asp Trp Leu Leu Ser Gln Pro Arg Leu Ala Ser
         420                 425                 430

Ser Thr Ala Ile Val Met Arg Cys Cys Asn Asp Leu Gly Ser Asn Gln
         435                 440                 445

Arg Glu Ser Lys Gly Gly Glu Val Met Thr Ser Leu Asp Cys Tyr Met
 450                 455                 460
```

```
Lys Gln His Gly Ala Ser Lys Gln Glu Thr Ile Ser Lys Phe Lys Leu
465                 470                 475                 480

Ile Ile Glu Asp Glu Trp Lys Asn Leu Asn Glu Trp Ala Ala Thr
                    485                 490                 495

Thr Cys Leu Pro Lys Val Met Val Glu Ile Phe Arg Asn Tyr Ala Arg
                500                 505                 510

Ile Ala Gly Phe Cys Tyr Lys Asn Asn Gly Asp Ala Tyr Thr Ser Pro
                515                 520                 525

Lys Ile Val Gln Gln Cys Phe Asp Ala Leu Phe Val Asn Pro Leu Arg
                530                 535                 540

Ile
545

<210> SEQ ID NO 7
<211> LENGTH: 554
<212> TYPE: PRT
<213> ORGANISM: Pogostemon cablin

<400> SEQUENCE: 7

Met Glu Leu Lys Asn Gln Ser Val Ala Ile Ile Ser Ser Asn Ala Ser
1               5                   10                  15

Arg Pro Leu Ala His Tyr His Pro Asp Val Trp Gly Asp Arg Phe Leu
                20                  25                  30

Leu Tyr Lys Pro Asn Pro Ser Glu Ala Gly Gln Lys Pro Val Ile
            35                  40                  45

Glu Glu Leu Lys Gln Gln Val Arg Ser Glu Leu Lys Glu Ala Ser Asn
    50                  55                  60

Asp Tyr Met Arg Gln Leu Lys Met Val Asp Ala Ile Gln Arg Leu Gly
65                  70                  75                  80

Ile Glu Ser Leu Phe Glu Glu Asp Ile Asp Asn Ala Leu Lys Asn Leu
                85                  90                  95

Ser Glu Asn Phe Asp Asp Tyr Cys Lys Asp Lys His Asp Leu Tyr Ala
                100                 105                 110

Ile Ala Leu Ser Phe Arg Leu Leu Arg Gln His Gly Tyr Arg Ile Ser
                115                 120                 125

Cys Asp Val Phe Asp Lys Leu Lys Asp Gly Glu Asp Gly Phe Lys Val
130                 135                 140

Pro Pro Ser Asp Glu Ala Leu Ala Val Val Glu Leu Leu Glu Ala Thr
145                 150                 155                 160

His Leu Arg Ile His Gly Glu Val Val Leu Asp Arg Ala Phe Val Phe
                165                 170                 175

Ala Arg Ile His Leu Glu Ser Ile Glu Ala Asn Leu Asn Asn Pro Val
                180                 185                 190

Ala Lys Gln Val His Asn Ala Leu Tyr Gly Tyr Ser Asn Arg Arg Gly
                195                 200                 205

Met Gln Gln Val Glu Ala Arg Lys Tyr Ile Pro Ile Tyr Glu Gln Tyr
    210                 215                 220

Ala Ser His His Gln Gly Leu Leu Lys Leu Ala Thr Leu Asn Phe Asn
225                 230                 235                 240

Leu Gln Gln Thr Met His Lys Arg Glu Leu Ser Glu Leu Ser Arg Trp
                245                 250                 255

Tyr Arg Asp Leu Glu Val Pro Thr Met Leu Pro Phe Ala Arg Gln Arg
                260                 265                 270

Leu Val Glu Thr Tyr Phe Trp Asp Ala Gly Val Val Phe Glu Pro Glu
                275                 280                 285
```

-continued

```
Asn Asp Val Ala Arg Met Ile Leu Val Lys Val Gln Cys Leu Ile Ser
    290                 295                 300

Phe Leu Asp Asp Thr Phe Asp Ala Tyr Gly Ser Phe Glu Glu Leu Gln
305                 310                 315                 320

Leu Phe Thr Asp Ala Ile Asn Thr Trp Asp Val Ser Cys Leu Asp Gln
                325                 330                 335

Leu Pro Asp Tyr Met Lys Ile Ile Tyr Lys Ala Leu Leu Gly Val Phe
            340                 345                 350

Glu Val Ile Glu Lys Leu Met Ile Lys Gln Gly Thr Leu Tyr Arg Leu
        355                 360                 365

Asn Tyr Ala Lys Glu Ala Met Lys Ile Val Val Gly Gly Tyr Phe Val
370                 375                 380

Glu Ala Lys Trp Arg Glu Glu Lys Ser Lys Pro Thr Thr Gln Glu Tyr
385                 390                 395                 400

Met Gln Val Ala Thr Lys Ser Ala Gly Tyr Met Thr Leu Ile Ile Thr
                405                 410                 415

Ser Phe Leu Gly Met Glu Ala Asn Ile Ala Thr Lys Glu Ala Phe Asp
            420                 425                 430

Trp Val Leu Ser Glu Pro Asp Val Met Lys Ala Ala Ile Thr Leu Ala
        435                 440                 445

Arg Leu Thr Asn Asp Ile Val Gly Ile Glu Leu Glu Lys Glu Arg Lys
450                 455                 460

His Ile Ala Thr Ala Val Glu Val Tyr Glu Asp Glu His Lys Leu Ser
465                 470                 475                 480

Met Gln Glu Ala Met Val Glu Ile Lys Asn Gln Ile Glu Ser Gly Trp
                485                 490                 495

Lys Thr Ile Asn Glu Ala Phe Leu Arg Pro Thr Lys Phe Pro Thr Pro
            500                 505                 510

Ile Leu Tyr Arg Ile Leu Asn Tyr Cys Arg Val Leu Glu Val Ile Tyr
        515                 520                 525

Asp Lys Ser Asp Arg Tyr Thr His Val Asp Pro Ala Leu Gln Asp Ile
530                 535                 540

Ile Lys Gln Leu Tyr Ile His Pro Ile Pro
545                 550

<210> SEQ ID NO 8
<211> LENGTH: 554
<212> TYPE: PRT
<213> ORGANISM: Pogostemon cablin

<400> SEQUENCE: 8

Met Ala Val Gln Ile Ser Glu Thr Val Arg Pro Phe Ala Asn Phe Ser
1               5                   10                  15

Pro Asn Pro Ser Leu Trp Gly Asp Gln Phe Ile Asn His Lys Ser Lys
            20                  25                  30

Thr Gln Gln Ile Ser Arg Ile Tyr Leu Glu Glu Ile Glu Gly Leu Lys
        35                  40                  45

Asn Glu Val Lys Cys Met Leu Thr Ser Thr Pro Glu Gly Lys Met Ala
    50                  55                  60

Asp Thr Val Asn Leu Ile Asp Thr Leu Glu Arg Leu Gly Val Ser Tyr
65                  70                  75                  80

His Phe Glu Lys Glu Ile Glu Glu Lys Met Lys His Leu Phe Asn Leu
                85                  90                  95

Ile Lys Ala Asp Asn Tyr Lys Asp His Glu Gly Cys Asp Leu Tyr Thr
            100                 105                 110
```

-continued

```
Asp Ala Leu His Phe Arg Leu Phe Arg Gln His Gly Tyr Pro Ile Ser
            115                 120                 125

Ser Gly Ile Phe Asn Lys Trp Met Asp Gly Asn Gly Lys Phe Lys Glu
        130                 135                 140

Ser Ile Lys Ser Asp Ala Lys Gly Leu Leu Ser Leu Tyr Glu Ala Cys
145                 150                 155                 160

Cys Leu Arg Thr His Gly Asp Thr Leu Leu Asp Glu Ala Leu Val Phe
                165                 170                 175

Ala Thr Ala Ser Leu Lys Ser Met Ala Ala Asn Leu Ala Ser Pro Leu
            180                 185                 190

Arg Lys Gln Val Glu His Ala Leu Phe Gln His Leu His Phe Gly Ile
        195                 200                 205

Pro Arg Val Glu Ala Arg His Phe Ile Thr Phe Tyr Glu Glu Glu
210                 215                 220

His Lys Asn Glu Met Leu Leu Arg Phe Ala Lys Leu Asp Phe Asn Ala
225                 230                 235                 240

Leu Gln Ala Leu His Lys Glu Leu Ser Glu Ile Ser Lys Trp Trp
                245                 250                 255

Lys Asp Leu Asp Leu Ile Ser Lys Leu Pro Tyr Ala Arg Asp Arg Val
            260                 265                 270

Val Glu Ser Tyr Phe Trp Ala Val Gly Val Tyr Tyr Gln Pro Lys Tyr
        275                 280                 285

Ser Arg Ala Arg Ile Met Leu Thr Lys Thr Ile Ala Met Thr Ala Ile
290                 295                 300

Leu Asp Asp Thr Tyr Asp Ser Tyr Gly Thr Leu Glu Glu Leu Asp Val
305                 310                 315                 320

Leu Thr Lys Ala Ile Glu Arg Trp Asp Ile Lys Glu Ile Asn Gly Leu
                325                 330                 335

Pro Glu Tyr Ile Lys Gly Phe Tyr Lys Gln Val Leu Lys Leu Tyr Gln
            340                 345                 350

Gln Leu Glu Glu Glu Leu Ala Lys Glu Gly Arg Ser Tyr Ala Val Tyr
        355                 360                 365

Tyr Ala Ile Glu Ala Cys Lys Glu Leu Ala Arg Ser Tyr Ala Val Glu
370                 375                 380

Ala Lys Trp Phe Lys Lys Gly Tyr Leu Pro Gly Phe Glu Glu Tyr Leu
385                 390                 395                 400

Ile Asn Ser Leu Val Thr Ser Thr Ala Gly Tyr Leu Asn Ile Ile Ser
                405                 410                 415

Phe Phe Gly Val Glu Ser Val Thr Lys Glu Asp Phe Glu Trp Phe Ser
            420                 425                 430

Lys Lys Pro Arg Ile Ala Val Ala Thr Gln Ile Ile Thr Arg Val Ile
        435                 440                 445

Asp Asp Ile Ala Thr Tyr Glu Val Glu Lys Glu Lys Gly Gln Ser Ala
450                 455                 460

Thr Gly Ile Asp Cys Tyr Met Lys Glu His Gly Val Ser Lys Glu Lys
465                 470                 475                 480

Ala Met Gln Arg Phe Tyr Glu Met Ser Thr Asn Ala Trp Lys Asp Ile
                485                 490                 495

Asn Glu Glu Gly Leu Ser Trp Pro Ser Ser Phe Ser Arg Asp Ile Phe
            500                 505                 510

Val Gln Leu Arg Asn Phe Ser Arg Met Val Asp Val Thr Tyr Gly Lys
        515                 520                 525
```

```
Asn Glu Asp Gly Tyr Ser Lys Pro Glu Lys Ile Leu Lys Pro Leu Ile
    530                 535                 540

Ile Ala Leu Phe Val Asp Gln Ile Lys Leu
545                 550

<210> SEQ ID NO 9
<211> LENGTH: 545
<212> TYPE: PRT
<213> ORGANISM: Pogostemon cablin

<400> SEQUENCE: 9

Met Asp Leu Asn Glu Ile Thr Ser Ser Arg Pro Leu Ala Asn Tyr
1               5                   10                  15

His Pro Asn Val Trp Gly Asp Arg Phe Leu Leu His Glu Pro Glu Phe
                20                  25                  30

Thr Cys Gln Ala Gly Glu Lys Gln Leu Val Glu Glu Leu Lys Glu Glu
            35                  40                  45

Val Arg Arg Glu Leu Lys Glu Ala Ser Asn Asp Tyr Leu Arg Gln Leu
 50                  55                  60

Lys Met Val Asp Ala Ile Gln Arg Leu Gly Ile Glu Tyr Leu Phe Glu
65                  70                  75                  80

Glu Glu Ile Asp Glu Ala Leu Arg Asn Leu Leu Ala Lys Phe Glu Asn
                85                  90                  95

Tyr Cys Lys Asp Asn His Asp Met Tyr Ala Thr Ala Leu Ser Phe Arg
            100                 105                 110

Leu Leu Arg Gln His Gly Tyr Lys Val Ser Cys Glu Val Phe Asp Lys
        115                 120                 125

Phe Lys Asp Gly Glu Asp Gly Phe Lys Val Glu Glu Val Met Ala Val
130                 135                 140

Leu Glu Leu Phe Glu Ala Thr His Met Arg Ile His Gly Glu Asp Val
145                 150                 155                 160

Leu Asp Gln Ala Phe Val Phe Thr Arg Asn Tyr Leu Gln Ser Ile His
                165                 170                 175

Ala Thr Leu Ser Asn Pro Ile Ala Lys Gln Val His Asn Ala Leu Asn
            180                 185                 190

Gly Tyr Ser Cys Arg Arg Gly Met Pro Arg Ile Glu Ala Arg Lys Tyr
        195                 200                 205

Ile Pro Ile Tyr Glu Glu Tyr Gly Cys His His Lys Ala Leu Leu Lys
210                 215                 220

Leu Ala Lys Leu Asp Phe Asn Leu Leu Gln Ser Met His Lys Arg Glu
225                 230                 235                 240

Leu Thr Gln Leu Tyr Arg Trp Trp Lys Asp Leu Glu Met Pro Thr Lys
                245                 250                 255

Leu Pro Tyr Ile Arg Asp Arg Leu Val Glu Thr Tyr Phe Trp Asp Met
            260                 265                 270

Gly Phe Tyr Phe Glu Pro Gln Tyr Ala Leu Ala Arg Asn Ile Leu Val
        275                 280                 285

Lys Val Gln Cys Leu Val Ser Ile Phe Asp Thr Phe Asp Ala Tyr
290                 295                 300

Gly Ala Phe Lys Glu Leu Gln Leu Phe Lys Asp Ala Ile Asp Arg Trp
305                 310                 315                 320

Ser Ile Ser Cys Leu Asp Glu Leu Pro Glu Tyr Met Gln Ile Tyr
                325                 330                 335

Lys Leu Val Leu Asp Val Phe Glu Glu Ile Glu Ser His Met Ile Lys
            340                 345                 350
```

```
Gln Gly Thr Ser Tyr Arg Leu Asp Tyr Ala Arg Glu Ala Ile Lys Ile
            355                 360                 365

Val Ile Gly Gly Tyr Phe Asp Glu Ala Lys Trp Arg Glu Glu Glu Tyr
        370                 375                 380

Lys Pro Arg Met Glu Glu Tyr Met Lys Val Ala Thr Lys Ser Ala Ala
385                 390                 395                 400

Tyr Leu Thr Leu Ile Ile Val Ser Phe Val Gly Met Lys Asn Asp Ile
                405                 410                 415

Ala Thr Pro Gln Ala Phe Gln Trp Val Leu Ser Glu Pro Gln Ile Ile
            420                 425                 430

Thr Ala Ser Leu Ala Leu Ala Arg Leu Ser Asn Asp Leu Val Gly Ile
        435                 440                 445

Glu Phe Glu Lys Glu Arg Lys Tyr Ile Ala Thr Ala Val Glu Leu Tyr
    450                 455                 460

Glu Glu Glu His Lys Val Ser Lys Glu Ala Val Leu Glu Leu Arg
465                 470                 475                 480

His Glu Thr Glu Ser Ala Trp Lys Glu Ile Asn Glu Ala Leu Leu Glu
                485                 490                 495

Pro Thr Thr Phe Ala Thr Pro Ile Leu Asp Arg Ile Leu Asn Ser Ala
            500                 505                 510

Arg Val Leu Glu Val Phe Tyr Asp Lys Thr Asp Arg Tyr Thr His Val
        515                 520                 525

Asp Leu Glu Leu Gln Asn Ile Ile Ala Gln Leu Tyr Ile His Pro Ile
    530                 535                 540

Pro
545

<210> SEQ ID NO 10
<211> LENGTH: 552
<212> TYPE: PRT
<213> ORGANISM: Pogostemon cablin

<400> SEQUENCE: 10

Met Glu Leu Tyr Ala Gln Ser Val Gly Val Gly Ala Ala Ser Arg Pro
1               5                   10                  15

Leu Ala Asn Phe His Pro Cys Val Trp Gly Asp Lys Phe Ile Val Tyr
            20                  25                  30

Asn Pro Gln Ser Cys Gln Ala Gly Glu Arg Glu Glu Ala Glu Glu Leu
        35                  40                  45

Lys Val Glu Leu Lys Arg Glu Leu Lys Glu Ala Ser Asp Asn Tyr Met
    50                  55                  60

Arg Gln Leu Lys Met Val Asp Ala Ile Gln Arg Leu Gly Ile Asp Tyr
65                  70                  75                  80

Leu Phe Val Glu Asp Val Asp Glu Ala Leu Lys Asn Leu Phe Glu Met
                85                  90                  95

Phe Asp Ala Phe Cys Lys Asn Asn His Asp Met His Ala Thr Ala Leu
            100                 105                 110

Ser Phe Arg Leu Leu Arg Gln His Gly Tyr Arg Val Ser Cys Glu Val
        115                 120                 125

Phe Glu Lys Phe Lys Asp Gly Lys Asp Gly Phe Lys Val Pro Asn Glu
    130                 135                 140

Asp Gly Ala Val Ala Val Leu Glu Phe Phe Glu Ala Thr His Leu Arg
145                 150                 155                 160

Val His Gly Glu Asp Val Leu Asp Asn Ala Phe Asp Phe Thr Arg Asn
                165                 170                 175
```

```
Tyr Leu Glu Ser Val Tyr Ala Thr Leu Asn Asp Pro Thr Ala Lys Gln
            180                 185                 190

Val His Asn Ala Leu Asn Glu Phe Ser Phe Arg Arg Gly Leu Pro Arg
        195                 200                 205

Val Glu Ala Arg Lys Tyr Ile Ser Ile Tyr Glu Gln Tyr Ala Ser His
    210                 215                 220

His Lys Gly Leu Leu Lys Leu Ala Lys Leu Asp Phe Asn Leu Val Gln
225                 230                 235                 240

Ala Leu His Arg Arg Glu Leu Ser Glu Asp Ser Arg Trp Trp Lys Thr
                245                 250                 255

Leu Gln Val Pro Thr Lys Leu Ser Phe Val Arg Asp Arg Leu Val Glu
            260                 265                 270

Ser Tyr Phe Trp Ala Ser Gly Ser Tyr Phe Glu Pro Asn Tyr Ser Val
        275                 280                 285

Ala Arg Met Ile Leu Ala Lys Gly Leu Ala Val Leu Ser Leu Met Asp
    290                 295                 300

Asp Val Tyr Asp Ala Tyr Gly Thr Phe Glu Glu Leu Gln Met Phe Thr
305                 310                 315                 320

Asp Ala Ile Glu Arg Trp Asp Ala Ser Cys Leu Asp Lys Leu Pro Asp
                325                 330                 335

Tyr Met Lys Ile Val Tyr Lys Ala Leu Leu Asp Val Phe Glu Glu Val
            340                 345                 350

Asp Glu Glu Leu Ile Lys Leu Gly Ala Pro Tyr Arg Ala Tyr Tyr Gly
        355                 360                 365

Lys Glu Ala Met Lys Tyr Ala Ala Arg Ala Tyr Met Glu Glu Ala Gln
    370                 375                 380

Trp Arg Glu Gln Lys His Lys Pro Thr Thr Lys Glu Tyr Met Lys Leu
385                 390                 395                 400

Ala Thr Lys Thr Cys Gly Tyr Ile Thr Leu Ile Ile Leu Ser Cys Leu
                405                 410                 415

Gly Val Glu Glu Gly Ile Val Thr Lys Glu Ala Phe Asp Trp Val Phe
            420                 425                 430

Ser Arg Pro Pro Phe Ile Glu Ala Thr Leu Ile Ile Ala Arg Leu Val
        435                 440                 445

Asn Asp Ile Thr Gly His Glu Phe Glu Lys Lys Arg Glu His Val Arg
    450                 455                 460

Thr Ala Val Glu Cys Tyr Met Glu Glu His Lys Val Gly Lys Gln Glu
465                 470                 475                 480

Val Val Ser Glu Phe Tyr Asn Gln Met Glu Ser Ala Trp Lys Asp Ile
                485                 490                 495

Asn Glu Gly Phe Leu Arg Pro Val Glu Phe Pro Ile Pro Leu Leu Tyr
            500                 505                 510

Leu Ile Leu Asn Ser Val Arg Thr Leu Glu Val Ile Tyr Lys Glu Gly
        515                 520                 525

Asp Ser Tyr Thr His Val Gly Pro Ala Met Gln Asn Ile Ile Lys Gln
    530                 535                 540

Leu Tyr Leu His Pro Val Pro Tyr
545                 550
```

What is claimed is:

1. An isolated nucleic acid encoding a polypeptide having patchoulol synthase activity and comprising the amino acid sequence as set out in SEQ ID NO: 10.

2. A vector comprising the nucleic acid of claim 1.

3. An isolated host cell transformed with the nucleic acid of claim 1.

4. A method of making a recombinant host cell comprising introducing the vector of claim 2 into the host cell.

5. A method of making a patchoulol synthase comprising, culturing an isolated host cell modified to contain at least one nucleic acid sequence under conditions conducive to the production of said patchoulol synthase, wherein said at least one nucleic acid is the nucleic acid according to claim 1.

6. A method of making patchoulol comprising A) transforming an isolated host cell that produces farnesyl-pyrophosphate with the nucleic acid according to claim 1, thereby effecting conversion of farnesyl-pyrophosphate to patchoulol and the subsequent metabolic production of patchoulol, and B) optionally, isolating the patchoulol produced in A).

7. The isolated nucleic acid of claim 1, wherein the nucleic acid is isolated from patchouli leaves.

8. An isolated nucleic acid encoding a polypeptide having patchoulol synthase activity and comprising the nucleotide sequence defined in SEQ ID NO: 5.

9. A vector comprising the nucleic acid of claim 8.

10. An isolated host cell transformed with the nucleic acid of claim 8.

11. A method of making a recombinant host cell comprising introducing the vector of claim 9 into the host cell.

12. A method of making a patchoulol synthase comprising, culturing an isolated host cell modified to contain at least one nucleic acid sequence under conditions conducive to the production of said patchoulol synthase, wherein said at least one nucleic acid is the nucleic acid according to claim 8.

13. A method of making patchoulol comprising A) transforming an isolated host cell that produces farnesyl-pyrophosphate with the nucleic acid according to claim 8, thereby effecting conversion of farnesyl-pyrophosphate to patchoulol and the subsequent metabolic production of patchoulol, and B) optionally, isolating the patchoulol produced in A).

* * * * *

UNITED STATES PATENT AND TRADEMARK OFFICE
CERTIFICATE OF CORRECTION

| | | |
|---|---|---|
| PATENT NO. | : 7,622,288 B2 | Page 1 of 1 |
| APPLICATION NO. | : 11/440105 | |
| DATED | : November 24, 2009 | |
| INVENTOR(S) | : Schalk | |

It is certified that error appears in the above-identified patent and that said Letters Patent is hereby corrected as shown below:

Columns 25-26
Table 1 - continued, column three under the heading "Description", after "reverse degenerated prime deduced from the patchouli", insert -- terpene synthase --.

At columns 25-26, Table 1 - continued, column one, in the row beginning "terpene synthase PatR2", delete "terpene synthase".

The rows will then correctly appear as follows:

| Name | Sequence (5' to 3') | Description |
|---|---|---|
| PatR1 | CCTCRTTHAHDKYCTTCCATBC (SEQ ID NO : 59) | reverse degenerated primer deduced from the patchouli terpene synthase |
| PatR2 | SCATAWKHRTCRWADGTRTCATC (SEQ ID NO : 60) | |

Signed and Sealed this

Twenty-sixth Day of January, 2010

David J. Kappos
*Director of the United States Patent and Trademark Office*

UNITED STATES PATENT AND TRADEMARK OFFICE
CERTIFICATE OF CORRECTION

PATENT NO. : 7,622,288 B2
APPLICATION NO. : 11/440105
DATED : November 24, 2009
INVENTOR(S) : Schalk et al.

Page 1 of 1

It is certified that error appears in the above-identified patent and that said Letters Patent is hereby corrected as shown below:

Title Page, Item (12) delete "Schalk" and insert --Schalk et al.--.

Title Page, Item (75) Inventor should read

-- (75) Inventor: Michel Schalk, Collonges-Sous-Saleve (FR) --.

Signed and Sealed this
First Day of December, 2015

Michelle K. Lee
*Director of the United States Patent and Trademark Office*

UNITED STATES PATENT AND TRADEMARK OFFICE
CERTIFICATE OF CORRECTION

| | | |
|---|---|---|
| PATENT NO. | : 7,622,288 B2 | Page 1 of 1 |
| APPLICATION NO. | : 11/440105 | |
| DATED | : November 24, 2009 | |
| INVENTOR(S) | : Schalk et al. | |

It is certified that error appears in the above-identified patent and that said Letters Patent is hereby corrected as shown below:

Title Page, Item (12) delete "Schalk" and insert --Schalk et al.--.

Title Page, Item (75) Inventor should read

--(75)   Inventors:   Michel Schalk, Collonges-Sous-Saleve (FR), Fabienne Deguerry, Geneva (CH)--.

This certificate supersedes the Certificate of Correction issued December 1, 2015.

Signed and Sealed this
Ninth Day of February, 2016

Michelle K. Lee
*Director of the United States Patent and Trademark Office*